US007144997B2

(12) United States Patent
Miao et al.

(10) Patent No.: US 7,144,997 B2
(45) Date of Patent: Dec. 5, 2006

(54) VERTEBRATE EMBRYONIC PATTERNING-INDUCING PROTEINS, COMPOSITIONS AND USES RELATED THERTO

(75) Inventors: Ningning Miao, Cambridge, MA (US); Monica Wang, Marblehead, MA (US); Nagesh K. Mahanthappa, Cambridge, MA (US); Kevin Pang, Belmont, MA (US)

(73) Assignee: Curis, Inc., Cambridge, MA (US)

( * ) Notice: Subject to any disclaimer, the term of this patent is extended or adjusted under 35 U.S.C. 154(b) by 1680 days.

(21) Appl. No.: 08/900,220

(22) Filed: Jul. 24, 1997

(65) Prior Publication Data

US 2002/0045206 A1 Apr. 18, 2002

(51) Int. Cl.
C07H 12/04 (2006.01)
C12N 15/63 (2006.01)
C12N 15/12 (2006.01)
C12N 1/15 (2006.01)

(52) U.S. Cl. ............. 536/23.51; 435/69.1; 435/69.3; 435/252.3; 435/325; 436/501; 530/300; 530/350; 514/2

(58) Field of Classification Search ........... 536/23.1, 536/24.31; 435/320, 325, 252.3
See application file for complete search history.

(56) References Cited

U.S. PATENT DOCUMENTS

| | | | |
|---|---|---|---|
| 4,456,687 A | 6/1984 | Green | 435/241 |
| 5,223,408 A | 6/1993 | Goeddel et al. | 435/69.3 |
| 5,519,035 A | 5/1996 | Maiese et al. | |
| 5,585,087 A | 12/1996 | Lustig et al. | 424/9.2 |
| 5,643,915 A | 7/1997 | Andrulis, Jr. et al. | 514/279 |
| 5,747,507 A | 5/1998 | Ikegaki et al. | 514/312 |
| 5,759,811 A | 6/1998 | Epstein et al. | 435/69.1 |
| 5,789,543 A | 8/1998 | Ingham et al. | 530/350 |
| 5,837,538 A | 11/1998 | Scott et al. | 435/325 |
| 5,844,079 A | 12/1998 | Ingham et al. | 530/350 |

FOREIGN PATENT DOCUMENTS

| | | |
|---|---|---|
| DE | 3942114 A | 6/1990 |
| EP | 0187 371 A2 | 7/1986 |
| EP | 0249 873 A2 | 6/1987 |
| EP | 0457295 | 11/1991 |
| EP | 0464206 | 1/1992 |
| EP | 0874 048 A2 | 10/1998 |
| EP | 0874048 A2 * | 10/1998 |
| EP | 0874048 A2 | 10/1998 |
| EP | 0879888 A2 | 11/1998 |
| JP | 63 08 81 12 | 4/1988 |
| JP | 02 27 36 10 | 11/1990 |
| JP | 04 30 55 28 | 10/1992 |
| WO | WO 90/02809 | 3/1990 |
| WO | WO 92/15679 | 9/1992 |
| WO | WO 93/08809 | 5/1993 |
| WO | WO 94/02488 | 2/1994 |
| WO | WO 94/28016 | 12/1994 |
| WO | WO 95/18856 | 7/1995 |
| WO | WO 95/23223 | 8/1995 |
| WO | WO 96/09806 | 4/1996 |
| WO | WO 96/11260 | 4/1996 |
| WO | WO 96/16668 | 6/1996 |
| WO | WO 96/17924 | 6/1996 |
| WO | WO 97/11095 | 3/1997 |
| WO | WO 97/45541 | 12/1997 |
| WO | WO 98/12326 | 3/1998 |
| WO | WO 98/14475 | 4/1998 |
| WO | WO 98/21227 | 5/1998 |
| WO | WO 98/30234 | 7/1998 |
| WO | WO 98/30576 | 7/1998 |
| WO | WO 98/35020 | 8/1998 |
| WO | WO 99/00117 | 1/1999 |
| WO | WO 99/00403 | 1/1999 |
| WO | WO 99/01468 | 1/1999 |
| WO | WO 99/04775 | 2/1999 |
| WO | WO 99/10004 | 3/1999 |
| WO | WO 99/39725 | 8/1999 |

OTHER PUBLICATIONS

Hillier et al., Genome Res., vol. 6, pp. 807-828.*
Marigo et al. Genomics, vol. 28 pp. 44-51.*
GenEmbl., Acc. L38517.*
Wang et al. Nature Med., vol. 1, pp. 1184-1188.*
Hammerschmidt et al., Genes & Development, vol. p. 647-658, Feb. 1996.*
Ayala et al., Modern Genetics, p. 678, 1998.*
Miao, N. et al., "Sonic *hedgehog* promotes the survival of specific CNS neuron populations and protects these cells from toxic insult *in vitro*," Journal of Neuroscience, 17:15, 1997, 5891-5899.
FDC Reports, Accession No. 580300025, The Pink Sheet, 58:30, Jul. 22, 1996.
Hynes, M., et al., "Induction of midbrain dopaminergic neurons by Sonic *hedgehog*," Neuron, 15:1, Jul. 1995, 35-44.
Wang, M. Z. et al., "Induction of dopaminergic neurons phenotype in the midbrain by Sonic *hedgehog* protein." Nature Medicine, 1:11, Nov. 1995, 1184-1188.

(Continued)

Primary Examiner—Janet L. Andres
Assistant Examiner—Michael Brannock
(74) Attorney, Agent, or Firm—Fish & Neave IP Group Ropes & Gray LLP

(57) ABSTRACT

It is shown here that hedgehog proteins possess novel activities beyond phenotype specification. Using cultures derived from the embryonic day 14.5 (E14.5) rat ventral mesencephalon, we show that hedgehog is also trophic for dopaminergic neurons. Interestingly, hedgehog not only promotes dopaminergic neuron survival, but also promotes the survival of midbrain GABA-immunoreactive (GABA-ir) neurons.

26 Claims, 8 Drawing Sheets

OTHER PUBLICATIONS

Hulley, P. et al., "Cyclic AMP promotes the survival of dopaminergic neurons in vitro and protects them from toxic effects of MPP+." Journal of Neural Transmission, Supplementum. 46, 1995, 217-228.

Michel, P.P. et al., "Chronic activation of the cyclic AMP signaling pathway promotes development and long-term survival of mesencephalic dopaminergic neurons." Journal of Neurochemistry, 67:4, 1996, 1633-1642.

Huang, X. et al., "Cyclic AMP improves the in vitro survival of mesencephalic dopaminergic neurons by decreasing apoptotic cell death." Society for Neuroscience Abstracts, 22:1-3, 1996, 565.

Epstein, D.J. et al., "Antagonizing cAMP-dependent protein kinase A in the dorsal CNS activates a conserved Sonic *hedgehog* signaling pathway." Development, 122:9, Sep. 1996, 2885-2894.

Hammerschmidt, M. et al., "Protein Kinase A is a common negative regulator of *Hedgehog* signaling in the vertebrate embryo." Genes and Development, 10:6, Mar. 15, 1996, 647-658.

Marigo, V. et al., "Regulation of patched by sonic *hedgehog* in the developing neural tube." Proceedings of the National Academy of Sciences of the U.S.A., 93:18, Sep. 3, 1996, 9346-9351.

Miao, N. et al., "A neurotrophic activity of sonic *hedgehog* promotes the survival of dopaminergic neurons." Cell Transplantation, 5:5, 1996, 17.

Hartikka, J. et al., "Cyclic AMP, but no basic FGi, increases the in vitro survival of mesencephalic dopaminergic neurons and protects them from MPR+ induced degeneration." Journal of Neuroscience, Research, 32:2, Jun. 1992, 190-201.

Drummond, I.A. Human desert *hedgehog*. NCBI Access No. AAB03398, submitted (Jun. 2, 1996).

Anderson, R. et al., "Maintenance of ZPA signaling in cultured mouse limb bud cells", *Devel.* 117:1421-1433 (1993).

Angier, N., "Biologists find key genes that shape patterning of embryos", *New York Times*, Jan. 11, 1994, C-1.

Basier, K. and G. Struhl, "Compartment boundaries and the control of *Drosophila* limb pattern by Hedgehog protein", *Nature* 368:208-214 (1994).

Basier, K. et al., "Control of cell pattern in the neural tube: Reulation of cell differentiation by dorsalin-1, a novel TGFβ family member", *Cell* 73:687-702 (1993).

Bass, S. et al., "Hormone phage: An enrichment method for variant proteins with altered binding properties", *PROTEINS: Stucture, Function, and Genetics* 8:309-314 (1990).

Bejsovec, A. and E. Wieschaus, "Segment polarity gene interactions modulate epidermal patterning in *Drosphila* embryos", *Development* 119:501-517 (1993).

Bienz, M., "Homeotic genes and positional signalling in the *Drosophila viscera*", *TIG* 10:22-26 (Jan. 1994).

Bitgood, M. and A. McMahon, "*Hedgehog* and Bmp genes are coexpressed at many diverse sites of cell-cell cnteraction in the mouse embryo", *Dev. Biol.* 172(1):126-138 (1995).

Blair, S. S., "*Hedghog* digs up an old friend", *Nature*, 373:656-657 (Feb. 23, 1995).

Brand-Saberi, B. et al., "The ventralizing effect of the notochord on somite differentiation in chick embryos", *Anat. Embryol.* 188:239-245 (1993).

Brockes, J., "We may not have a morphogen", *Nature* 350:15 (1991).

Bumcrot, D. A. et al., "Proteolytic processing yields two secreted forms of sonic *hedgehog*", *Mol. Cell. Biol.* 15(4):2294-2303 (Apr. 1995).

Bumcrot, D. A. and A. McMahon, "Sonic *hedgehog*: Making the gradient", *Chem. Biol.* 3(1):13-16 (Jan. 1996).

Bumcrot, D. A. and A. McMahon, "Somite differentiation. Sonic signals somites", *Curr. Biol.* 5(6):612-614 (Jun. 1995).

Charite, J. et al., "Ectopic expression of Hoxb-8 causes duplication of the ZPA in the forlimb and homeotic transformation of axial structures", *Cell* 78:589-601 (1994).

Coffman, et al., "Xotch, the Xenopus homolog of *Drosophila* notch", *Science* 249:1438-1441 (1990).

Concordet, J. and P. Ingham, "Developmental biology. Patterning goes sonic", *Nature* 375(6529):279-280 (May 1995).

Curry, et al., "Sequence analysis reveals homology between two proteins of the flagellar radial spoke", *Mol. Cell. Biol.* 12:3967-3977 (1992).

Davidson, E. H., "How embryos work: a comparative view of diverse modes of cell fat specification", *Develop.* 108:365-389 (1990).

Davis, A. P. and M. R. Capecchi, "Axial homeosis and appendicular skeleton defects in mice with a targeted disruption of hoxd-1", *Devel.* 120:2187-2198 (1994).

Dickinson, W., "Molecules and morphology: Where's the homology", *TIG* 11(4):119-120 (1995).

Dingemanse, M. A. et al., "The expression of liver-specific genes within rat embryonic hepatocytes is a discontinous process", *Differentiation* 56:153-162 (1994).

Dollé, P. et al., "Coordinate expression of the murine Hox-5 complex homeobox-containing genes during limb pattern formation", *Nature* 342:767-772 (1989).

Dollé, P. et al., "Disruption of the Hoxd-13 gene induces localized heterochrony leading to mice wih neotenic limbs", *Cell* 75:431-441 (1993).

Echelard, Y. et al., "Sonic *hedgehog*, a member of a family of putative signaling molecules, is implicated in the regulation of CNS polarity", *Cell* 75:1417-1430 (1993).

Ekker, S. et al., "Distinct expression and shared activities of members of the *hedgehog* gene family of *Xenopus laevis*", *Devel.* 121(8):2337-2347 (Aug. 1995).

Ericson, J. et al., "Sonic *hedgehog* induces the differentiation of ventral forebrain neurons: a common signal for ventral patterning within the neural tube", *Cell* 81(5):747-756 (Jun. 1995).

Ettelaie, C. et al., "The effect of lipid peroxide and lipolysis on the ability of lipoproteins to influence thromboplastin activity", *Biochim. Biophys. Acta.* 1257(1):25-30 (Jun. 1995).

Fahmer, K. et al., "Transcription of H-2 and Qa genes in embryonic and adult mice", *EMBO J.* 6:1265-1271 (1987).

Fallon, J. F. et al., "FGF-2: Aplcal ectodermal ridge growth signal for chick limb development", *Science* 264:104-107 (1994).

Fan, C. et al., "Long-range sclerotome induction by sonic *hedgehog*: Direct role of the amino-terminal cleavage product and modulation by the cyclic AMP signaling pathway", *Cell* 81:457-465 (May 5, 1995).

Fietz, M. et al., "The *hedgehog* gene family in *Drosophila* and vertebrate development", *Devel.* (Suppl.):43-51 (1994).

Forbes, A. J. et al., "Genetic analysis of *hedgehog* signaling in the *Drosophila* embryo", *Devel.* 119 (Suppl.):115-124 (1993).

Francis, P. H. et al., "Bone morphogenetic proteins and a signaling pathway that controls patterning in the developing chick limb", *Devel.* 120:209-218 (1994).

Gallop, M. et al., "Applications of combinatorial technologies to drug discovery. 1. Background and peptide combinatorial libraries", *J. Med. Chem.* 37(9):1233-1251 (1994).

Gérard, M. et al., "Structure and activity of regulatory elements involved in the activation of the Hoxd-11 gene during late gastrulation", *EMBO J.* 12:3539-3550 (1993).

Gurdon, J. B., "The generation of diversity and pattern in animal development", *Cell* 68:185-199 (1992).

Gustin, et al., "Characterization of the Role of Individual Protein Binding Motifs Within the Hepatitis B Virus Enhancer 1 on X Promoter Activity Using Linker Scanning Mutagenesis", Virology 193 : 653-660 (1993).

Hall, T. et al., "A potential catalytic site revealed by the 1.7- A crystal structure of the amino- terminal signaling domain of sonic *hedgehog*", *Nature* 378(6553):212-216 (Nov. 1995).

Halpern, M. E. "Induction of Muscle Pioneers and Floor Plate is Distinguished by the Zebrafish no tail Mutation", Cell 75: 99-111 (1993).

Hamburger, V. and H. L. Hamilton, "A series of normal stages in th development of the chick embryo", *J. Morph.* 88:49-92 (1951).

Hammerschmidt, M. et al., "The world according to *hedgehog*", *TIG* 13(1):14-21 (1997).

Haramis, A. et al., "The limb deformity mutation disrupts the SHH/FGF-4 feedback loop and regulation of 5' HoxD genes during limb pattern formation", *Devel.* 121(12):4161-4170 (Dec. 1995).

Hardy, A. et al., "Gene expression, polarising activity and skeletal patterning in reaggregated hing limb mesenchyme", *Devel.* 121(12):4329-4337 (Dec. 1995).
Harmon, C. S. t al., "Evidence that activation of protein kinase A inhibits human hair follicle growth and hair fibre production in organ culture and DNA synthesis in human and mouse hair follicle organ culture", *British J. Dermatol.* 136:853-858 (1997).
Hatta, K. et al., "The cyclops mutation blocks specification of the floor plate of the zebrafish central nervous system", *Nature* 350:339-341 (1991).
Heberlein, U. et al., "The TGBβ homolog dpp and the segment polarity gene *hedgehog* are required for propagation of a morphogenetic wave in the *Drosophila retina*", *Cell* 75:913-926 (1993).
Heemskerk, J. and S. DiNardo, "*Drosophila hedgehog* acts as a morphogen in cellular patterning", *Cell* 76:449-460 (1994).
Hidalgo, A. and P. Ingham, "Cell patterning in the *Drosophila* segment: spatial regulation of the segment polarity gene patched", *Devel.* 110:291-301 (1990).
Hooper, J. and M. Scott, "The *Drosophile* patched gene encodes a putative membrane protein required for segmental patterning", *Cell* 59:751-765 (1989).
Hynes, R. O., "Integrins: A family of cell surface receptors", *Cell* 48:549-554 (1987).
Ingham, P. W., "Signaling by *hedgehog* family proteins in *Drosophila* and vertebrate development", *Curr. Opin. Genet. Dev.* 5(4):478-484 (Aug. 1995).
Ingham, P. W., "*Hedgehog* points the way", *Current Biology* 4(4):347-350 (1994).
Ingham, P. W., "Localized *Hedgehog* activity controls spatial limits of wingless transcription in the *Drosophila* embryo", *Nature* 366:560-562 (1993).
Ingham, P. W. and A. Hidalgo, "Regulation of wingless transcription in the *Drosophila* embryo", *Devel.* 117:283-291 (1993).
Ingham, P. W. et al., "Role of the *Drosophila patched* gene in positional signaling", *Nature* 353:184-187 (1991).
Izpisúa- Belmonte, J. -C. et al., "Expression of the homeobox Hox-4 genes and the specification of position in chick wing development", *Nature* 350:585-589 (1991).
Izpissúa- Belmonte, J. -C. et al., "Expression of Hox-4 genes in the chick wings like pattern formation to the epithelial- mesenchymal interaction that mediate growth", *EMBO J.* 11:1451-1457 (1992).
Jiang, J. and G. Struhl, "Protein kinase A and *hedgehog* signaling in *Drosophila* limb development", *Cell* 80(4):563-572 (Feb. 1995).
Jessel, T. M. and D. A. Melton, "Diffusible factors in vertebrate embronic induction", *Cell* 68:257-270 (1992).
Johnson, R. L. and C. Tabin, "The long and short of *hedgehog* signaling", *Cell* 81:313-315 (May 5, 1995).
Johnson, R. L. et al., "Patched overexpression alters wing disc size and pattern: transcriptional and post-transcriptional effects on *hedgehog* targets", *Devel.* 121(12):4237-4245 (Dec. 1995).
Johnson, R. L. et al., "Ectopic expression of sonic *hedgehog* alters dorsal-ventral patterning of somites", *Cell* 79(7):1165-1173 (Dec. 1994).
Johnson, R. L. et al., "Mechanism of limb patterning", *Curr. Opin. Genet. Dev.* 4(4):535-542 (Aug. 1994).
Johnson, R. L. et al., "Sonic *hedgehog*: a key mediator of anterior-posterior patterning of the limb and dorso-ventral patterning of axial embryonic structures" *Biochem. Soc. Trans.* 22(3):569-574 (Aug. 1994).
Jones, M. et al., "Involvement of bone morphogenetic protein-4 (BMP-4) and Vgr-1 in morphogenesis and neurogenesis in the mouse", Devel. 111:531-542 (1991).
Kalderon, D., "Morphogenetic signaling. Response to *hedgehog*" *Curr. Biol.* 5(6):580-582 (Jun. 1995).
Koonin, E., "A protein splice-junction motif in *hedgehog* family proteins", *Trends Biochem. Sci.* 20(4):141-142 (Apr. 1995).
Komblihtt, A. R. et al., "Primary structure of human fibronectin: differential splicing may generate at least 10 polypeptides from a single gene", *EMBO J.* 4:1755-1759 (1985).
Kornfeld, R. and S. Kornfeld, "Assembly of asparagine-linked oligosaccharides", *Ann. Rev. Biochem.* 54:631-664 (1985).

Krauss, S. et al., "Expr ssion of the zebrafish paired box gene pax[zf-b] during early neurogenesis", *Devel.* 113:1193-1206 (1991).
Krauss, S. et al., "A functionally conserved homolog of the *Drosophila* Segment polarity gene hh is expressed in tissues with polarizing activity in zebrafish embryos", *Cell* 75:1431-1444 (1993).
Lai, C. et al., "Patterning of the neural ectoderm of *Xenopus laevis* by the amino-terminal product of *hedgehog* autoproteolytic cleavage", *Devel.* 121:2349-2360 (1995).
Laufer, E. et al., "Sonic *hedgehog* and Fgf-4 act through a signaling cascade and feedback loop to integrate growth and patterning of the developing limb bud", *Cell* 79:993-1003 (Dec. 16, 1994).
Lee, J. J. et al., "Secretion and localized transcription suggest a role in positional signaling for products of the segmentation gene *hedgehog*", *Cell* 71:33-50 (1992).
Lee, J. J. et al., "Autoproteolysis in *hedgehog* protein biogenesis", *Science* 266(5190):1528-1537 (Dec. 1994).
Lee, S. J. "Expression of growth/ differentiation factor1 in the nervous system: Conservation of a bicistronic structure", *Proc. Natl. Acad. Sci. USA* 88:4250-4254 (Year).
Levin, M. et al., "A molecular pathway determining left-right asymmetry in chick embryogenesis", *Cell* 82(5):803-814 (Sep. 8, 1995).
Li, W. et al., "Function of protein kinase A in *hedgehog* signal transduction and *drosophila* imaginal disc development", *Cell* 80(4):553-562(Feb. 1995).
Lopez-Martinez, A. et al., "Limb-patterning activity and restricted posterior localization of the amino-terminal product of sonic *hedgehog* cleavage", *Curr. Biol.* 5(7):791-796 (Jul. 1995).
Lumsden, A. and A. Graham, "Neural patterning: A forward role of *hedgehog*", *Curr. Biol.* 5(12):1347-1350 (Dec. 1995).
Ma, C. et al., "Molecular cloning and characterization of rKIk10, a cDNA encoding T-kininogenase from rat submandibular gland and kidney", *Biochem.* 31(44):10922-10928 (1992).
Ma, C. et al., "The segment polarity gene *hedgehog* is required for the progression of the morphogenetic furrow in the developing *Drosophia* eye", *Cell* 75:927-938 (1993).
Ma, C. and K. Moses, "Wingless and patched are negative regulators of the morphogenetic furrow and can affect tissue polarity in the developing *Drosophila* compound eye", *Devel.* 121(8):2279-2289 (Aug. 1995).
Marigo, V. et al., "Biochemical evidence that patched is the *hedgehog* receptor", *Nature* 384:176-179 (1996).
Maccabe, J. A. and B. W. Parker, "The target tissue of limb-bud polarizing activity in the induction of supemumerary structures", *J. Embryol. Exp. Morph.* 53:67-73 (1979).
Maiese, K. et al., "Protein kinases modulate the sensitivity of hippocampal neurons to nitric oxide toxicity and anoxia", *J. Neurosci. Res.* 36:77-87 (1993).
Marti, E. et al., "Distribution of Sonic *hedgehog* peptides in the developing chick and mouse embryo", *Devel.* 121(8):2537-2547 (Aug. 1995).
Marti, E. et al., "Requirement of 19K form of Sonic *hedgehog* for induction of distinct ventral cell types in CNS explants", *Nature* 375(6529):322-325 (May 1995).
Mavillio, F. et al. "Activation of four homeobox gene clusters in human embryonal carcimona cells induced to differentiate by retinoic acid", *Differentiation* 37:73-79 (1988).
McGinnis, W. and R. Krumlauf, "Homeobox genes and axial patterning", *Cell* 68:283-302 (1992).
Mohler, J., "Requirements for *hedgehog*, a segmental polarity gene, in patterning larval and adult cuticle of *drosophila*", *Genetics* 120:1061-1072 (1988).
Mohier, J. and K. Vanl, "Molecular organization and embryonic expression of the *hedgehog* gene involved in cell-cell communication in segmental patterning of *Drosophila*", *Devel.* 115:957-971 (1992).
Morgan, B. A. et al., "Targeted misexpression of Hox-4,6 in the avian limb bud causes apparent homeotic transformations", *Nature* 358:236-239 (1992).
Nakano, Y. et al., "A protein with several possible membrane-spanning domains encoded by the *Drosophila* segment polairty gene patched", *Nature* 341:508-513 (1989).

Ngo, J. et al., "Computational Complexity Protein", Merz and LeGrand, ed. @ Birkhause Boston (1994).

Niswander, L. and G. R. Martin, "FGF-4 and BMP-2 have opposite effects on limb growth", *Nature* 361:68-71(1993).

Niswander, L. et al., "A positive feedback loop coordinates growth and patterning in the vertebrate limb", *Nature*, 371:609-612 (Oct. 13, 1994).

Nohno, T. et al., "Involvement of the Chox-4 Chicken Homeobox Genes in Determination of Anteroposterior Axial Polarity during Limb Development", *Cell*, vol. 64: 1197-1205 (Mar. 22, 1991).

Nohno, T. et al., "Involvement of the Sonic hedgehog gene in chick feather formation", *Biochem. Biophys. Res. Comm.* 206(1): 33-39 (Jan. 1995).

O'Farrell, P. H., "Unanimity waits in the wings", *Nature* 368:188-189 (1994).

Parisi, M. J. et al., "The role of the *hedgehog*/patched signalling pathway in epithelial stem cell proliferation: From fly to human", *Cell Res.* 8:15-21 (1998).

Parr, B. A. et al., "Mouse Wnt genes exhibit discrete domains of expression in the early embryonic CNS and limb buds", *Development* 119:247-261 (1993).

Patel, N. H. et al., "The role of segment polarity genes during *Drosophila* neurogenesis", *Genes & Devel.* 3:890-904 (1989).

Peifer, M., "The two faces of *hedgehog*", *Science* 266(5190):1492-1493 (Dec. 1994).

Perrimon, N. et al., "Generating lineage-specific markers to study *Drosophila* development", *Develop. Genet.*, 12:238-252 (1991).

Perrimon, N., "*Hedgehog* and beyond", *Cell* 80:517-520 (Feb. 24, 1995).

Pham, A. et al., "The Suppressor of *fused* gene encodes a novel PEST protein involved in *Drosophila* segment polairty establishment" *Genetics* 140(2):587-598 (Jun. 1995).

Phillis, J. W. and M. H. O'Regan, "Mechanisms of glutamate and aspartale release in the ischemic rat cerebral cortex", *Brain Res.* 730:150-164 (1996).

Placzek, M. et al., "Induction of floor plate differentiation by contact-dependent, homeogenetic signals", *Development* 117: 205 218 (1993).

Placzek, M. et al., "Orientation of Commissural Axons *in vitro* in response to a floor plate-derived chemoattractant", *Develop.* 110:19-30 (1990).

Pollock, R. A. et al., "Altering the boundaries of Hox3.1 expression: Evidence for antipodal gene regulation", *Cell* 71:911-923 (1992).

Porter, J. et al., "The product of *hedgehog* autoproteolytic cleavage active in local and long-range signalling", *Nature* 374(6520):363-366 (Mar. 23, 1995).

Reeck, et al., "Homology' in proteins and nucleic acids: A terminology muddle and a way out of it", *Cell* 50:667 (Aug. 28, 1987).

Rennie, J., "Super Sonic", *Sci. Amer.* p. 20, (Apr. 1994).

Riddle, R. D. et al., "Sonic *hedgehog* mediates the polarizing activity of the ZPA", *Cell* 75:1401-1416, (Dec. 31, 1993).

Riddle, R. D. et al. "Induction of the LIM homeobox gene Lmx1 by WNT7a established dorsoventral pattern in the vertebrate limb", *Cell* 83:631-640 (Nov. 17, 1995).

Riley, B. B. et al., "Retroviral expression of FGF-2 (bFGF) affects patterning in chick limb bud", *Develop.* 118:95-104 (1993).

Roberts, D. et al., "Sonic *hedgehog* is an endodermal signal inducing Bmp-4 and Hox genes during induction and regionalization of the chick hindgut", *Develop.* 121(10):3163-3174 (Oct. 1995).

Roelink, H. et al., "Floor plate and motor neuron induction vhh-1, a vertebrate homolog of *hedgehog* expressed by the notochord", *Cell* 76:761-775 (Feb. 22, 1994).

Roelink, H. et al., "Floor plate and motor neuron induction by different concentrations of the amino-terminal cleavage product of sonic *hedgehog* autoproteolysis", *Cell*0 81:445-455(May 5, 1995).

Sachiko, I. et al., "Sonic *hedgehog* is expressed in epithelial cells during development of whisker, hair and tooth", *Biochem. Biophys. Res. Commun.* 218:688-693 (1996).

Satoh, S. et al., "Neuroprotective properties of a protein kinase inhibitor against Ischaemia-induced nueronal damage in rats and gerbils", *Br. J. Pharmacol.* 118:1592-1596 (1996).

St. Jacques, B. et al., "Sonic *hedgehog* signaling Is essential for hair development", *Curr. Biol.* 8:1058-1068 (1998).

Sasaki, H. and B. L. M. Hogan, "Differential expression of multiple fork head related genes during gastrulation and axial pattern formation in the mouse embryo", *Develop.* 118:47-59 (1993).

Savage, M. et al., "Distribution of FGF-2 suggests it has a role in chick limb bud growth", *Devel. Dynamics* 198:159-170 (1993).

Schuske, K. et al., "Patched overexpression causes loss of wingless expression in *drosophila* embryos", *Devel. Biol.* 164 : 300-311 (1994).

Smith, J. C., "*Hedgehog*, the floor plate, and the zone of polarizing activity", *Cell* 76:193-196 (1994).

Stachel, S. E. et al., "Lithium perturation and goosecoid expression identify a dorsal specification pathway in the pregastrula zebrafish", *Develop.* 117:1261-1274 (1993).

Stolow, M. and Shi, Y., "Xenopus sonic *hedgehog* as a potential morphogen during embryogenesis and thyroid hormone-dependent metamorphosis", *Nucl. Acids Res.* 23(13):2555-2562 (1995).

Tabata, T. and T. B. Kornberg, "*Hedgehog* is a signaling protein with a key role in patterning *drosophila* imaginal discs", *Cell* 76: 89-102 (1994).

Tabata, T. et al., "The *Drosophila hedgehog* gene is expressed specifically in posterior compartment cells and is a target of engrailed regulation", *Genes & Develop.* 6:2635-2645 (1992).

Tabin, C. J., "Retinoids homeoboxes, and growth factors: Toward molecular models for limb develoment", *Cell* 66:199-217 (Jul. 26, 1991).

Tanabe, Y. et al., "Induction of motor neurons by sonic *hedgehog* is independent of floor plate differentiation", *Curr. Biol.* 5(6):651-658 (Jun. 1995).

Tanaka, E. and A. Gann, "Limb development : The budding role of FGF", *Curr. Biol.* 5(6):594-597 (Jun. 1995).

Tashiro, S. et al., "Structure and expression of *hedgeho*, a *Drosophila* segment-polarity gene required for cell-cell communication", *Gene* 124:183-189 (1993).

Taylor, A. M. et al., "Contrasting distributions of patched and *hedgehog* proteins in the *Drosophila* embryo", *Mech. Develop.* 42: 89-96 (1993).

Thaller, C. and G. Eichele, "Identification and spatial distribution of retinoids in the devloping chick limb bud", *Nature* 327 : 625-628(1987).

Thummel, et al., "Vectors for *Drosophila* P-element-mediated transformation and tissue culture transfection", *Gene* 74:445-456 (1988).

Tickle, C. et al., "A quantitative analysis of the effect of all-trans-retinoic acid on the pattern of chick wing development", *Develop. Biol.* 109:82-95 (1985).

Tickle, C. eta l., "Vertebrate limb development", *Curr. Opin. Genet. Dev.* 5(4):478-484 (1995).

Tickle, C. and G. Eichle, "Vertebrate limb development", *Ann. Rev. Cell Biol.* 10:121-152(1994).

Van Straaten, H. W. M. et al., "Effect of the notochord on the differentiation of a floor plate area in the neural tube of the chick embryo", *Anat. Embryol.* 177:317-324 (1988).

Vogel, A. and C. Tickle, "FGF-4 maintains polarizing activity of posterior limb bud cells *in vivo* and *in vitro*", *Develop.* 119:199-206 (1993).

Wallace, et al., "Oligonucleotide probes for the screening of recombinant DNA libraries", *Methods in Enzymol.* 152:432-443 (1987).

Wanek, N. t al., "Conversion by retinoic acid of anterior cells into ZPA cells in the chick wing bud", *Nature* 350:81-83 (Mar. 7, 1991).

Yamada, T. et al., "Control of cell pattern in the developing nervous system: Polarizing activity of the floor plate and notochord", *Cell*, 64:635-647, (Feb. 8, 1991).

Yang, Y. and L. Niswander, "Interaction between the signaling molecules WNTZ7a and SHH during vertebrate limb development: dorsal signals regulate anteroposterior patterning", *Cell* 80:939-947 (Mar. 24, 1995).

Yun-Bo Shi, "Cell-cell and cell ECM interactions in epithelial apoptosis and cell renewal during frog intestinal development", *Cell Biochem. Biophys.*27:179-202 (1995).

Zappavigna, et al., "Hox4 genes encode transcription factors with potential auto- and cross-regulatory capacities", *EMBO J.* 10(13):4177-4187 (1991).

Zardoya, et al., "Evolution and orthology of *hedgehog* genes", *TIG* 12(12):496-497 (1996).

Zecca, M. et al., "Sequential organizing activities of *engrailed, hedgehog* and *decapentaplegic* in the *Drosophila* wing", Dev. 121:2265-2278 (Aug. 1995).

\* cited by examiner

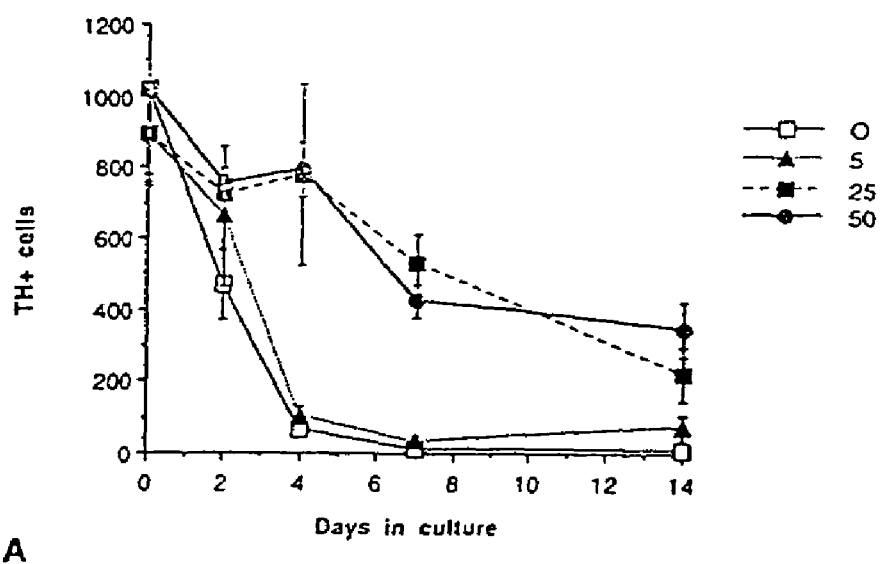
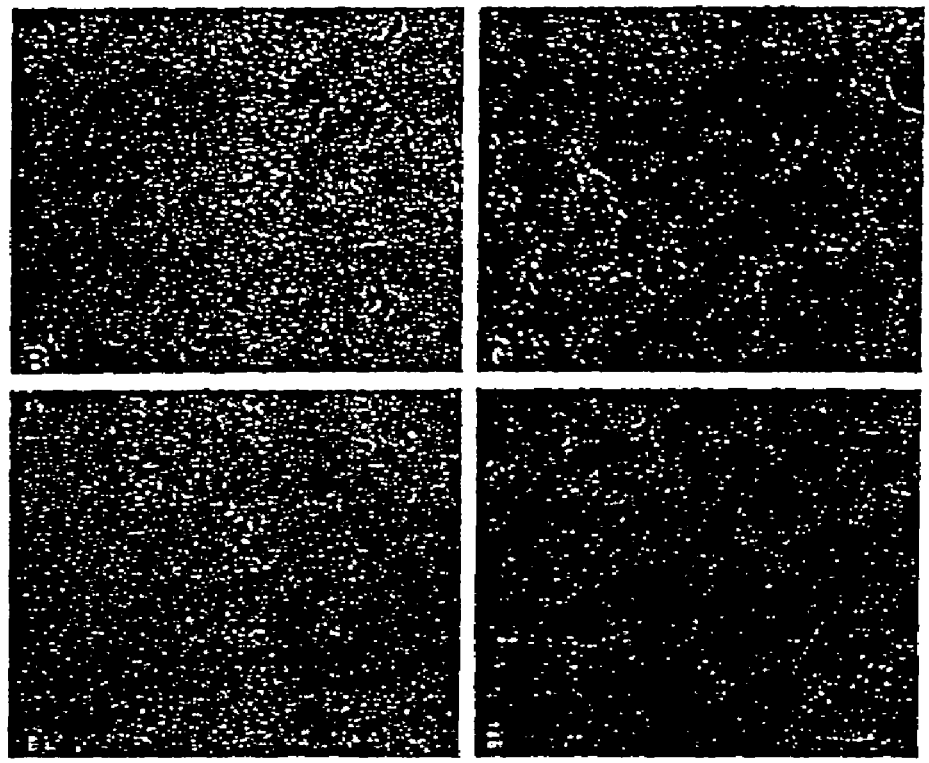
FIG. II

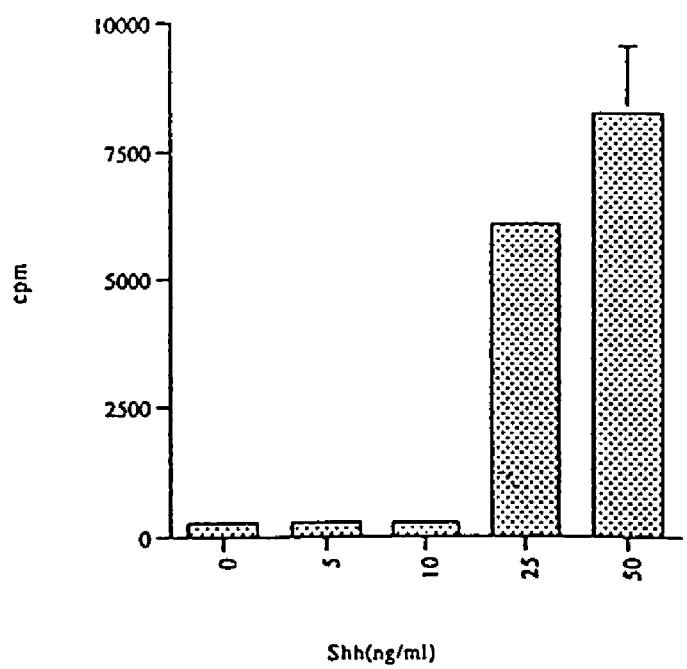
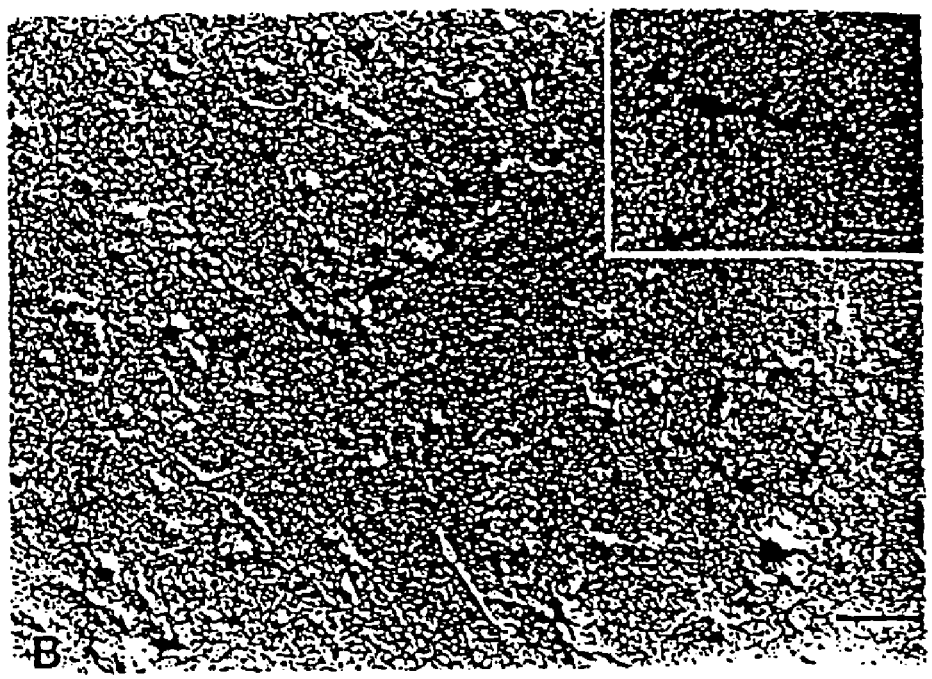
FIG. III

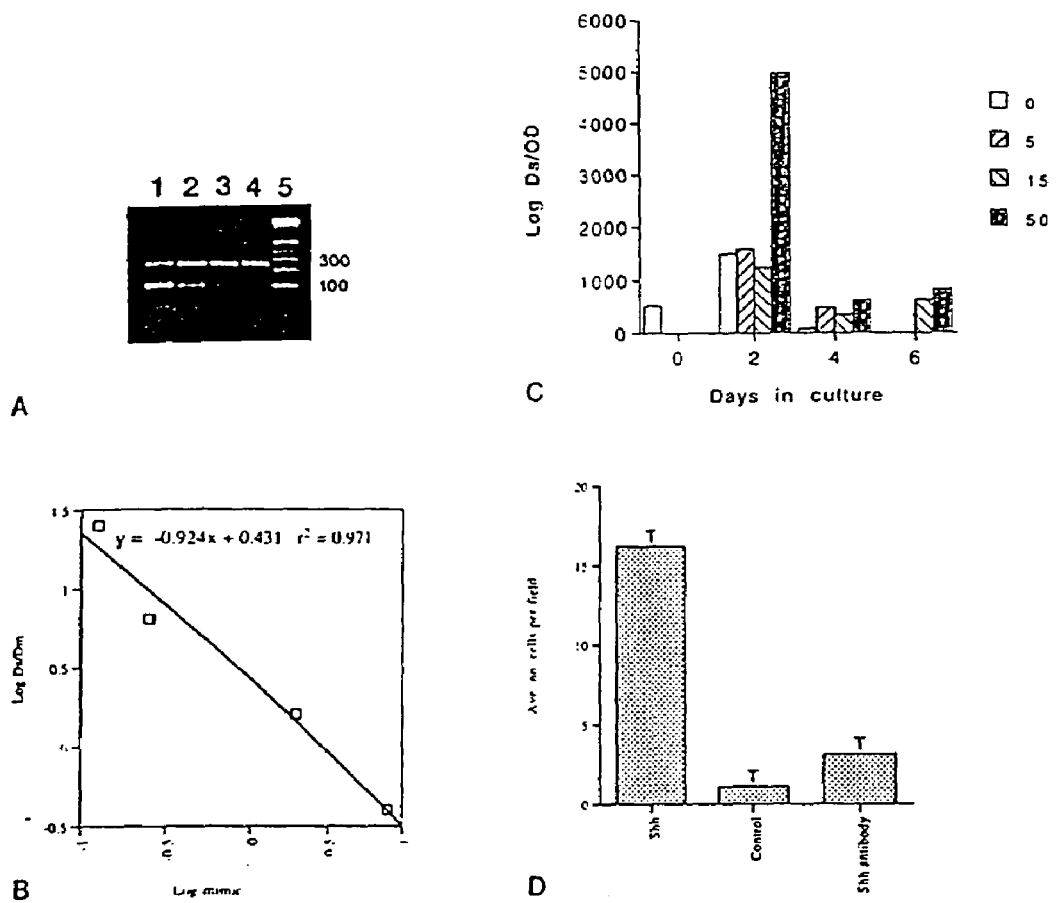
FIG. IV

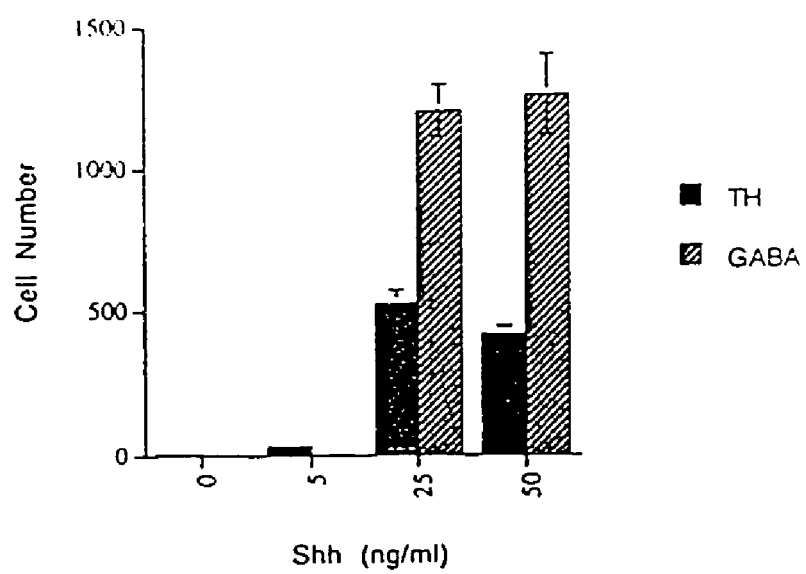
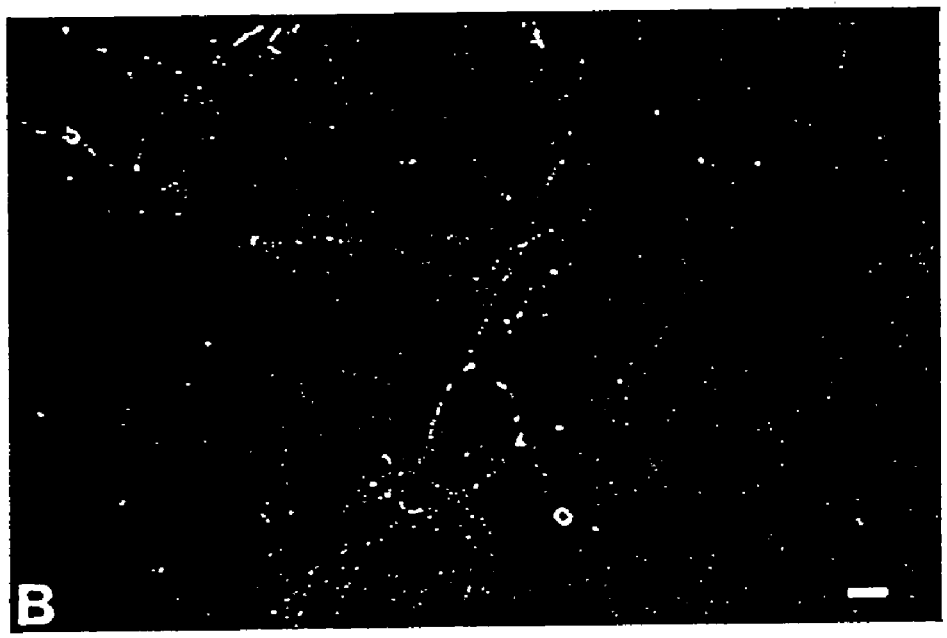
FIG. V

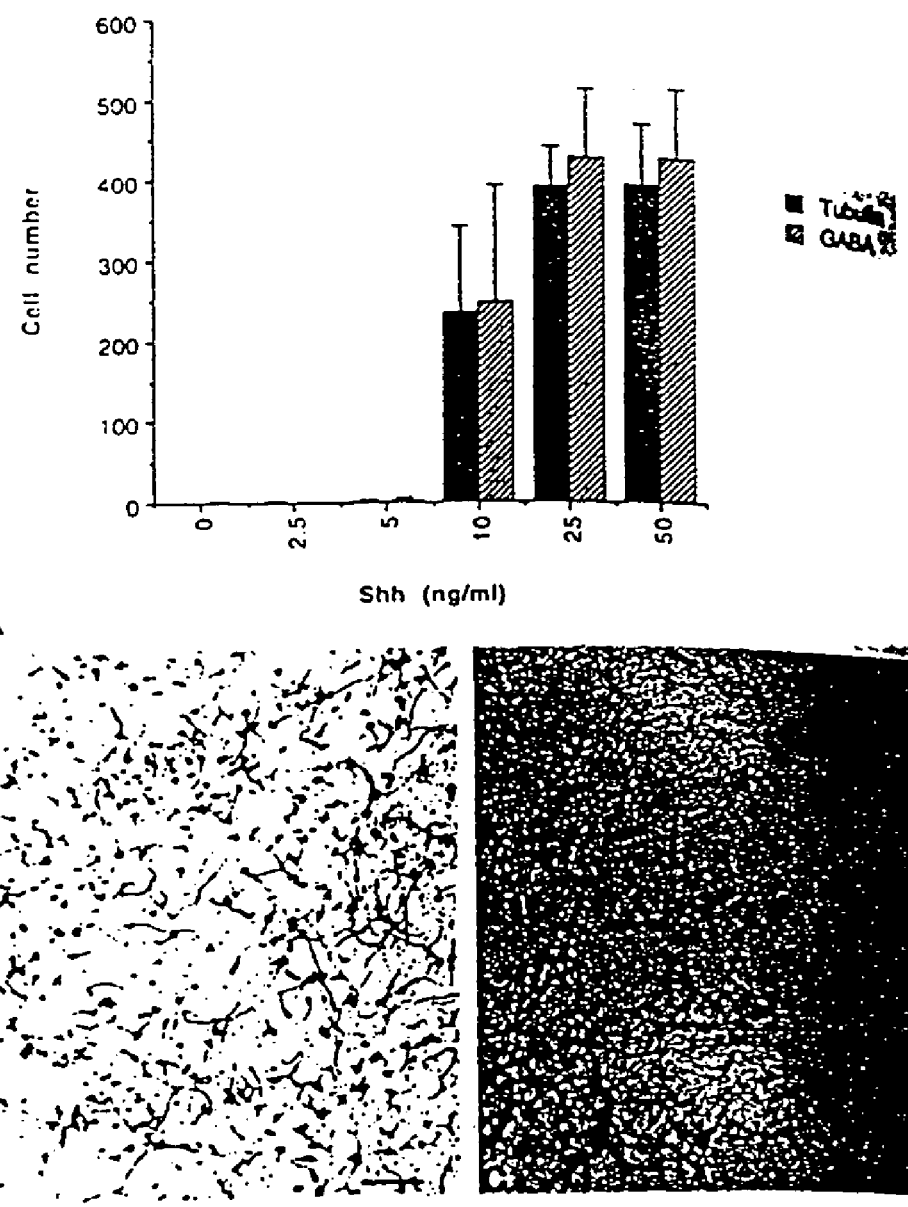
FIG. VI

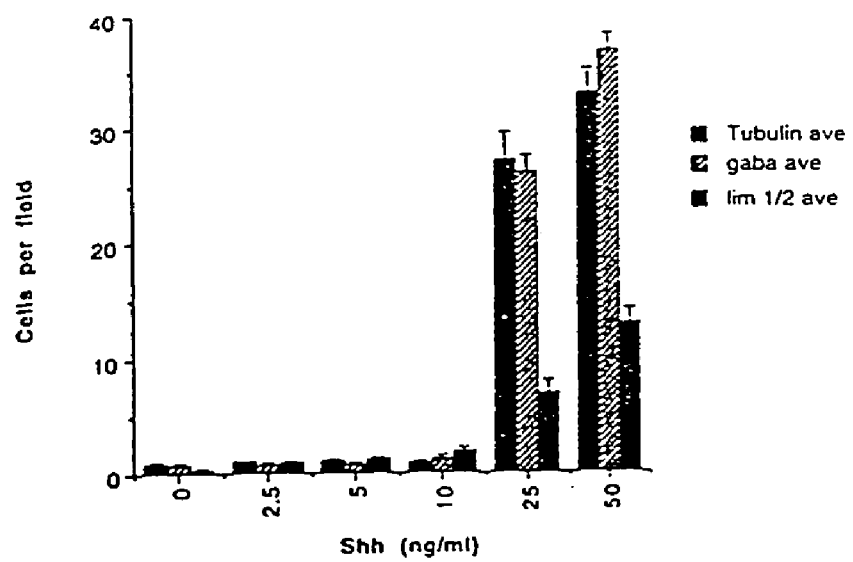
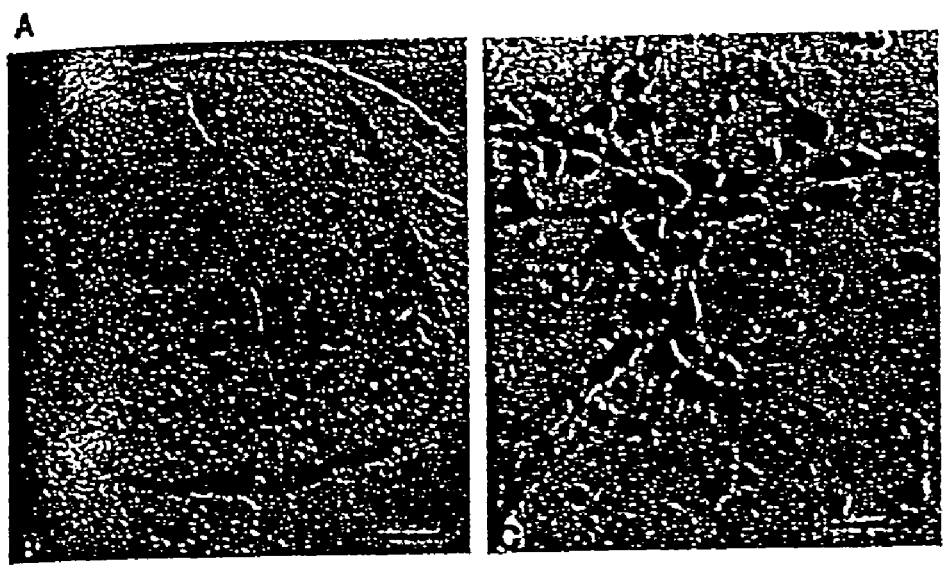
FIG. VII

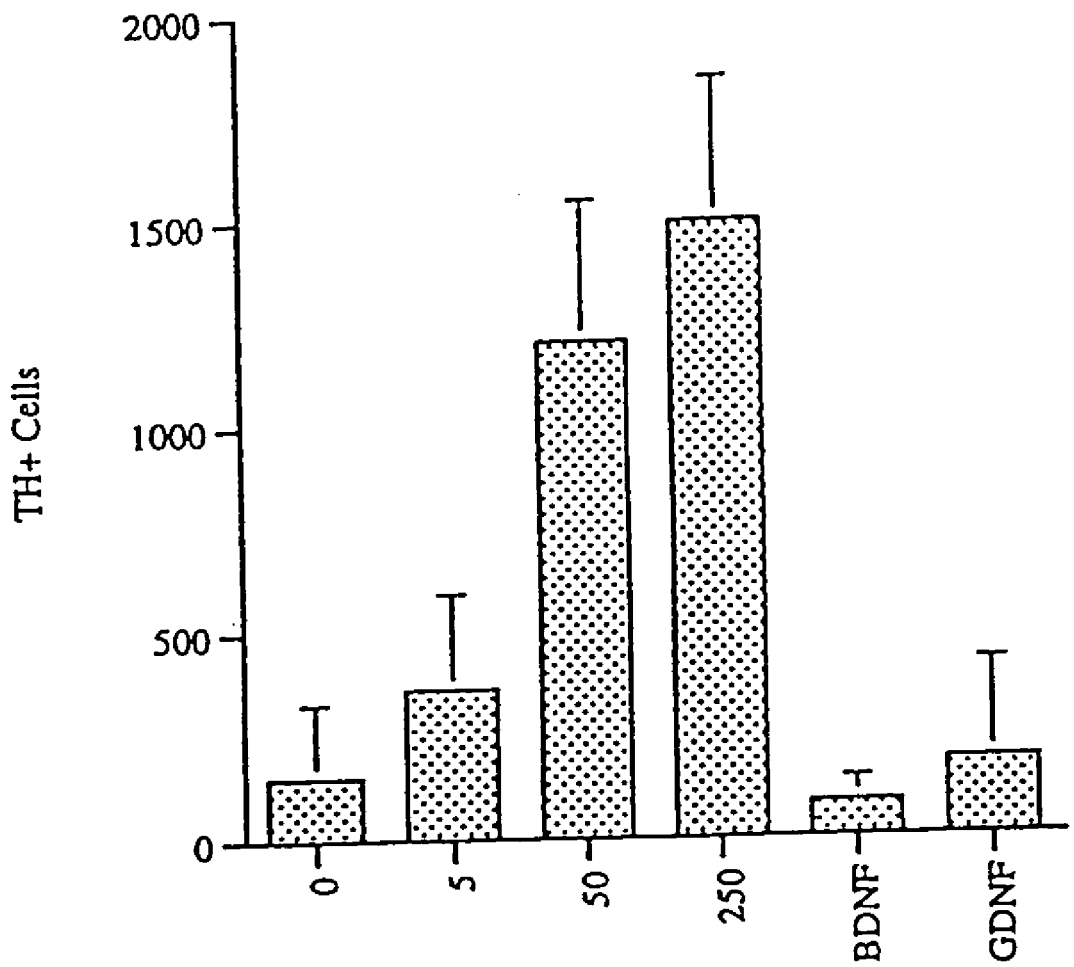
FIG. VIII

VERTEBRATE EMBRYONIC PATTERNING-INDUCING PROTEINS, COMPOSITIONS AND USES RELATED THERTO

BACKGROUND OF THE INVENTION

The individual symptoms of Parkinson's disease have been described by physicians from the time of Galen, but their occurence as a syndrome was not recognized until 1817. In that year James Parkinson, a London physician, published an essay in which he argued that several different motor symptoms could be considered together as a group forming a distinctive condition. His observations are interesting not only because his conclusion was correct but also because he made his observations in part at a distance by watching the movements of Parkinsonian victims in the street of London. Parkinson's disease has been called at different times the shaking palsy or its Latin equivalent, paralysis agitans, but received its commoner designation from Jean Charcot, who suggested that the disease be renamed to honor James Parkinson's recognition of its essential nature.

Parkinson's disease is fairly common, estimates of its incidence varying from 0.1 to 1.0% of the population. It is also of considerable interest for a number of other reasons. First, the disease seems related to the degeneration of the substantia nigra, and to the loss of the neurotransmitter substance dopamine, which is produced by cells of this nucleus. The disease, therefore, provides an important insight into the role of this brainstem nucleus and its neurotransmitter in the control of movement. Second, because a variety of pharmacological treatments for Parkinson's disease relive different features of its symptoms to some extent the disease provides a model for understanding pharmacological treatments of motor disorders in their more general aspects. Third, altought Parkinson's disease is described as a disease entity, the symptoms vary enormously among people, thus making manifest the complexity with which the components of movement are organized to produce fluid motion. Fourth, because many of the smptoms of Parkinson's disease strikingly resemble changes in motor activity that occur as a consequense of aging, the disease provides indirect insight into the more general problems of neural changes in aging.

There are three major types of Parkinson's disease: idiopathic, postencephalitic, and drug-induced. Parkinson's diseases may also result from arteriosclerosis, may follow poisoning by carbon monoxide or manganese intoxication, or may result from syphilis or the development of tumors. As is suggested by its name, the idiopathic cause of Parkinson's disease is not known. Its origin may be familiar, or it may be part of the aginig process, but it is also widely thought that it might have a viral origin. It most often occurs in people who are over 50 years of age. The postencephalitic form originated in the sleeping sickness that appeared in the winter of 1916–1917 and vanished by 1927. Although the array of symptoms wsa bewilderingly varied; such that hardly any two patients seemed alike, Constantin von Economo demonstrated a unique pattern of brain damage associated with a virus infection in the brains of patients who had died from the disease. A third of those affected died in the acute stages of sleeping sickness in states either of coma or of sleeplessness. Altough many people seemed to completely recover from the sickness, most subsequently developed neurological or psychiatric disorders and parkinsonism. The latency between the initial and subsequent ocurrences of the disease has never been adequately explained. Specify searches for vital particles or virus specific products in Parkinson patients have revealed no evidence of viral cause. The third major cause of Parkinson's disease is more recent, and is associated with ingestion of various drugs, particularly major tranquilizers that include reserpine and several phenothiazine and butyrophenone derivatives. The symptoms are usually reversible, but they are difficult to distinguish from those of the genuine disorder.

Recently it has been found that external agents can cause symptoms quite rapidly. Langston and coworkers have reported that a contaminat of synthetic heroin, MPTP, when taken by drug users is converted into MPP which is extremely toxic to dopamine cells. A number of young drug users were found to display a complete parkinsonian syndrome after using contaminated drugs. This finding has suggested that other substances might cause similar effects. Demographic studies of patient admission in the cities of Vancouver and Helsinki show an increase in the incidence of patients getting the disease at ages younger than 40. This has raised the suggestion that water and air might contain environmental toxins that work in a fashion similar to MPTP.

Although Parkinsonian patients can be separated into clinical groups on the basis of cause of the disease, it is nevertheless likely that the mechanisms producing the symptoms have a common origin. Either the substantia nigra is damaged, as occurs in idiopathic and postencephalitic cases or the activity of its cells is blocked or cells are killed, as occurs in drug induced parkinsonism. The cells of the substantia nigra contain a dark pigment in Parkinson's disease this area is depigmented by degeneration of the melatonin containing neurons of the area. The cells of the substantia nigra are the point of origin of fibers that go to the basal ganglial frontal cortex and to the spinal cord. The neurotransmitter at the synapses of these projection is dopamine. It has been demonstrated by bioassay of the brains of deceased parkinsonian patients, and by analysis of the major metabolite of dopamine, homovanallic acid, which is excreted in the urine, that the amount of brain dopamine is reduced by over 90% and is often reduced to undetectable amounts. Thus the cause of Parkinson's disease has been identified with some certainty as a lack of dopamine or in drug induced cases with a lack of dopamine action.

Certain attempts have been made to treat Parkinson's disease. One proposed treatment for Parkinson's disease is Sinemet CR, which is a sustained-release tablet containing a mixture of carbidopa and levodopa, available from The DuPont Merck Pharmaceutical Co. Another proposed treatment for Parkinson's disease is Eldepryl, which is a tablet containing selefiline hydrochloride, available from Somerset Pharmaceuticals, Inc. Another proposed treatment for Parkinson's disease is Parlodel, which is a tablet containing bromocriptine mesylate, available from Sandoz Pharmaceuticals Corporation.

SUMMARY OF THE INVENTION

One aspect of the present application relates to a method for promoting the survival of dopaminergic or GABAergic neurons by contacting the cells, in vitro or in vivo, with a hedgehog therapeutic or ptc therapeutic in an amount effective increasing the rate of survival of the neurons relative to the absence of administration of the hedgehog therapeutic or ptc therapeutic.

One aspect of the present application relates to a method for promoting the survival of neurons of the substantia nigra by contacting the cells, in vitro or in vivo, with a hedgehog therapeutic or ptc therapeutic in an amount effective increasing the rate of survival of the neurons relative to the absence of administration of the hedgehog therapeutic or ptc therapeutic.

In other embodiments, the subject method can be used for protecting dopaminergic and/or GABAergic neurons of a mammal from neurodegeneration; for preventing or treating neurodegenerative disorder; for treatment of Parkinson's; for treatment of Huntington's; and/or for treatment of ALS. In embodiments wherein the patient is treated with a ptc therapeutic, such therapeutics are preferably small organic molecules which mimic hedgehog effects on patched-mediated signals.

Wherein the subject method is carried out using a hedgehog therapeutic, the hedgehog therapeutic preferably a polypeptide including a hedgehog portion comprising at least a bioactive extracellular portion of a hedgehog protein, e.g., the hedgehog portion includes at least 50, 100 or 150 amino acid residues of an N-terminal half of a hedgehog protein. In preferred embodiments, the hedgehog portion includes at least a portion of the hedgehog protein corresponding to a 19 kd fragment of the extracellular domain of a hedgehog protein.

In preferred embodiments, the hedgehog portion has an amino acid sequence at least 60, 75, 85, or 95 percent identical with a hedgehog protein of any of SEQ ID Nos. 10–18 or 20, though sequences identical to those sequence listing entries are also contemplated as useful in the present method. The hedgehog portion can be encoded by a nucleic acid which hybridizes under stringent conditions to a nucleic acid sequence of any of SEQ ID Nos. 1–9 or 19, e.g., the hedgehog portion can be encoded by a vertebrate hedgehog gene, especially a human hedgehog gene.

In other embodiments, the subject method can be carried out by administering a gene activation construct, wherein the gene activation construct is designed to recombine with a genomic hedgehog gene of the patient to provide a heterologous transcriptional regulatory sequence operatively linked to a coding sequence of the hedgehog gene.

In still other embodiments, the subject method can be practiced with the administration of a gene therapy construct encoding a hedgehog polypeptide. For instance, the gene therapy construct can be provided in a composition selected from a group consisting of a recombinant viral particle, a liposome, and a poly-cationic nucleic acid binding agent.

Another aspect of the present invention relates to the cloning of various human hedgehog genes, e.g., human Dhh and Ihh. In a preferred embodiment, there is provided an isolated and/or recombinantly produced polypeptide comprising an amino acid sequence which is at least 95 percent identical to a sequence represented by SEQ ID. NO. 16 or 17, or a bioactive extracellular fragment thereof. In another embodiment, there is provided an isolated and/or recombinantly produced polypeptide encoded by a nucleic acid which hybridizes under stringent conditions to a sequence selected from the group consisting of SEQ ID. NO. 16 and SEQ ID. NO. 17. In a preferred embodiment, the polypeptide is formulated in a pharmaceutically acceptable carrier.

Preferred bioactive fragments of the human Ihh and Dhh proteins include from about residues 28–202 of SEQ ID No. 16 and 23–198 of SEQ ID No. 17, respectively. Longer or shorter fragments are contemplated, as for example, those which are 5, 10, 15 or 20 amino acids shorter on either or both the N-terminal and C-terminal ends of the fragment.

In certain embodiments, the polypeptide is purified to at least 80% by dry weight, and more preferably 90 or 95% by dry weight.

Another aspect of the present invention provides an isolated nucleic acid encoding a polypeptide comprising a hedgehog amino acid sequence which is at least 95 percent identical to a hedgehog protein selected from the group consisting of SEQ ID No:16 and SEQ ID No:17, or bioactive fragments thereof, e.g., the hedgehog amino acid sequence (i) binds to a patched protein, (ii) regulates differentiation of neuronal cells, (iii) regulates survival of differentiated neuronal cells, (iv) regulates proliferation of chondrocytes, (v) regulates proliferation of testicular germ line cells, or (vi) functionally replaces drospholia hedgehog in transgenic drosophila fly, or a combination thereof.

In other preferred embodiments, the isolated nucleic acid encodes a polypeptide having a hedgehog amino acid sequence encoded by a nucleic acid which hybridizes under stringent conditions to a nucleic acid sequence selected from the group consisting of SEQ ID No:7 and SEQ ID No:8, which hedgehog amino acid sequence of the polypeptide corresponds to a natural proteolytic product of a hedgehog protein. Such polypeptides preferably (i) binds to a patched protein, (ii) regulates differentiation of neuronal cells, (iii) regulates survival of differentiated neuronal cells, (iv) regulates proliferation of chondrocytes, (v) regulates proliferation of testicular germ line cells, and/or (vi) functionally replaces drospholia hedgehog in transgenic drosophila fly, or a combination thereof.

In preferred embodiments, the nucleic acid encodes a hedgehog amino acid sequence identical to a hedgehog protein selected from the group consisting of SEQ ID No:16 and SEQ ID No:17.

Another preferred ebodiment provides an isolated nucleic acid comprising a coding sequence of a human hedgehog gene, encoding a bioactive hedgehog protein.

Still another aspect of the present invention relates to an expression vector, capable of replicating in at least one of a prokaryotic cell and eukaryotic cell, comprising a nucleic acid encoding a Dhh or Ihh polypeptide described above.

The present invention also provides a host cell transfected with such expression vectors; as well as methods for producing a recombinant hedgehog polypeptide by culturing such cells in a cell culture medium to express a hedgehog polypeptide and isolating said hedgehog polypeptide from the cell culture.

Still another aspect of the present invention provides a recombinant transfection system, e.g., such as may be useful for gene therapy, comprising (i) a gene construct including the coding sequence for a human Ihh or Dhh protein, operably linked to a transcriptional regulatory sequence for causing expression of the hedgehog polypeptide in eukaryotic cells, and (ii) a gene delivery composition for delivering said gene construct to a cell and causing the cell to be transfected with said gene construct. For instance, the gene delivery composition is selected from a group consisting of a recombinant viral particle, a liposome, and a poly-cationic nucleic acid binding agent.

Another aspect of the present invention provides a probe/primer comprising a substantially purified oligonucleotide, said oligonucleotide containing a region of nucleotide sequence which hybridizes under stringent conditions to at least 10 consecutive nucleotides of sense or antisense sequence of SEQ ID No. 7 or 8, or naturally occuring mutants thereof. In preferred embodiments, the probe/primer includes a label group attached thereto and able to be detected. The present invention also provides a test kit for detecting cells which contain a hedgehog mRNA transcript, and includes such probe/primers.

Still another embodiment of the present invention provides a purified preparation of an antisense nucleic acid which specifically hybridizes to and inhibits expression of a gene encoding a human Ihh or Dhh hedgehog protein under physiological conditions, which nucleic acid is at least one of (i) a synthetic oligonucleotide, (ii) single-stranded, (iii) linear, (iv) 20 to 50 nucleotides in length, and (v) a DNA analog resistant to nuclease degradation.

BRIEF DESCRIPTION OF THE DRAWINGS

FIG. 2. Shh promotes the survival of TH+ neurons of the ventral mesencephalon. (A) Timecourse and dose response of the Shh effect. The number of TH+ neurons in control cultures (O ng/ml Shh) began to decline dramatically by 5 days in vitro. In cultures treated with Shh at 25 and 50 ng/ml there were significantly greater numbers of TH+ nurrons over control-through 24 days in vitro (from 5 to 24 days, $p <0.001$ at 25 and 50 ng/ml). The 50 ng/ml dose typically gave a 50–100% increase over controls at all time points (error bars s.e.m.) P-h'otomicrographs of TH+ neurons in 50. ng/ml Shh treated (B-,,,--D) and control (C, E) cultures, 2 days (B, C) and 7 days (D, E) post-plating. Note that in addition to an increased number of TH+-cell bodies, the Shh treated cells—show extensive neuritic processes. Scale bar=200 um.

FIG. 3. Transport of 3H-Dopamine. The identity and functionality of the surviving midbrain neurons was assessed by their ability to specifically transport dopamine. (A) Addition of 25 ng/ml Shh resulted in a 22-fold increase in 3H-DA cell uptake over controls and lower Shh concentrations. 50 ng/ml Shh gave a 30-fold increase in 3H-DA uptake (error bars=s.d.) ($p<0.005$ at 25 and 50 ng/ml). (B) Autoradiography was performed on sister plates to visualize dopamine transport. Only cells with neuronal morphology transported 3H-DA (inset). Scale bar=50 Jim, inset 15 m.

FIG. 4. Specificity of Shh activity. (A) QC-PCR gel. Lanes 1–4 are CDNA from midbrain cultures that have been co-amplified with successive 4-fold dilutions of mimic oligo. Lane 5 is DNA marker lane. Ptc target is 254 bp and mimic is 100 bp(B) Representative plot (corresponding to A) of the log concentration of competitive mimic versus the log of the obtained band densities of target and mimic PCR substrates demonstrates the linearity of the amplification reaction. The extrapolated value of ptc message in the CDNA tested is determined to be equal to the value of mimic concentration where Log Ds/Dm=0. See main text for details of the procedure. Doses in ng/ml; Ds=density of test substrate; Dm=density of competitive mimic. The r 2 value shows that determinations made within this range vary within 3%. (C) Administration of Shh induces ptc expression in a dose response that parallels the survival curve. The values are expressed as number of target molecules (log Ds) per total amount of CDNA used in each reaction as measured by optical density at 260 nm (OD) and were determined as demonstrated in A and B. At 4 days in vitro Shh at 5 ng/ml increases ptc expression over control, and 50 ng/ml increases expression of ptc over the level found in the ventral mesencephalon at the time of dissection. (D) Affinity purified anti-Shh antibody inhibited the Shh neurotrophic response ($p<0.001$). Cultures were maintained for 5 days. Shh was added at a concentration of 50 ng/ml, and in the co-administration of 5 Shh and anti-Shh ("Shh antibody") Shh was added at 0 g/ml and anti-Shh was added as a 5-fold molar excess (error bars s.e.m.).

FIG. 5. Shh also supports the survival of midbrain-GABA+ neurons. (A) In addition to supporting the survival of TH+ cells in the midbrain cultures, Shh promotes the survival of GABA-immunoreactive neurons with a similar dose response (error bars=s.e.m.) (For TH, p, 0.001 at 25 and 50 ng/ml; for GABA, $p<0.001$ at 25 and 50 ng/ml). (B) Double level immunofluorescence of SSH-treated cultures shows that the majority of the GABA+ cells (orange) do not overlap with the TH+ cells (green); scale bar=15 m.

FIG. 6. Shh effects on striatal cultures. (A) At concentrations of 10 ng/ml and higher, Shh promotes neuronal survival as gauged by staining for tubulin PIII, and these cells are exclusively GABA+(error bars=S.D.) (tubulin PIII, $p<0.001$ at 25 and 50 ng/ml; GABA, $p<0.001$ at 25 and 50 ng/ml). Typical fields of neurons treated with 50 ng/ml Shh stained for tubulin plll (B) and GABA+(C) are shown; scale bar=100 gm.

FIG. 7. Shh effects on ventral spinal cultures. (A) At concentrations of 25 ng/ml and higher, Shh promotes neuronal survival as gauged by staining for tubulin PIII. The majority of the cells stain positively for GABA, while a subset stain for the nuclear marker of spinal interneurons, Lim-½ (error bars=s.e.m.) (tubulin pill, $p <0.001$ at 25 and 50 ng/ml; lim ½, $p<0.001$ at 5,10,25, and 50 ng/ml; GABA, $p<0.001$ at 25 and 50 ng/ml). Typical staining for Lim-½ in the E14 rat spinal cord (B, scale bar=100 m), and spinal neurons cultured in the presence of 50 ng/ml Shh (C, scale bar=20 m).

FIG. 8. Shh protects midbrain TH+ neurons from neurotoxic insult. Cultures of ventral mesencephalon neurons were cultured in the indicated concentrations of Shh (ng/ml). MPP+ was added at 4 days in vitro for 48 hours. Cultures were then washed extensively and cultured for an additional 48 hours to allow clearance of dying neurons. Protection from MPP+ neurotoxicity could be seen at 5 ng/ml, with the effect saturating at 50 ng/ml. BDNF was used at 10 ng/ml, and GDNF at 20 ng/ml (error bars=s.e.m.) (Shh, $p<0.001$ at 50 and 250 ng/ml; BDNF no significance; GDNF, $p<0.05$). Note that the plating density used in this experiment was twice that used in FIG. 2.

DETAILED DESCRIPTION OF THE INVENTION

Figure 1:
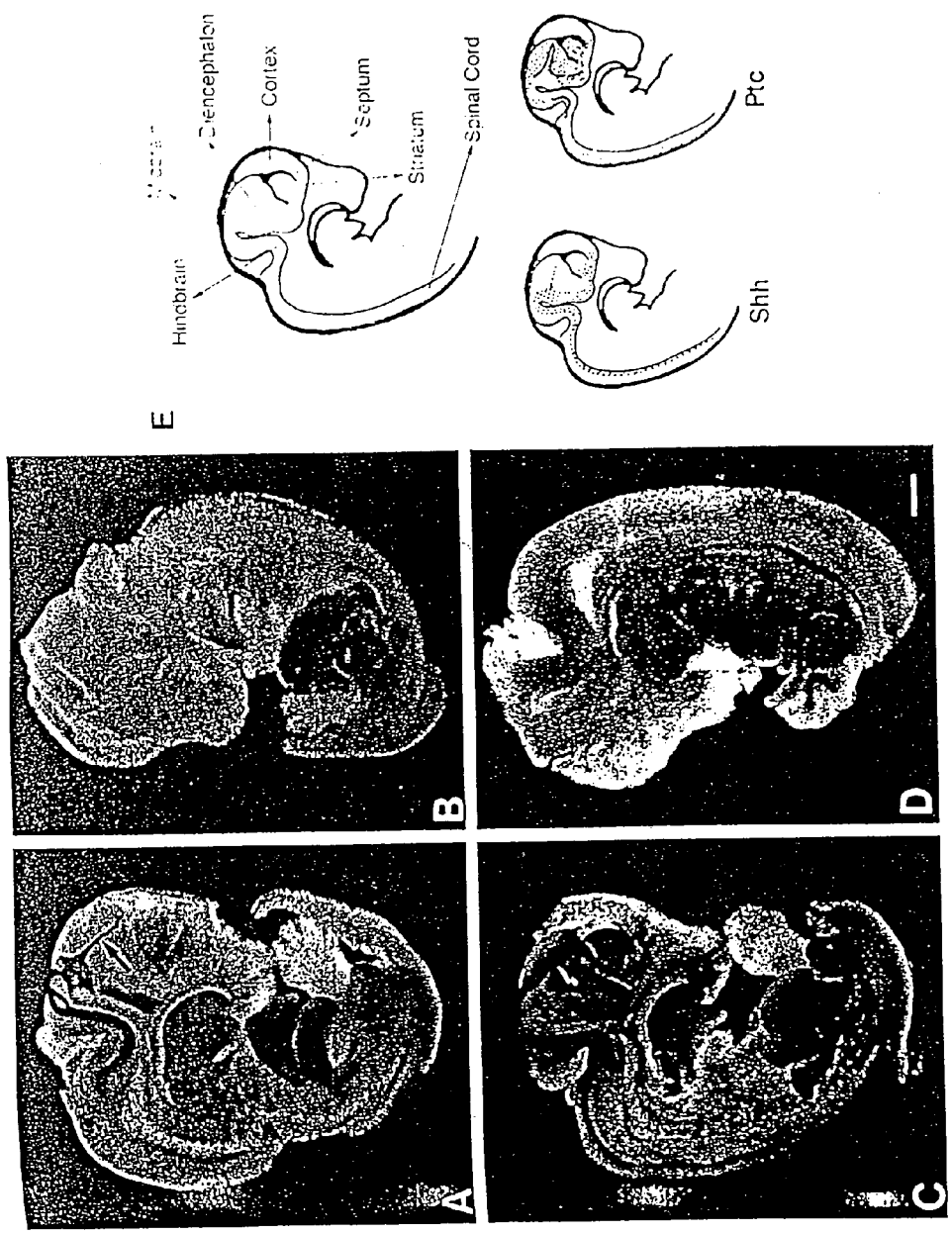
FIG. 1. Shh and Ptc in the E14.5 rat embryo. Shh (A, antisense; B, sense control), and ptc (C, antisense; D, sense control) expression as detected by in situ hybridization with digoxigenin-labeled riboprobes and alkaline phosphatase-conjugated anti-digoxigenin. The arrow in A and the double-arrow in C designate the zona limitan intrathalamica. Major anatomical structures and summary diagrams of shh and ptc expression are shown in E. Scale bar=1 mm.

Sonic hedgehog (Shh), an axis-determining secreted protein, is expressed during early vertebrate embryogenesis in the notochord and ventral neural tube. In this site it plays a role in the phenotypic specification of ventral neurons along the length of the CNS. For example, Shh induces the differentiation of motor neurons in the spinal cord and dopaminergic neurons in the midbrain. Shh expression, however, persists beyond this induction period. We have show here that Shh possesses novel activities beyond phenotype specification. Using cultures derived from the embryonic day 14.5 (E14.5) rat ventral mesencephalon, we show that Shh is also trophic for dopaminergic neurons. Interestingly, Shh not only promotes dopaminergic neuron survival, but also promotes the survival of midbrain GABA-immunoreactive (GABA-ir) neurons. In cultures derived from the E15–16 striatum, Shh promotes the survival of GABA-ir interneurons to the exclusion of any other cell type. Cultures derived from E15–16 ventral spinal cord reveal that Shh is again trophic for interneurons, many of which are GABA-ir and some of which express the Lim-½ nuclear marker, but does not appear to support motorneuron survival. Shh does not support survival of sympathetic or dorsal root ganglion neurons. Finally, using the midbrain cultures, we show that in the presence of MPP+, a highly specific neurotoxin, Shh prevents dopaminergic neuron death that normally would have occurred.

Based in part on these findings, we have determined that Shh, and other forms of hedgehog proteins, are useful as a protective agents in the treatment and prophylaxis for neurodegenerative disorders, particularly those resulting from the loss of dopaminergic and/or GABA-nergic neurons, or the general loss tissue from the substantia nigra. As described with greater detail below, exemplary disorders ("candidate disorders") include Parkinson's disease, Huntington's disease, amyotrophic lateral sclerosis and the like.

The subject invention also utilizies hedgehog or hedgehog agonists as cell culture additives for the maintenance of differentiated neurons in cultures, e.g., in cultures of dopaminergic and GABA-nergic neurons. The subject methods and compositions can also be used to augment the implantion of such neuronal cells in an animal.

In terms of treatment, once a patient experiences symptoms of a candidate disorder, a goal of therapy is prevention of further loss of neuron function.

I. Overview

The present application is directed to compositions and methods for the prevention and treatment of ischemic injury to the brain, such as resulting from stroke. The invention derives, at least in part, from the observation of a protective effect by the so called "hedgehog" proteins on animal stroke models. Briefly, as described in the appended examples, we investigated the neuroprotective potential of hedgehog proteins in a rat model of focal cerebral ischemia that used permanent occlusion of the middle cerebral artery. Intravenous infusion of vehicle (control) or Shh (sonic hedgehog) was administered for 3 hours beginning 30 minutes after occlusion, and resulted in a 70 percent reduction in total infarct size (P=0.0039), relative to the control, when examined 24 hours post-occlusion. Measurements of arterial blood pressure, blood gases, glucose, hematocrit and osmolality revealed no difference among vehicle- and Shh-treated animals. These results show that the intravenous hedgehog protein reduces neuronal damage due to stroke.

In one aspect, the present invention provides pharmaceutical preparations and methods for preventing/treating cerebral ischemia and the like utilizing, as an active ingredient, a hedgehog polypeptide or a mimetic thereof.

The subject hedgehog treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

However, without wishing to be bound by any particular theory, the reduction in infarct size in the present studies may be due at least in part to the ability of hedgehog proteins to antagonize (directly or indirectly) patched-mediated regulation of gene expression and other physiological effects mediated by the patched gene. The patched gene product, a cell surface protein, is understood to signal through a pathway which regulates transcription of a variety of genes involved in neuronal cell development. In the CNS and other tissue, the introduction of hedgehog relieves (derepresses) this inhibition conferred by patched, allowing expression of particular gene programs.

Accordingly, the present invention contemplates the use of other agents which are capable of mimicking the effect of the hedgehog protein on patched signalling, e.g., as may be identified from the drug screening assays described below.

II. Definitions

For convience, certain terms employed in the specfication, examples, and appended claims are collected here.

The term "hedgehog therapeutic" refers to various forms of hedgehog polypeptides, as well as peptidomimetics, which are neuroprotective for neuronal cells, and in particular, enhance the survival of dopaminergic and GABA-ergic neurons. These include naturally occurring forms of hedgehog proteins, as well as modified or mutant forms generated by molecular biological techniques, chemical synthesis, etc. While in preferred embodiments the hedgehog polypeptide is derived from a vertebrate homolog, cross-sepcies activity reported in the literature supports the use of hedgehog peolypeptides from invertebrate organisms as well. Naturally and non-naturally occurring hedgehog therapeutics referred to herein as "agonists" mimic or potentiate (collectively "agonize") the effects of a naturally-occurring hedgehog protein as a neuroprotective agent. In addition, the term "hedgehog therapeutic" includes molecules which can activate expression of an endogenous hedgehog gene. The term also includes gene therapy constructs for causing expression of hedgehog polypeptides in vivo, as for example, expression constructs encoding recombinant hedgehog polypeptides as well as trans-activation constructs for altering the regulatory sequences of an endogenous hedgehog gene by homologous recombination.

In particular, the term "hedgehog polypeptide" encompasses hedgehog proteins and peptidyl fragments thereof.

As used herein the term "bioactive fragment", with reference to a portions of hedgehog proteins, refers to a fragment of a full-length hedgehog protein, wherein the fragment specifically agonizes neuroprotective events mediated by wild-type hedgehog proteins. The hedgehog bioactive fragment preferably is a soluble extracellular portion of a hedgehog protein, where solubility is with reference to physiologically compatible solutions. Exemplary bioactive fragments are described in PCT publications WO 95/18856 and WO 96/17924.

The term "ptc therapeutic" refers to agents which mimic the effect of naturally occurring hedgehog proteins on patched signalling. The ptc therapeutic can be, e.g., a peptide, a nucleic acid, a carbohydrate, a small organic molecule, or natural product extract (or fraction thereof).

A "patient" or "subject" to be treated by the subject method are mammals, including humans.

An "effective amount" of, e.g., a hedgehog or ptc therapeutic, with respect to the subject method of treatment, refers to an amount of the therapeutic in a preparation which, when applied as part of a desired dosage regimen causes a increase in survival of a neuronal cell population according to clinically acceptable standards for the treatment or prevention of a particular disorder.

By "prevent degeneration" it is meant reduction in the loss of cells (such as from apoptosis), or reduction in impairment of cell function, e.g., release of dopamine in the case of dopaminergic neurons.

A "trophic factor", referring to a hedgehog or ptc therapeutic, is a molecule that directly or indirectly affects the survival or function of a hedgehog-responsive cell, e.g., a dopaminergic or GABAergic cell.

A "trophic amount" of a a hedgehog or ptc therapeutic is an amount sufficient to, under the circumstances, cause an increase in the rate of survival or the functional perfomance of a hedgehog-responsive cell, e.g., a dopaminergic or GABAergic cell.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be refered to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with an AR sequence of the present invention.

The term "corresponds to", when referring to a particular polypeptide or nucleic acid sequence is meant to indicate that the sequence of interest is identical or homologous to the reference sequence to which it is said to correspond.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$-$(hh)_m$-$(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

As used herein, the term "vector" refers to a nucleic acid molecule capable of transporting another nucleic acid to which it has been linked. The term "expression vector" includes plasmids, cosmids or phages capable of synthesizing, for example, the subject hedgehog polypeptides encoded by the respective recombinant gene carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein (or antisense) coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "operably linked" refers to the arrangement of a transcriptional regulatory element relative to other transcribable nucleic acid sequence such that the transcriptional regulatory element can regulate the rate of transcription from the transcribable sequence(s).

III. Exemplary Applications of Method and Compositions

One aspect of the present invention relates to a method of maintaining a differentiated state, e.g., enhancing survival, of a neuronal cell responsive to a hedgehog protein, by contacting the cells with a trophic amount of a hedgehog or ptc thereapeutic. For instance, it is contemplated by the invention that, in light of the present finding of an apparently trophic effect of hedgehog proteins in the maintenance of differentiated neurons, the subject method could be used to maintain different neuronal tissue both in vitro and in vivo. Where the trophic agent is a hedgehog protein, it can be provided to a cell culture or animal as a purified protein or secreted by a recombinant cell, or cells or tissue explants which naturally produce one or more hedgehog proteins. For instance, neural tube explants from embryos, particularly Doorplate tissue, can provide a source for Shh polypeptide, which source can be implanted in a patient or otherwise provided, as appropriate, for maintenance of differentiation.

The present method is applicable to cell culture techniques. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain dopaminergic and GABAergic cells in differentiated states, and can be employed, for instance, in cell cultures designed to test the specific activities of other trophic factors.

In such embodiments of the subject method, a culture of differentiated cells inlcuding dopaminergic and/or GABAergic cells can be contacted with a hedgehog or ptc therapeutic in order to maintain the integrity of a culture of terminally-differentiated neuronal cells by preventing loss of differentiation. The source of hedgehog or ptc therapeutic in the culture can be derived from, for example, a purified or semi-purified protein composition added directly to the cell culture media, or alternatively, supported and/or released from a polymeric device which supports the growth of various neuronal cells and which has been doped with the protein. The source of, for example, a trophic hedgehog polypeptide can also be a cell that is co-cultured with the neuronal cells. Alternatively, the source can be the neuronal cell itself which has been engineered to produce a recombinant hedgehog protein. Such neuronal cultures can be used as convenient assay systems as well as sources of implantable cells for therapeutic treatments.

The subject method can be used in conjunction with agents which induce the differentiation of neuronal precursors, e.g., progenitor or stem cells, into dopaminergic or GABAergic neurons.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially humans and non-human primates, pigs, cows, and rodents.

Intracerebral neural grafting has emerged recently as an additional potential to CNS therapy. For example, one approach to repairing damaged brain tissues involves the transplantation of cells from fetal or neonatal animals into the adult brain (Dunnett et al. (1987) *J Exp Biol* 123: 265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. Transplantation of fetal brain cells, which contain precursors of the dopaminergic neurons, has been examined with success as a treatment for Parkinson's disease. In animal models and in patients with this disease, fetal brain cell transplantations have resulted in the reduction of motor abnormalities. Furthermore, it appears that the implanted fetal dopaminergic neurons form synapses with surrounding host neurons. However, in the art, the transplantation of fetal brain cells is limited due, for example, to the limited survival time of the implanted neuronal precursors and differentiated neurons arising therefrom. The subject invention provides a means for extending the usefulness of such transplants by enhancing the survival of dopaminergic and/or GABAergic cells in the transplant.

In the specific case of Parkinson's disease, intervention by increasing the activity of hedgehog, by ectopic or endogenous means, can improve the in vivo survival of fetal and adult dopaminergic neurons, and thus can provide a more effective treatment of this disease. Cells to be transplanted for the treatment of a particular disease can be genetically modified in vitro so as to increase the expression of hedgehog in the transplant. In an exemplary embodiment of the invention, administration of an Shh polypeptide can be used in conjunction with surgical implantation of tissue in the treatment of Parkinson's disease.

In the case of a heterologous donor animal, the animal may be euthanized, and the brain and specific area of interest removed using a sterile procedure. Brain areas of particular interest include any area from which progenitor cells can be obtained which will provide dopaminergic or GABAergic cells upon differentiation. These regions include areas of the central nervous system (CNS) including the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, such as during epilepsy surgery.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6–8, more preferably close to pH 7, even more particularly about pH 7.4. Cells should be cultured at a temperature close to physiological temperature, preferably between 30° C.–40° C., more preferably between 32° C.–38° C., and most preferably between 35° C.–37° C.

Cells can be grown in suspension or on a fixed substrate, but proliferation of the progenitors is preferably done in suspension to generate large numbers of cells by formation of "neurospheres" (see, for example, Reynolds et al. (1992) *Science* 255:1070–1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3–4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3–10 days in vitro, the proliferating clusters (neurospheres) are fed every 2–7 days, and more particularly every 2–4 days by gentle centrifugation and resuspension in medium containing growth factor.

After 6–7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be induced by plating (or resuspending) the cells in the presence of a factor capable of sustaining differentiation, e.g., such as a hedgehog or ptc therapeutic of the present invention.

Stem cells useful in the present invention are generally known. For example, several neural crest cells have been identified, some of which are multipotent and likely represent uncommitted neural crest cells. The role of hedgehog proteins employed in the present method to culture such stem cells is to maintain differentiation a committed progenitor cell and/or a terminally-differentiated dopaminergic or GABAergic neuronal cell. The hedgehog protein can be used alone, or can be used in combination with other neurotrophic factors which act to more particularly enhance a particular differentiation fate of the neuronal progenitor cell.

In addition to the implantation of cells cultured in the presence of a functional hedgehog activity and other in vitro uses described above, yet another aspect of the present invention concerns the therapeutic application of a hedgehog or ptc therapeutic to enhance survival of dopaminergic and GABAergic neurons in vivo. The ability of hedgehog protein to maintain dopaminergic and GABAergic neuronal differentiation indicates that certain of the hedgehog proteins can be reasonably expected to facilitate control of of these neuronal cell-types in adult tissue with regard to maintenance, functional performance, aging and prevention of degeneration and premature death which result from loss of differentiation in certain pathological conditions. In light of this understanding, the present invention specifically contemplates applications of the subject method to the treatment of (prevention and/or reduction of the severity of) neurological conditions deriving from (i) loss of dopaminergic cells, (ii) loss of GABAergic cells, and/or (iii) loss of neurons of the substantia nigra. In this regard, the subject method is useful in the treatment of chronic neurodegenerative diseases of the nervous system, including Parkinson's disease, Huntington's chorea, amylotrophic lateral sclerosis and the like.

Many neurological disorders are associated with degeneration of discrete populations of neuronal elements and may be treatable with a therapeutic regimen which includes a hedgehog or ptc therapeutic according to the subject invention. As described in the appended examples, hedgehog exerts trophic and survival-promoting actions on substantia nigra dopaminergic neurons. In vivo, treatment with exogenous hedgehog, or other compounds of the present invention, is expected to stimulate the dopaminergic phenotype of substantia nigra neurons and restores functional deficits induced by axotomy or dopaminergic neurotoxins, and may be used the treatment of Parkinson's disease, a neurodegenerative disease characterized by the loss of dopaminergic neurons. Thus, in one embodiment, the subject method comprises administering to an animal afflected with Parkinson's disease, or at risk of developing Parkonson's disease, an amount of a hedgehog or ptc therapeutic effective for increasing the rate of survival of dopaminergic neurons in the animal. In preferred embodiments, the method includes administering to the animal an amount of a hedgehog or ptc therapeutic which would otherwise be effective at protecting the substantia nigra from MPTP-mediated toxicity when MPTP is administered at a dose of 0.5mg/kg, more preferably at a dose of 2 mg/kg, 5 mg/kg, 10 mg/kg, 20 mg/kg or 50 mg/kg and, more preferably, at a dose of 100 mg/kg.

Huntington's disease involves the degeneration of intrastriatal and cortical cholinergic neurons and GABAergic neurons. Treatment of patients suffering from such degenerative conditions can include the application of hedgehog or ptc therapeutics of the present invention, in order to control, for example, apoptotic events which give rise to loss of GABAergic neurons (e.g. to enhance survival of existing neurons.

Recently it has been reported that in certain ALS patients and animal models a significant loss of midbrain dopaminergic neurons occurs in addition to the loss of spinal motor neurons. For instance, the literature describes degeneration of the substantia nigra in some patients with familial amyotrophic lateral sclerosis. Kostic et al. (1997) *Ann Neurol* 41:497–504. According the subject invention, a trophic amount of a hedgehog or ptc therapeutic can be administered to an animal suffering from, or at risk of developing, ALS.

In general, the therapeutic method of the present invention can be characterized as including a step of administering to an animal an amount of a ptc or hedgehog therapeutic effective to enhance the survival of a dopaminergic and/or GABAergic neuronal cells. The mode of administration and dosage regimens will vary depending on the severity of the degenerative disoder being treated, e.g., the dosage may be altered as between a prophylaxis and treatment. In preferred embodiments, the ptc or hedeghog therapeutic is administered systemically initially, then locally for medium to long term care. In certain embodiments, a source of a hedgehog or ptc therapeutic is stereotactically provided within or proximate the area of degeneration.

The subject method may also find particular utility in treating or preventing the adverse neurological consequences of surgery. For example, certain cranial surgery can result in degeneration of neuronal populations for which the subject method can be applied.

In other embodiments, the subject method can be used to prevent or treat neurodegenerative conditions arising from the use of certain drugs, such as the compound MPTP (1-methyl-4-phenyl-1,2,3,6-tetrahydropyridine).

In still other embodiments, the subject method can be used in the prevention and/or treatment of hypoxia, e.g., as a neuroprotective agent. For instance, the subject method can be used prophylactically to lessen the neuronal cell death caused by altitude-induced hypoxia.

A method which is "neuroprotective", in the case of dopaminergic and GABAergic cells, results in diminished loss of cells of those phenotype relative to that which would occur in the absence of treatment with a hedgehog or ptc therapeutic.

In yet other embodiments, the subject method can be carried out conjointly with the administration of growth and/or trophic factors. For instance, the combinatorial therapy can include a trophic factor such as nerve growth factor, cilliary neurotrophic growth factor, schwanoma-derived growth factor, glial growth factor, striatal-derived neuronotrophic factor, platelet-derived growth factor, and scatter factor (HGF-SF). Antimitogenic agents can also be used, as for example, cytosine, arabinoside, 5-fluorouracil, hydroxyurea, and methotrexate.

Determination of a therapeutically effective amount and a prophylactically effective amount of a hedgehog or ptc therapeutic, e.g., to be adequately neuroprotective, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated, the risk of further degeneration to the CNS, and the particular agent being employed. In determining the therapeutically effective trophic amount or dose, and the prophylactically effective amount or dose, a number of factors are considered by the attending clinician, including, but not limited to: the specific cause of the degenerative state and its likelihood of recurring or worsening; pharmacodynamic characteristics of the particular agent and its mode and route of administration; the desirder time course of treatment; the species of mammal; its size, age, and general health; the response of the individual patient; the particular compound administered; the bioavailability characteristics of the preparation administered; the dose regimen selected; the kind of concurrent treatment (i.e., the interaction of the hedgehog or ptc therapeutic with other co-administered therapeutics); and other relevant circumstances.

Treatment can be initiated with smaller dosages which are less than the optimum dose of the agent. Thereafter, the dosage should be increased by small increments until the optimum effect under the circumstances is reached. For convenience, the total daily dosage may be divided and administered in portions during the day if desired. A therapeutically effective trophic amount and a prophylactically effective neuroprotective amount of a hedgehog polypeptide, for instance, is expected to vary from concentrations about 0.1 nanogram per kilogram of body weight per day (ng/kg/day) to about 100 mg/kg/day.

Potential hedgehog and ptc therapeutics, such as described below, can be tested by any of number of well known animal disease models. For instance, regarding Parkinson's Disease, selected agents can be evaluated in animals treated with MPTP. The compound MPTP (1-methyl-4-phenyl-1,2,3,6-tetrahydropyridine) and its metabolite $MPP^+$ have been used to induce experimental parkinsonism. $MPP^+$ kills dopaminergic neurons in the substantia nigra, yielding a reasonable model of late parkinsonism. Turski et al., (1991) *Nature* 349:414.

Compounds which are determined to be effective for the prevention or treatment of degeneration of dopaminergic and GABAergic neurons and the like in animals, e.g., dogs, rodents, may also be useful in treatment of disorders in humans. Those skilled in the art of treating in such disorders in humans will be guided, from the data obtained in animal studies, to the correct dosage and route of administration of the compound to humans. In general, the determination of dosage and route of administration in humans is expected to be similar to that used to determine administration in animals.

The identification of those patients who are in need of prophylactic treatment for disorders marked by degeneration of dopaminergic and/or GABAergic neurons is well within the ability and knowledge of one skilled in the art. Certain of the methods for identification of patients which are at risk and which can be treated by the subject method are appreciated in the medical arts, such as family history of the development of a particular disease state and the presence of risk factors associated with the development of that disease state in the subject patient. A clinician skilled in the art can readily identify such candidate patients, by the use of, for example, clinical tests, physical examination and medical/family history.

IV. Exemplary Hedgehog Therapeutic Compounds.

The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The various naturally-occurring hedgehog proteins from which the subject therapeutics can be derived are characterized by a signal peptide, a highly conserved N-terminal region, and a more divergent C-terminal domain. In addition to signal sequence cleavage in the secretory pathway (Lee, J. J. et al. (1992) *Cell* 71:33–50; Tabata, T. et al. (1992) *Genes Dev.* 2635–2645; Chang, D. E. et al. (1994) *Development* 120:3339–3353), hedgehog precursor proteins naturally undergo an internal autoproteolytic cleavage which depends on conserved sequences in the C-terminal portion (Lee et al. (1994) *Science* 266:1528–1537; Porter et al. (1995) *Nature* 374:363–366). This autocleavage leads to a 19 kD N-terminal peptide and a C-terminal peptide of 26–28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15:2294–2303; Porter et al. (1995) supra; Ekker, S. C. et al. (1995) *Curr. Biol.* 5:944–955; Lai, C. J. et al. (1995) *Development* 121:2349–2360). The N-terminal peptide stays tightly associated with the surface of cells in which it was synthesized, while the C-terminal peptide is freely diffusible both in vitro and in vivo (Lee et al. (1994) supra; Bumcrot et al. (1995) supra; Mart', E. et al. (1995) *Development* 121:2537–2547; Roelink, H. et al. (1995) *Cell* 81:445–455). Cell surface retention of the N-terminal peptide is dependent on autocleavage, as a truncated form of hedgehog encoded by an RNA which terminates precisely at the normal position of internal cleavage is diffusible in vitro (Porter et al. (1995) supra) and in vivo (Porter, J. A. et al. (1996) *Cell* 86, 21–34). Biochemical studies have shown that the autoproteolytic cleavage of the hedgehog precursor protein proceeds through an internal thioester intermediate which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

The vertebrate family of hedgehog genes includes at least four members, e.g., paralogs of the single drosophila hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No:1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; a human Dhh polypeptide is encoded by SEQ ID No. 8; and a zebrafish Thh is encoded by SEQ ID No. 9.

TABLE 1

Guide to hedgehog sequences in Sequence Listing

|  | Nucleotide | Amino Acid |
| --- | --- | --- |
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| Zebrafish Thh | SEQ ID No. 9 | SEQ ID No. 18 |
| Drosophila HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein. In addition to proteolytic fragmentation, the vertebrate hedgehog proteins can also be modified post-translationally, such as by glycosylation and/or addition of cholesterol, though bacterially produced (e.g. unglycosylated/uncholesterolized) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

In one embodiment, the hedgehog therapeutic is a polypeptide encodable by a nucleotide sequence that hybridizes under stringent conditions to a hedgehog coding sequence represented in one or more of SEQ ID Nos:1–9 or 19. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2× SSC at 50°C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from mRNA or genomic DNA samples using techniques well known in the art. For example, a cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Preferred nucleic acids encode a hedgehog polypeptide comprising an amino acid sequence at least 60% homologous, more preferably 70% homologous and most preferably 80% homologous with an amino acid sequence selected from the group consisting of SEQ ID Nos:8–14. Nucleic acids which encode polypeptides at least about 90%, more preferably at least about 95%, and most preferably at least about 98–99% homology with an amino acid sequence represented in one of SEQ ID Nos:10–18 or 20 are also within the scope of the invention.

Hedgehog polypeptides preferred by the present invention, in addition to native hedgehog proteins, are at least 60% homologous, more preferably 70% homologous and most preferably 80% homologous with an amino acid sequence represented by any of SEQ ID Nos: 10–18 or 20. Polypeptides which are at least 90%, more preferably at least 95%, and most preferably at least about 98–99% homologous with a sequence selected from the group consisting of SEQ ID Nos:10–18 or 20 are also within the scope of the invention. The only prerequisite is that the hedgehog polypeptide is capable of protecting neuronal cells against degeneration, e.g., the polypeptide is trophic for a dopaminergic and/or GABAergic neuron.

The term "recombinant protein" refers to a polypeptide of the present invention which is produced by recombinant DNA techniques, wherein generally, DNA encoding a hedgehog polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein" those proteins having an amino acid sequence of a native hedgehog protein, or an amino acid sequence similar thereto which is generated by mutations including substitutions and deletions (including truncation) of a naturally occurring form of the protein.

The method of the present invention can also be carried out using variant forms of the naturally occurring hedgehog polypeptides, e.g., mutational variants.

As is known in the art, hedgehog polypeptides can be produced by standard biological techniques. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ IDNos:1–9or 19.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a hedgehog protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing hedgehog-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-S-transferase (GST-fusion) proteins. Such GST-fusion proteins can enable easy purification of the hedgehog polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g. of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309:30–3; and Kornblihtt et al. (1985) *EMBO* 4:1755–9) can be added to the hedgehog polypeptide to support attachment of the chimeric molecule to a cell through binding ECM components (Ruoslahti et al. (1987) *Science* 238:491–497; Pierschbacher et al. (1987) *J. Biol. Chem.* 262:17294–8.; Hynes (1987) Cell 48:549–54; and Hynes (1992) *Cell* 69:11–25).

In preferred embodiment, the hedgehog polypeptide is isolated from, or is otherwise substantially free of, other cellular proteins, especially other extracellular or cell surface associated proteins which may normally be associated with the hedgehog polypeptide. The term "substantially free of other cellular or extracellular proteins" (also referred to herein as "contaminating proteins") or "substantially pure or purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID Nos:10–18 or 20, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioctive fragments of hedgehog polypeptide, preferred hedgehog therapeutics include at least 50 amino acid residues of a hedgehog polypeptide, more preferably at least 100, and even more preferably at least 150.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24–197 of SEQ ID No. 15, 28–202 of SEQ ID No. 16, and 23–198 of SEQ ID No. 17. By "corresponding approximately" it is meant that the sequence of interest is at most 20 amino acid residues different in length to the reference sequence, though more preferably at most 5, 10 or 15 amino acid different in length.

Still other preferred hedgehog polypeptides includes an amino acid sequence represented by the formula A-B wherein: (i) A represents all or the portion of the amino acid sequence designated by residues 1–168 of SEQ ID No:21; and B represents at least one amino acid residue of the amino acid sequence designated by residues 169–221 of SEQ ID No:21; (ii) A represents all or the portion of the amino acid sequence designated by residues 24–193 of SEQ ID No:15; and B represents at least one amino acid residue of the amino acid sequence designated by residues 194–250 of SEQ ID No:15; (iii) A represents all or the portion of the amino acid sequence designated by residues 25–193 of SEQ ID No:13; and B represents at least one amino acid residue of the amino acid sequence designated by residues 194–250 of SEQ ID No:13; (iv) A represents all or the portion of the amino acid sequence designated by residues 23–193 of SEQ ID No:11; and B represents at least one amino acid residue of the amino acid sequence designated by residues 194–250 of SEQ ID No:11; (v) A represents all or the portion of the amino acid sequence designated by residues 28–197 of SEQ ID No:12; and B represents at least one amino acid residue of the amino acid sequence designated by residues 198–250 of SEQ ID No:12; (vi) A represents all or the portion of the amino acid sequence designated by residues 29–197 of SEQ ID No:16; and B represents at least one amino acid residue of the amino acid sequence designated by residues 198–250 of SEQ ID No:16; or (vii) A represents all or the portion of the amino acid sequence designated by residues 23–193 of SEQ ID No. 17, and B represents at least one amino acid residue of the amino acid sequence designated by residues 194–250 of SEQ ID No. 17. In certain preferred embodiments, A and B together represent a contiguous polypeptide sequence designated sequence, A represents at least 25, 50, 75, 100, 125 or 150 amino acids of the designated sequence, and B represents at least 5, 10, or 20 amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above.

Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as agonists of a wild-type (e.g., "authentic") hedgehog protein. For example, Roman et al. (1994) *Eur J Biochem* 222:65–73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack glycosylation sites (e.g. to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that certain isolated replacements of amino acids, e.g., replacement of an amino acid residue with another related amino acid (i.e. isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic = aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, WH Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried using homologs of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g. homologs) that are functional in binding to a receptor for hedgehog proteins. The purpose of screening such combinatorial libraries is to generate, for example, novel hedgehog homologs which can act as neuroprotective agents. To illustrate, hedgehog homologs can be engineered by the present method to provide more efficient binding to a cognate receptor, such as patched, retaining neuroprotective activity. Thus, combinatorially-derived homologs can be generated to have an increased potency relative to a naturally occurring form of the protein. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) *J Med Chem* 37:1233 describes the general state of the art of combinatorial libraries as of the earlier 1990's. In particular, Gallop et al state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins: Structure, Function and Genetics* 8:309–314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high through-out analysis that removes any requirement of a priori understanding or knowledge of critical residues.

To illsutrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

```
C-G-P-G-R-G-X(1)-G-X(2)-R-R-H-P-K-K-L-T-P-L-A-Y-K-Q-F-I-P-N-V-A-E-      (SEQ ID No: 21)
K-T-L-G-A-S-G-R-Y-E-G-K-I-X(3)-R-N-S-E-R-F-K-E-L-T-P-N-Y-N-P-D-I-I-F-

K-D-E-E-N-T-G-A-D-R-L-M-T-Q-R-C-K-D-K-L-N-X(4)-L-A-I-S-V-M-N-X(5)-

W-P-G-V-X(6)-L-R-V-T-E-G-W-D-E-D-G-H-H-X(7)-E-E-S-L-H-Y-E-G-R-A-

V-D-I-T-T-S-D-R-D-X(8)-S-K-Y-G-X(9)-L-X(10)-R-L-A-V-E-A-G-F-D-W-V-
Y-Y-E-S-K-A-H-I-H-C-S-V-K-A-E-N-S-V-A-A-K-S-G-G-C-F-P-G-S-A-X(11)-
V-X(12)-L-X(13)-X(14)-G-G-X(15)-K-X-(16)-V-K-D-L-X(17)-P-G-D-X(18)-V-
L-A-A-D-X(19)-X(20)-G-X(21)-L-X(22)-X(23)-S-D-F-X(24)-X(25)-F-X(26)-D-
R,
``` wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp ; Xaa(2) represents Arg, Thr, His or Trp; Xaa(24) represents Ile, Val, Leu or Met; Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

```
C-G-P-G-R-G-X(1)-X(2)-X(3)-R-R-X(4)-X(5)-X(6)-P-K-X(7)-L-X(8)-P-L-X(9)-   (SEQ ID No: 22)
Y-K-Q-F-X(10)-P-X(11)-X(12)-X(13)-E-X(14)-T-L-G-A-S-G-X(15)-X(16)-E-G-
X(17)-X(18)-X(19)-R-X(20)-S-E-R-F-X(21)-X(22)-L-T-P-N-Y-N-P-D-I-I-F-K-
D-E-E-N-X(23)-G-A-D-R-L-M-T-X(24)-R-C-K-X(25)-X(26)-X(27)-N-X(28)-L-
A-I-S-V-M-N-X(29)-W-P-G-V-X(30)-L-R-V-T-E-G-X(31)-D-E-D-G-H-H-
X(32)-X(33)-X(34)-S-L-H-Y-E-G-R-A-X(35)-D-I-T-T-S-D-R-D-X(36)-X(37)-K-
Y-G-X(38)-L-X(39)-R-L-A-V-E-A-G-F-D-W-V-Y-Y-E-S-X(40)-X(41)-H-X(42)-
H-X(43)-S-V-K-X(44)-X(45),
```

His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gln; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gln, Asn, Glu, or Asp; Xaa(14) represents His, Phe, Tyr, Thr, Gln, Asn, Glu or Asp; Xaa(15) represents Gln, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gln, Ser, Thr or Cys; Xaa(18) represents Arg, Lys, Met or Ile; Xaa(1 9) represents Ala, Gly, Cys, Asp, Glu, Gln, Asn, Ser, Thr or Met; Xaa(20) represents Ala, Gly, Cys, Asp, Asn, Glu or Gln; Xaa(21) represents Arg, Lys, Met, Ile, Asn, Asp, Glu or Gln; Xaa(22) represent Leu, Val, Met or Ile; Xaa(23) represents Phe, Tyr, wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gln, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr; Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gln; Xaa(21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gln, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gln, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gln, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gln, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g. the polypeptides of the library all include a signal sequence but no transmembrane or cytoplasmic domains), and is used to transfect a eukaryotic cell that can be co-cultured with neuronal cells. A functional hedgehog protein secreted by the cells expressing the combinatorial library will diffuse to neighboring neuronal cells and induce a particular biological response, such as protection against cell death when treated with MPTP. The pattern of protection will resemble a gradient function, and will allow the isolation (generally after several repetitive rounds of selection) of cells producing hedgehog homologs active as neuroprotective agents with respect to the target neuronal cells.

To illustrate, target neuronal cells are cultured in 24-well microtitre plates. Other eukaryotic cells are transfected with the combinatorial hedgehog gene library and cultured in cell culture inserts (e.g. Collaborative Biomedical Products, Catalog #40446) that are able to fit into the wells of the microtitre plate. The cell culture inserts are placed in the wells such that recombinant hedgehog homologs secreted by the cells in the insert can diffuse through the porous bottom of the insert and contact the target cells in the microtitre plate wells. After a period of time sufficient for functional forms of a hedgehog protein to produce a measurable response in the target cells, such as neuroprotection, the inserts are removed and the effect of the variant hedgehog proteins on the target cells determined. Cells from the inserts corresponding to wells which score positive for activity can be split and re-cultured on several inserts, the process being repeated until the active clones are identified.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening hedgehog combinatorial libraries. For instance, the pCANTAB 5 phagemid of the RPAS kit contains the gene which encodes the phage gIII coat protein. The hedgehog combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins which are capable of binding an hedgehog receptor are selected or enriched by panning. For instance, the phage library can be applied to cells which express the patched protein and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli,* and panning will greatly enrich for hedgehog homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature,* 2., In Maenner and Manderick, eds., Elsevir Publishing Co., Amsterdam, pp. 401–410; Delgrave et al., 1993, *Protein Engineering* 6(3):327–331).

The invention also provides for reduction of the hedgehog protein to generate mimetics, e.g. peptide or non-peptide agents, which are able to mimic the neuroprotective activity of a naturally-occurring hedgehog polypeptide. Thus, such mutagenic techniques as described above are also useful to map the determinants of the hedgehog proteins which participate in protein-protein interactions involved in, for example, binding of the subject hedgehog polypeptide to other extracellular matrix components such as its receptor (s). To illustrate, the critical residues of a subject hedgehog polypeptide which are involved in molecular recognition of an hedgehog receptor such as patched can be determined and used to generate hedgehog-derived peptidomimetics which competitively bind with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. After distinguishing between agonist and antagonists, such agonistic mimetics may be used to mimic the normal function of a hedgehog protein as trophic for dopaminergic and GABAergic neurons. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Recombinantly produced forms of the hedgehog proteins can be produced using, e.g, expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either a neuroprotective form of a hedgehog polypeptide. Thus, another aspect of the invention features expression vectors for in vivo transfection of a hedgehog polypeptide in particular cell types so as cause ectopic expression of a hedgehog polypeptide in neuronal tissue.

Formulations of such expression constructs may be administered in any biologically effective carrier, e.g. any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including neuronal cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO 93/25234 and WO 94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including neuronal cells (Rosenfeld et al. (1992) cited supra).

Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683;

Berkner et al., supra; and Graham et al. in *Methods in Molecular Biology*, E. J. Murray, Ed. (Humana, Clifton, N.J., 1991) vol. 7. pp. 109–127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A hedgehog expression construct can be delivered in a gene therapy construct to dermal cells by, e.g., electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the hedgehog or ptc therapeutic can be a "gene activation" construct which, by homologous recombination with a genomic DNA, alters the transcriptional regulatory sequences of an endogenous gene. For instance, the gene activation construct can replace the endogenous promoter of a hedgehog gene with a heterologous promoter, e.g., one which causes consitutive expression of the hedgehog gene or which causes inducible expression of the gene under conditions different from the normal expression pattern of the gene. Other genes in the patched signaling pathway can be similarly targeted. A vareity of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous hedgehog gene (exon sequence, intron sequence, promoter sequences, etc.) which direct recombination and (2) heterologous transcriptional regulatory sequence(s) which is to be operably linked to the coding sequence for the genomic hedgehog gene upon recombination of the gene activation construct. For use in generating cultures of hedgehog producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native hedgehog gene. Such insertion occurs by homologous recombination, i.e., recombination regions of the activation construct that are homologous to the endogenous hedgehog gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regualtory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, *J. Exp. Med.,* 169:13), the human β-actin promoter (Gunning et al. (1987) *PNAS* 84:4831–4835), the glucocorticoid-inducible promoter present in the mouse mammary tumor virus long terminal repeat (MMTV LTR) (Klessig et al. (1984) *Mol. Cell Biol.* 4:1354–1362), the long terminal repeat sequences of Moloney murine leukemia virus (MuLV LTR) (Weiss et al. (1985) *RNA Tumor Viruses*, Cold Spring Harbor Laboratory, Cold Spring Harbor, N.Y.), the SV40 early or late region promoter (Bemoist et al. (1981) *Nature* 290:304–310; Templeton et al. (1984) *Mol. Cell Biol.,* 4:817; and Sprague et al. (1983) *J. Virol.,* 45:773), the promoter contained in the 3' long terminal repeat of Rous sarcoma virus (RSV) (Yamamoto et al., 1980, *Cell,* 22:787–797), the herpes simplex virus (HSV) thymidine kinase promoter/enhancer (Wagner et al. (1981) *PNAS* 82:3567–71), and the herpes simplex virus LAT promoter (Wolfe et al. (1992) *Nature Genetics,* 1:379–384).

In an exemplary embodiment, portions of the 5' flanking region of the human Shh gene are amplified using primers which add restriction sites, to generate the following fragments 5'-gcgcgcttcgaaGCCAGCCAGCCAGCGAGGGAGAGAGCGAGCGGGCGAGCCGGAGC- GAGGAAatcgatgcgcgc (primer 1, SEQ ID No: 23)

5'-gcgcgcagatctGGGAAAGCGCAAGAGACAGCGCACACGCACACACCCGCCGCGCG-

CACTCGggatccgcgcgc (primer 2, SEQ ID No: 24)

As illustrated, primer 1 includes a 5' non-coding region of the human Shh gene and is flanked by an AsuII and ClaI restriction sites. Primer 2 includes a portion of the 5' non-coding region immediately 3' to that present in primer 1. The hedgehog gene sequence is flanked by XhoII and BamHI restriction sites. The purified amplimers are cut with each of the enzymes as appropriate.

The vector pCDNA1.1 (Invitrogen) includes a CMV promoter. The plasmid is cut with with AsuII, which cleaves just 3' to the CMV promoter sequence. The AsuI/ClaI fragment of primer 1 is ligated to the AsuII cleavage site of the pcDNA vector. The ClaI/AsuII ligation destroys the AsuII site at the 3' end of a properly inserted primer 1.

The vector is then cut with BamHI, and an XhoII/BamHI fragment of primer 2 is ligated to the BamHI cleavage site. As above, the BamHI/XhoII ligation destroys the BamHI site at the 5' end of a properly inserted primer 2.

Individual colonies are selected, cut with AsuII and BamHI, and the size of the AsuII/BamHI fragment determined. Colonies in which both the primer 1 and primer 2 sequences are correctly inserted are further amplified, an cut with AsuII and BamHI to produce the gene activation construct In this construct, the flanking primer 1 and primer 2 sequences provide the recombination region which permits the insertion of the CMV promoter in front of the coding sequence for the human Shh gene. Other heterologous promoters (or other transcriptional regulatory sequences) can be inserted in a genomic hedgehog gene by a similar method.

In still other embodiments, the replacement region merely deletes a negative transcriptional control element of the native gene, e.g., to activate expression, or ablates a positive control element, e.g., to inhibit expression of the targeted gene.

V. Exemplary ptc Therapeutic Compounds

In another embodiment, the subject method is carried out using a ptc therapeutic composition. Such compositions can be generated with, for example, compounds which bind to patched and alter its signal transduction activity, compounds which alter the binding and/or enzymatic activity of a protein (e.g., intracellular) involved in patched signal pathway, and compounds which alter the level of expression of a hedgehog protein, a patched protein or a protein involved in the intracellular signal transduction pathway of patched.

cgaagcgaggcagccagcgagggagagagcgagcgggcgagccggagcgaggaaATCGAACGTTC (SEQ ID No: 25)

GAATCCTTCCCCCACCACCATCACTTTCAAAAGTCCGAAAGAATCTGCTCCCTGCTTGTGTGTTG

GAGGTCGCTGAGTACTGCGCGAGTAAAATTTAAGCTACAACAAGGCAAGGCTTGACCGACAATTG

CATGAAGAATCTGCTTAGGGTTAGGCGTTTTGCGCTGCTTCGCGATGTACGGGCCAGATATACGC

GTTGACATTGATTATTGACTAGTTATTAATAGTAATCAATTACGGGTCATTAGTTCATAGCCCA

TATATGGAGTTCCGCGTTACATAACTTACGGTAAATGGCCCGCCTGGCTGACCGCCCAACGACCC

CCGCCCATTGACGTCAATAATGACGTATGTTCCCATAGTAACGCCAATAGGGACTTTCCATTGAC

GTCAATGGGTGGACTATTTACGGTAAACTGCCCACTTGGCAGTACATCAAGTGTATCATATGCCA

AGTACGCCCCCTATTGACGTCAATGACGGTAAATGGCCCGCCTGGCATTATGCCCAGTACATGAC

CTTATGGGACTTTCCTACTTGGCAGTACATCTACGTATTAGTCATCGCTATTACCATGGTGATGC

GGTTTTGCCAGTACATCAATGGGCGTGGATAGCGGTTTGACTCACCCGGATTTCCAAGTCTCCAC

CCCATTGACGTCAATGGGAGTTTGTTTTGGCACCAAAATCAACGGGACTTTCCAAAATGTCGTAA

CAACTCCGCCCCATTGACGCAAATGGGCGGTAGGCGTGTACGGTGGGAGGTCTATATAAGCAGAG

CTCTCTGGCTAACTAGAGAACCCACTGCTTACTGGCTTATCGAAATTAATACGACTCACTATAGG

GAGACCCAAGCTTGGTACCGAGCTCGGATCgatctgggaaagcgcaagagagagcgcacacgcac acacccgccgcgcgcactcgg The availability of purified and recombinant hedgehog polypeptides facilitates the generation of assay systems which can be used to screen for drugs, such as small organic molecules, which are either agonists or antagonists of the normal cellular function of a hedgehog and/or patched protein, particularly in their role in the pathogenesis of neuronal cell death. In one embodiment, the assay evaluates the ability of a compound to modulate binding between a hedgehog polypeptide and a hedgehog receptor such as patched. In other embodiments, the assay merely scores for the ability of a test compound to alter the signal transduction activity of the patched protein. In this manner, a variety of hedgehog and/or ptc therapeutics, which will include ones with neuroprotective activity, can be identified. A variety of assay formats will suffice and, in light of the present disclosure, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Accordingly, in an exemplary screening assay for ptc therapeutics, the compound of interest is contacted with a mixture including a hedgehog receptor protein (e.g., a cell expressing the patched receptor) and a hedgehog protein under conditions in which it is ordinarily capable of binding the hedgehog protein. To the mixture is then added a composition containing a test compound. Detection and quantification of receptor/hedgehog complexes provides a means for determining the test compound's efficacy at inhibiting (or potentiating) complex formation between the receptor protein and the hedgehog polypeptide. Moreover, a control assay can also be performed to provide a baseline for comparison. In the control assay, isolated and purified hedgehog polypeptide is added to the receptor protein, and the formation of receptor/hedgehog complex is quantitated in the absence of the test compound.

In other embodiments, a ptc therapeutic of the present invention is one which disrupts the association of patched with smoothened.

Agonist and antagonists of neuroprotection can be distinguished, and the efficacy of the compound can be assessed, by subsequent testing with neuronal cells.

In an illustrative embodiment, the polypeptide utilized as a hedgehog receptor can be generated from the patched protein. Accordingly, an exemplary screening assay includes all or a suitable portion of the patched protein which can be obtained from, for example, the human patched gene (GenBank U43148) or other vertebrate sources (see GenBank Accession numbers U40074 for chicken patched and U46155 for mouse patched), as well as from *drosophila* (GenBank Accession number M28999) or other invertebrate sources. The patched protein can be provided in the screening assay as a whole protein (preferably expressed on the surface of a cell), or alternatively as a fragment of the full length protein which binds to hedgehog polypeptides, e.g., as one or both of the substantial extracellular domains (e.g. corresponding to residues Asn120-Ser438 and/or Arg770-Trp1027 of the human patched protein). For instance, the patched protein can be provided in soluble form, as for example a preparation of one of the extracellular domains, or a preparation of both of the extracellular domains which are covalently connected by an unstructured linker (see, for example, Huston et al. (1988) *PNAS* 85:4879; and U.S. Pat. No. 5,091,513). In other embodiments, the protein can be provided as part of a liposomal preparation or expressed on the surface of a cell. The patched protein can derived from a recombinant gene, e.g., being ectopically expressed in a heterologous cell. For instance, the protein can be expressed on oocytes, mammalian cells (e.g., COS, CHO, 3T3 or the like), or yeast cell by standard recombinant DNA techniques. These recombinant cells can be used for receptor binding, signal transduction or gene expression assays. Marigo et al. (1996) *Development* 122:1225–1233 illustrates a binding assay of human hedgehog to chick patched protein ectopically expressed in *Xenopus laevis* oocytes. The assay system of Marigo et al. can be adapted to the present drug screening assays. As illustrated in that reference, Shh binds to the patched protein in a selective, saturable, dose-dependent manner, thus demonstrating that patched is a receptor for Shh.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, for cell-free assays, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide, e.g. an $^{35}$S-labeled hedgehog polypeptide, and the test compound and incubated under conditions conducive to complex formation, e.g. at physiological conditions for salt and pH, though slightly more stringent conditions may be desired. Following incubation, the beads are washed to remove any unbound hedgehog polypeptide, and the matrix bead-bound radiolabel determined directly (e.g. beads placed in scintillant), or in the supernatant after the receptor/hedgehog complexes are dissociated. Alternatively, the complexes can be dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g. paranitrophenylphosphate. Likewise, a fusion protein comprising the hedgehog polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the PFLAG system (International Biotechnologies, Inc.) or the pEZZ-protein A system (Pharamacia, N.J.).

Where the desired portion of the hedgehog receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g. phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262: 11369–11374).

In addition to cell-free assays, such as described above, the readily available source of hedgehog proteins provided by the art also facilitates the generation of cell-based assays for identifying small molecule agonists of the neuroprotective activity of wild-type hedgehog proteins. Analogous to the cell-based assays described above for screening combinatorial libraries, neuronal cells which are sensitive to hedgehog-dependent protection, such as dopaminergic and GABAergic neurons, can be contacted with a hedgehog protein and a test agent of interest, with the assay scoring for anything from simple binding to the cell to trophic responses by the target cell in the presence and absence of the test agent. As with the cell-free assays, agents which produce a statistically significant change in hedgehog activities (either inhibition or potentiation) can be identified.

In other emdodiments, the cell-based assay scores for agents which disrupt association of patched and smoothened proteins, e.g., in the cell surface membrane or liposomal preparation.

In addition to characterizing cells that naturally express the patched protein, cells which have been genetically engineered to ectopically express patched can be utilized for drug screening assays. As an example, cells which either express low levels or lack expression of the patched protein, e.g. *Xenopus laevis* oocytes, COS cells or yeast cells, can be genetically modified using standard techniques to ectopically express the patched protein. (see Marigo et al., supra).

The resulting recombinant cells, e.g., which express a functional patched receptor, can be utilized in receptor binding assays to identify agonist or anatagonsts of hedgehog binding. Binding assays can be performed using whole cells. Furthermore, the recombinant cells of the present invention can be engineered to include other heterolgous genes encoding proteins involved in hedgehog-dependent siganl pathways. For example, the gene products of one or more of smoothened, costal-2 and/or fused can be co-expressed with patched in the reagent cell, with assays being sensitive to the functional reconstituion of the hedgehog signal transduction cascade.

Alternatively, liposomal preparations using reconstituted patched protein can be utilized. Patched protein purified from detergent extracts from both authentic and recombinant origins can be reconstituted in in artificial lipid vesicles (e.g. phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262: 11369–11374). The lamellar structure and size of the resulting liposomes can be characterized using electron microscopy. External orientation of the patched protein in the reconstituted membranes can be demonstrated, for example, by immunoelectron microscopy. The hedgehog protein binding activity of liposomes containing patched and liposomes without the protein in the presence of candidate agents can be compared in order to identify potential modulators of the hedgehog-patched interaction.

The hedgehog protein used in these cell-based assays can be provided as a purified source (natural or recombinant in origin), or in the form of cells/tissue which express the protein and which are co-cultured with the target cells. As in the cell-free assays, where simple binding (rather than induction) is the hedgehog activity scored for in the assay, the protein can be labelled by any of the above-mentioned techniques, e.g., fluorescently, enzymatically or radioactively, or detected by immunoassay.

In addition to binding studies, functional assays can be used to identified modulators, i.e., agonists of hedgehog or patched activities. By detecting changes in intracellular signals, such as alterations in second messengers or gene expression in patched-expressing cells contacted with a test agent, candidate antagonists to patched signaling can be identified (e.g., having a hedgehog-like activity).

A number of gene products have been implicated in patched-mediated signal transduction, including patched, the transcription factor cubitus interruptus (ci), the serine/threonine kinase used (fu) and the gene products of costal-2, smoothened and suppressor of fused.

The interaction of a hedgehog protein with patched sets in motion a cascade involving the activation and inhibition of downstream effectors, the ultimate consequence of which is, in some instances, a detectable change in the transcription or translation of a gene. Potential transcriptional targets of patched signaling are the patched gene itself (Hidalgo and Ingham, 1990 *Development* 110, 291–301; Marigo et al., 1996) and the vertebrate homologs of the *drosophila* cubitus interruptus gene, the GLI genes (Hui et al. (1994) *Dev Biol* 162:402–413). Patched gene expression has been shown to be induced in cells of the limb bud and the neural plate that are responsive to Shh. (Marigo et al. (1996) *PNAS*, in press; Marigo et al. (1996) *Development* 122:1225–1233). The GLI genes encode putative transcription factors having zinc finger DNA binding domains (Orenic et al. (1990) *Genes & Dev* 4:1053–1067; Kinzler et al. (1990) *Mol Cell Biol* 10:634–642). Transcription of the GLI gene has been reported to be upregulated in response to hedgehog in limb buds, while transcription of the GLI3 gene is downregulated in response to hedgehog induction (Marigo et al. (1996) *Development* 122:1225–1233). By selecting transcriptional regulatory sequences from such target genes, e.g. from patched or GLI genes, that are responsible for the up- or down regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as antagonists of ptc, e.g., which may be useful as neuroprotective agents.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270:10314–10322; and Kube et al. (1995) *Cytokine* 7:1–7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsice to patched-dependent signalling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc therapeutic.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In yet other embodiments, second messenger generation can be measured directly in the detection step, such as mobilization of intracellular calcium, phospholipid metabolism or adenylate cyclase activity are quantitated, for instance, the products of phospholipid hydrolysis $IP_3$, DAG or cAMP could be measured For example, recent studies have implicated protein kinase A (PKA) as a possible component of hedgehog/patched signaling (Hammerschmidt et al. (1996) *Genes & Dev* 10:647). High PKA activity has been shown to antagonize hedgehog signaling in these systems. Conversely, inhibitors of PKA will mimic and/or potentiate the action of hedgehog. Although it is unclear whether PKA acts directly downstream or in parallel with hedgehog signaling, it is possible that hedgehog signalling occurs via inhibition of PKA activity. Thus, detection of PKA activity provides a potential readout for the instant assays.

In a preferred embodiment, the ptc therapeutic is a PKA inhibitor. A variety of PKA inhibitors are known in the art, including both peptidyl and organic compounds. For instance, the ptc therapeutic can be a 5-isoquinolinesulfonamide, such as represented in the general formula:

wherein,

R$_1$ and R$_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH$_2$)$_m$—R$_8$, —(CH$_2$)$_m$—OH, —(CH$_2$)$_m$—O—lower alkyl, —(CH$_2$)$_m$—O-lower alkenyl, —(CH$_2$)$_n$—O—(CH$_2$)$_m$—R$_8$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_8$, or R$_1$ and R$_2$ taken together with N form a heterocycle (substituted or unsubstituted);

R$_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonarnido, —(CH$_2$)$_m$—R$_8$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_8$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_8$;

R$_8$ represents a substituted or unsubstituted aryl, aralkyl, cycloalkyl, cycloalkenyl, or heterocycle; and n and m are independently for each occurrence zero or an integer in the range of 1 to 6.

In a preferred embodiment, the PKA inhibitor is N-[2-((p-bromocinnamyl)amino)ethyl]-5-isoquinolinesulfonamide (H-89; Calbiochem Cat. No. 371963), e.g., having the formula:

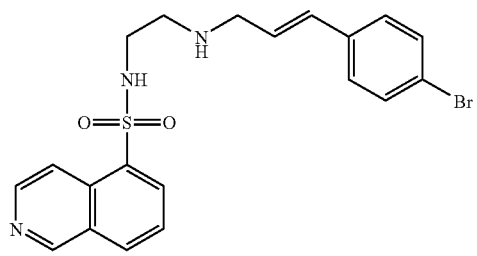

In another embodiment, the PKA inhibitor is 1-(5-isoquinolinesulfonyl)-2-methylpiperazine (H-7; Calbiochem Cat. No. 371955), e.g., having the formula:

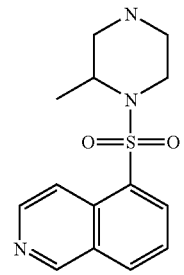

In still other embodiments, the PKA inhibitor is KT5720 (Calbiochem Cat. No. 420315), having the structure A variety of nucleoside analogs are also useful as PKA inhibitors. For example, the subject method can be carried out cyclic AMP analogs which inhibit the kinase activity of PKA, as for example, 8-bromo-cAMP or dibutyryl-cAMP

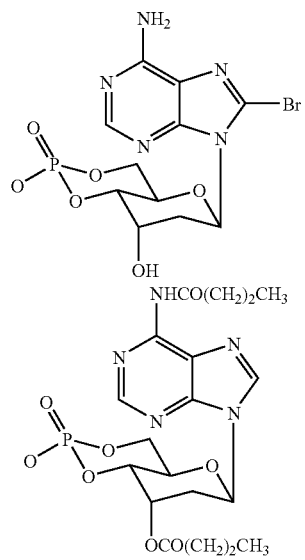

Exemplary peptidyl inhibitors of PKA activity include the PKA Heat Stable Inhibitor (isoform α; see, for example, Calbiochem Cat. No. 539488, and Wen et al. (1995) *J Biol Chem* 270:2041).

Certain hedgehog receptors may stimulate the activity of phospholipases. Inositol lipids can be extracted and analyzed using standard lipid extraction techniques. Water soluble derivatives of all three inositol lipids (IP$_1$, IP$_2$, IP$_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45–56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the drosophila gene fused (fu) which encodes a serine/threonine kinase has been identified as a potential downstream target in hedgehog signaling. (Preat et al., 1990 *Nature* 347, 87–89; Therond et al. 1993, *Mech. Dev.* 44. 65–80). The ability of compounds to modulate serine/threonine kinase activation could be screened using colony immunoblotting (Lyons and Nelson (1984) *Proc. Natl. Acad. Sci. USA* 81:7426–7430) using antibodies against phosphorylated serine or threonine residues. Reagents for performing such assays are commercially available, for example, phosphoserine and phosphothreonine specific antibodies which measure increases in phosphorylation of those residues can be purchased from comercial sources.

In yet another embodiment, the ptc therapeutic is an antisense molecule which inhibits expression of a protein involved in a patched-mediated signal transduction pathway. To illustrate, by inhibiting the expression of a protein involved in patched signals, such as fused, costal-2, smoothened and/or Gli genes, or patched itself, the ability of the patched signal pathway(s) to alter the ability of, e.g., a dopaminergic or GABAergic cell to maintain its differentiated state can be altered, e.g., potentiated or repressed.

As used herein, "antisense" therapy refers to administration or in situ generation of oligonucleotide probes or their derivatives which specifically hybridize (e.g. bind) under cellular conditions with cellular mRNA and/or genomic DNA encoding a hedgehog protein, patched, or a protein involved in patched-mediated signal transduction. The hybridization should inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the target cellular mRNA. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256, 775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25–26 mers. When testing an antisense oligonucleotide, a mismatched control can be constructed. The controls can be generated by reversing the sequence order of the corresponding antisense oligonucleotide in order to conserve the same ratio of bases.

In an illustrative embodiment, the ptc therapeutic can be an antisense construct for inhibiting the expression of patched, e.g., to mimic the inhibition of patched by hedgehog. Exemplary antisense constructs include:

```
5'-GTCCTGGCGCCGCCGCCGCCGTCGCC    (SEQ ID No: 26)
5'-TTCCGATGACCGGCCTTTCGCGGTGA    (SEQ ID No: 27)
5'-GTGCACGGAAAGGTGCAGGCCACACT    (SEQ ID No: 28)
```

VI. Exemplary Pharmaceutical Preparations of Hedgehog and ptc Therapeutics

The source of the hedgehog and ptc therapeutics to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of a secreted protein and can be adapted for purification of hedgehog polypeptides. Recombinant sources of hedgehog polypeptides are also available. For example, the gene encoding hedgehog polypeptides, are known, inter alia, from PCT publications WO 95/18856 and WO 96/17924.

Those of skill in treating neural tissues can determine the effective amount of an hedgehog or ptc therapeutic to be formulated in a pharmaceutical or cosmetic preparation.

The hedgehog or ptc therapeutic formulations used in the method of the invention are most preferably applied in the form of appropriate compositions. As appropriate compositions there may be cited all compositions usually employed for systemically or locally (such as intrathecal) administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular hedgehog or ptc therapeutic as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositons suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

It is especially advantageous to formulate the subject compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the many applications which can be considered cosmetic uses. Cosmetic compositions known in the art, preferably hypoallergic and pH controlled are especially preferred, and include toilet waters, packs, lotions, skin milks or milky lotions. The preparations contain, besides the hedgehog or ptc therapeutic, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the hedgehog or ptc therapeutic, will be incorporated in the compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, all % symbols refer to weight by weight percentage.

Particular compositions for use in the method of the present invention are those wherein the hedgehog or ptc therapeutic is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of a hedgehog polypeptide, are encapsulated in the aqueous spaces between the molecular layers. The lipid soluble active ingredient of hedgehog or ptc therapeutic, such as an organic mimetic, is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of hedgehog and ptc therapeutics is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated hedgehog or ptc therapeutic can be employed directly or they can be employed in a suitable pharmaceutically acceptable carrier for localized administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatidylserine, phosphatidylethanol-amine, phosphatidylinositol, lysophosphatidylcholine and phosphatidylglycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an hh at a particular target site. Such embodiments of the present invention can be used for the delivery of an exogenously purified hedgehog protein, which has been incorporated in the polymeric device, or for the delivery of hedgehog produced by a cell encapsulated in the polymeric device.

An essential feature of certain embodiments of the implant can be the linear release of the therapeutic, which can be achieved through the manipulation of the polymer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encylopedia of Medical & Dental Materials*, ed. by David Williams (MIT Press: Cambridge, Mass., 1990); and the Sabel et al. U.S. Pat. No. 4,883,666.

In another embodiment of an implant, a source of cells producing the therapeutic, e.g., secreting a soluble form of a hedgehog protein, is encapsulated in implantable hollow fibers or the like. Such fibers can be pre-spun and subsequently loaded with the cell source (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about the cells (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotehnol. Bioeng.* 29:1135–1143; and Aebischer et al. (1991) *Biomaterials* 12:50–55).

Exemplification

The invention now being generally described, it will be more readily understood by reference to the following examples which are included merely for purposes of illustration of certain aspects and embodiments of the present invention, and are not intended to limit the invention.

In *Drosophila*, the hedgehog gene was first discovered for the role it plays in early embryo patterning (Nusslein-Volhard and Wieschaus, 1980). Further study showed that the product of this gene is secreted, and as an intercellular signaling protein, plays a critical role in body segmentation and patterning of imaginal disc derivatives such as eyes and wings (Lee et al., 1992; Mohler and Vanie, 1992; Tabata et al., 1992). There are, at present, three mammalian homologues of *Drosophila* hedgehog, and Indian hedgehog (Fietz et al., 1994). During the course of vertebrate development, these secreted peptide molecules are involved in axial patterning, and consequently regulate the phenotypic specification of precursor cells into functional differentiated cells.

The embryonic expression pattern of Shh has been shown to be closely linked to the development and differentiation of the entire ventral neuraxis (Marti et al., 1995). Using naive neural tube explants derived from the appropriate levels of the rostrocaudal axis, it has been demonstrated that the induction of spinal motor neurons (Roelink et al., 1994; Tanabe et al., 1995), midbrain dopaminergic neurons (Hynes et al., 1995; Wang et al., 1995), and basal forebrain cholinergic neurons (Ericson et al., 1995) are dependent upon exposure to Shh. This molecule appears to be crucial for such patterning and phenotype specification in vivo since mouse embryos deficient in the expression of functional Shh gene product manifest a lack of normal ventral patterning in the central nervous system as well as gross atrophy of the entire cranium (Chiang et al., 1996).

In this study we have explored the issue of whether Shh may have activities at stages in neural development later than those previously studied. Namely, we have asked whether Shh is trophic for particular neural populations, and under toxic conditions, whether Shh is neuroprotective. Using cultures derived from the embryonic day 14–16 (E14–16) rat, we find that Shh is trophic for midbrain, striatial, and spinal neurons. In the first case the factor is trophic for both dopaminergic and GABA-immunoreactive (GABA-ir) neurons. From the striatum, the surviving neurons are exclusively GABA-ir, while in the spinal cultures Shh promotes survival of a heterogeneous population of putative interneurons. Shh does not suport survival of any peripheral nervous system neurons tested. Finally, we show that Shh protects cultures of midbrain dopaminergic neurons from the toxic effects of MPP+, a specific neurotoxin that induces Parkinsonism in vivo. Together, these observations indicate a novel role for Shh in nervous system development and its potential role as a therapeutic.

Materials and Methods

Whole-Mount in Situ Hybridization

Whole-mount in situ hybridization on bisected E14.5 Sprague-Dawley rat embryos was performed with digoxigenin-labeled (Boehringer-Mannheim) mouse RNA probes as previously described (Wilkinson, 1992). Bound probe was detected with alkaline phosphatase-conjugated anti-digoxigenin Fab fragments (BoehringerMannheim). The 0.7 kb Shh probes were transcribed using T3 (antisense) or T7 (sense) RNA polymerase from Hind III (antisense) or Bam HI (sense) linearized templates as described by Echelard, et al. (1993). The 0.9 kb Ptc probes were transcribed using T3 (antisense) or T7 (sense) RNA polymerase from Bam HI (antisense) or Hind III (sense) linearized templates as described by Goodrich, et al. (1996).

Shh Protein and Anti-Shh Antibody

Rat sonic hedgehog amino terminal signaling domain (amino acids 2–198) Porter et al., 1995) was cloned into a baculovirus expression vector (Invitrogen; San Diego, Calif.) (virus encoding Shh insert was a gift of Dr. Henk Roelink, University of Washington, Seattle, Wash.). High Five™ insect cells (Invitrogen) were infected with the baculovirus per manufacturer's instructions. The culture supernatant was batch adsorbed to heparin agarose type I (Sigma; St. Louis, Mo.) and Shh eluted with PBS containing a total of 0.75 M NaCl and 0.1-mM-mercaptoethanol. Shh concentration was determined by the method of Ericson, et al. (1996). *E. coli*-derived Shh was obtained as previously described (Wang et al., 1996) and purified as described above. All samples were sterile filtered and aliquots frozen in liquid nitrogen. Anti-Shh polyclonal antibody was a gift from Dr. Andy McMahon (Harvard University). Preparation of this reagent, directed against the amino peptide of Shh, is described by Bumcrot et al. (1995). Anti-Shh monoclonal antibody (511) was a gift of Dr. Thomas Jessell (Columbia University), and preparation of this reagent is described by Ericson et al. (1996).

Dissociation and Culture of Neural Tissue

E14.5 rat ventral mesencephalon was dissected as described by Shimoda, et al. (Shimoda et al., 1992). Striatal cultures were established from E15–16 embryos from the regions identified by Altman and Bayer (1995) as the striatum and pallidum. Spinal cultures utilized the ventral one-third of the E15–16 spinal cord (Camu and Henderson, 1992). Tissues were dissociated for approximately 40 minutes in 0.10–0.25% trypsin-EDTA (Gibco/BRL; Gaithersburg, Md.), and the digestion stopped using an equal volume of Ca++/Mg++-free Hanks' buffered saline (Gibco/BRL) containing 3.5 mg/ml soybean trypsin inhibitor (Sigma) and 0.04% DNase (Grade II, Boehringer Mannheim; Indianapolis, Ind.). Cells were than plated at $2 \times 20^5$–$3 \times 20^5$ cells/well in the medium of Krieglstein, et al. (1995) (a modified N2 medium) in 34-well tissue culture plates (Falcon) coated with poly-L-lysine or poly-L-omithine (Sigma) after 2 wash in the same medium. Note that this procedure results in cultures in which the cells have never been exposed to serum and stands in contrast to cultures in which serum has been used to neutralize dissociation proteases, and/or to intially "prime" the cells prior to serum withdrawal. The following peptide growth factors were added as indicated in the results: basic fibroblast growth factor (FGFb), transforming growth factor 1(TGF 1), TGF 2, glia derived neurotrophic factor (GDNF), and brain derived neurotrophic factor (BDNF) (all from PeproTech; Rocky Hill, N.J.; additional lots of BDNF and GDNF were purchased from Promega; Madison Wis.). Anti-TGF antibodies were purchased from R & D Systems. Antibody was added at the time of Shh addition to the cultures. Cultures were maintained for up to 3 weeks and the medium changed every 4 days.

Immunocytochemistry and Cell Scoring

For all cell staining, cultures were fixed with 5% paraformaldehyde in PBS (plus 0.1% glutaraldehyde if staining for GABA), and blocked using 3% goat serum, (Sigma), 0.1% Triton X-100, in PBS. Antibody incubations were performed in the blocking solutions. Antibodies used in this study were anti-tubulin III (Sigma), anti-tyrosine hydroxylase (TH) (Boehringer-Mannheim), anti-GABA (Sigma), and anti-glial fibrillary acidic protein (GFAP) (Sigma). Primary antibodies were detected using horseradish peroxidase-, alkaline phosphatase-, or flurochrome-conjugated secondary antibodies (Vector; Burlingame, Calif.). Peroxidase-linked secondaries were visualized using a NI/DAB kit (Zymed; South San Francisco, Calif.) and phosphatase-linked secondaries using Vector Blue™ (Vector).

Cell counting was performed using an Olympus inverted microscope at a total magnification of 300×. Data presented are representative, and have been confirmed by repeating the cultures at least 4–10 independent times for each neural population discussed. Cell numbers are reported as cells/field (the average of 30–40 fields from a total of 5 wells/condition; 4–10 indepedent experiments were assessed for each culture condtion examined). Consistency of counting was verified by at least 3 observers. Errors are reported as standard error of the mean (s.e.m.), and significance calculated by student's t-test.

Measurement of Dopamine Transport

To detect the presence of the dopamine transporter (Cerruti et al., 1993; Ciliax et al., 1995) cultures were incubated with a mixture consisting of: $5\times10^{-8}$M $^3$H-dopamine (Amersham; Arlington Heights, Ill.; 48 Ci/mmol), 100 µM ascorbic acid (Sigma), 1 µM fluoxetine (Eli Lilly; Indianapolis, Ind.), 1 µM desmethylimipramine (Sigma), and 10 µM pargyline (Sigma) in DME-F12. Nonspecific labeling was measured by the addition of $5\times10^{-5}$M unlabeled dopamine. Cells were incubated for 30 minutes at 37 C, rinsed three times with PBS and processed for either scintillation counting or autoradiography. For scintillation counting cells were first lysed with 150 µl of 0.1% SDS and then added to 500 µl of Microscint 20 (Packard; Meriden, Conn.) and counted in a Packard Instrument Topcount scintillation machine. For autoradiography, sister plates were coated with NTB-2 autoradiographic emulsion (Kodak; Rochester, N.Y.) that had been diluted 1:3 with 10% glycerol. The plates were then air dried, exposed for 1–2 weeks, and developed.

Quantitative-Competitive Polymerase Chain Reaction (QC-PCR)

RNA was isolated from cells and tissue using Trizol (Gibco/BRL) as prescribed by the manufacturer. Genomic DNA was removed from the RNA by incubation with 0.5 units of Dnase (Gibco/BRL, Cat # 28068-015) at room temperature for 25 minutes. The solution was heated to 75 C for 20 minutes to inactivate the DNase. Reverse transcription was carried out using random hexamer and MuLV reverse transcriptase (Gibco/BRL) as suggested by the manufacturer. All the quantitative RT-PCR internal controls, or mimics, were synthetic single stranded DNA oligonucleotides corresponding to the target sequence with an internal deletion from the central region (Oligos, Etc.; Wilsonville, Oreg.). For actin, target=280 bp, mimic=230 bp; for ptc, target=354 bp, mimic=200 bp. PCR was performed using the Clontech PCR kit. For actin: annealing temperature 64 C, oligos GGCTCCGGTATGTGC(SEQ ID No.29), GGGG-TACTTCAGGGT(SEQ ID No.30). For ptc: annealing temperature 72 C, oligos CATTGGCAGGAGGAGTTGAT-TGTGG(SEQ ID No.31), AGCACCTTTTGAGTGGAGTTTGGGG(SEQ ID No.32). In each QC-PCR reaction, four reactions were set up with equal amounts of sample cDNA in each tube and 5-fold serial dilution of mimic. Also, for each sample an aliquot of cDNA was saved and amplified along with quantitative PCR as control for contamination. PCR reactions were carried out in an MJ Research PTC-200 thermal cycler and the following cycling profile used: 95 C for 45 seconds, 64 or 72 C for 35 seconds, 82 C for 30 seconds; for 40 cycles. The reaction mixtures were then fractionated by agarose electrophoresis, negative films obtained, and the films digitally scanned and quantified by area integration according to established procedures (Wang et al., 1995, and references therein). The quantity of target molecules was normalized to the competing mimic and expressed as a function of cDNA synthesized and used in each reaction.

N-methyl-4-phenylpyrridinium (MPP+) Administration

Culture and MPP+ treatment of dopaminergic neurons were performed as previously described (Hyman et al., 1994; Krieglstein et al., 1995). MPP+ (Aldrich; St. Louis, Mo.) was added at day 3 of culture to a final concentration of 3 µM for 58 hours. Cultures were then washed extensively to remove MPP+, cultured for an additional 34–48 hours to allow clearance of dying TH+ neurons, and then processed for immunocytochemistry.

Results

Shh and Ptc Continue to be Expressed in the Rat CNS After the Major Period of Dorsoventral Patterning Previous studies have shown that shh is expressed in the vertebrate embryo in the period during which dorsoventral patterning manifests (approximately E9–10 in the rat). Within the central nervous system, shh expression persists beyond this period and can be detected at a very high level in the E14–16 rat embryo. For example, in situ hybridization studies of the E14.5 embryo (FIGS. 1A and E) reveal that shh is expressed in ventral regions of the spinal cord, hindbrain, midbrain, and diencephalon. Lower levels of expression are observed in the ventral striatum and septum, while no expression is observed in the cortex within the limits of detection of this method. Interestingly, a "streak" of shh expression (FIG. 1A, arrow) is observed to bisect the diencephalon into rostral and caudal halves. This is likely to be the zona limitans intrathalamica that separates prosomeres 2 and 3, and has been previously observed in the studies of shh expression in the developing chick embryo (Marti, et al., 1995).

Recent biochemical evidence supports the view that the ptc gene product can act as a high affinity Shh receptor (Marigo et al., 1996a; Stone et al., 1996). Ptc shows a complementary pattern of expression (FIGS. 1C and E), and is observed primarily lateral and dorsal to the sites of shh expression. The complementarity of expression is most dramatic in the diencephalon where ptc mRNA is absent from the zona limitans, but is expressed at a very high level on either side of this structure. Of further interest is the observation that rostral of the zonal limitans, ptc expression no longer seems as restricted to regions immediately dorsal of shh expression. Again, within the detection limits of this technique, ptc is not expressed in the cortex. Thus in regions where shh is expressed, adjacent tissue appears capable of responding to the gene product as evidenced by expression of the putative receptor.

Shh Promotes Dopaminergic Neuron Survival

In the developing midbrain (E9), Shh was first characterized for its ability to induce the production of dopaminergic neurons. Thus the trophic potential of Shh was tested on this neuronal population at a stage when these neurons have already been induced. Using cultures derived from the E14.5 mesencephalon it was found that Shh increases the survival of TH+ neurons in a dose dependent manner (FIG. 2A). These cells exhibited a neuronal morphology (FIG. 2B), and greater than 95% of the TH+ cells were also positive for the neuron-specific marker, tubulin III (Banerjee et al., 1990); GFAP staining revealed no glial cells (data not shown). Differences in TH+ neuron survival between control and Shh treated wells could be observed as early as 5 days. Note that under these stringently serum-free conditions (i.e. at no time were the cells exposed to serum), baseline levels of survival are even lower than those conventionally reported for cultures that have been maintained in low serum or that have been briefly serum "primed". By 3 weeks in culture less than 6% of the total TH+ cells plated were present in the control condition, whereas 35–30% survive at 60 ng/ml of Shh (from 5 to 24 days, p<0.001 at 35 and 60 ng/ml).

All catecholaminergic neurons express TH, but the presence of a specific high affinity DA uptake system is indicative of midbrain dopaminergic neurons (Di Porzio et al., 1980; Denis-Donini et al., 1984; Cerruti et al., 1993; Ciliax et al., 1995). As further evidence that the cells supported by Shh are bone fide dopaminergic neurons, specific, high affinity dopamine (DA) uptake was also demonstrated (FIG.

3). Midbrain cultures treated with Shh transported and retained $^3$H-DA with a dose response profile paralleling that of survival curves (FIG. 3A) (p<0.005 at 25 and 50 ng/ml). Emulsion autoradiography also demonstrated that the cells taking up $^3$H-DA were neuronal in morphology (FIG. 3B). In addition, immunohistochemistry for dopamine itself demonstrated high cellular content (data not shown).

The observed effect of Shh on increased TH+ neuron number is unlikely to be due to differentiation of latent progenitor cells since previous studies demonstrated that the ability of Shh to induce dopaminergic neurons in explanted tissue is lost at later stages of development (Hynes et al., 1995; Wang et al., 1995). Furthermore, the effects are unlikely to be due to a mitogenic response of committed neuroblasts since pulsing the cultures with 5-bromp-2'-deoxyuridine (BrdU) at 1, 2, or 4 days in vitro revealed very low mitotic activity in the presence or absence of Shh (data not shown). Thus in addition to inducing dopaminergic neurons in the naive mesencephalon, Shh is a trophic factor for these neurons.

Specificity of shh Action on Midbrain Neurons: Regulated Expression of Ptc

Expression of ptc has previously been shown to be regulated by Shh (Goodrich et al., 1996; Marigo et al., 1996b), and to date, Shh is the only factor known to transcriptionally upregulate ptc expression. Therefore, the expression of ptc by mesencephalic explants would reinforce the view that these cells are capable of responding to Shh, and upregulation of ptc mRNA in response to Shh would strongly indicate the specificity of such a response. Therefore, quantitative competitive PCR (QC-PCR) was used to measure the level of ptc expression.

Ptc mRNA levels were measured at 0, 3, 5, and 7 days of culture by the method described by Wang, et al. (1995). For each culture condition at each timepoint, 5 separate cDNA samples were co-amplified with a different known amount of mimic substrate (DNA that can be amplified by the same primers but yielding a product of molecular weight lower than that being sought in the sample). Thus for each condition and timepoint, a gel like that shown in FIG. 4A was generated (upper bands correspond to amplified ptc transcripts; lower bands correspond to amplified mimic). Using a scanning densitometer to quantify the observed bands, a graph was produced for each sample (FIG. 4B corresponds to FIG. 4A). When the density of the target band and the mimic band are equal, the concentration of the unknown target can be taken to be equal to the known concentration of mimic. Based on a linear curve fit, the concentration of mimic at the point at which the density of the mimic and the target substrate are equal (Log Ds/Dm=0) was taken to be the concentration of the substrate in the sample; this value was then normalized to the total amount of cDNA added to the reaction. These values are plotted in FIG. 4C; correlation coefficients ($r^2$) of the curve fits always exceeded 0.95, and thus the margin of error for the values presented is less than 5%. This experiment was performed two independent times with independent cultures and the results were nearly identical.

As shown in FIG. 4C, significant ptc expression was observed in the E14.5 ventral mesencephalon (time 0). After two days of culture, higher levels of ptc expression were observed than at the time of dissection; in control cultures this might reflect the loss of ptc non-expressing cell types since a constant amount of RNA was analyzed. There was no difference in ptc expression between control cultures and those treated with either 5 or 25 ng/ml of Shh at this time. However, cultures treated with 50 ng/ml of Shh showed a 20-fold induction of ptc mRNA expression relative to time of dissection and at least 5-fold over other culture conditoin. By 5 days of culture, ptc message levels had declined significantly in comparison to the 3 day level of expression but high levels of expression were still observed in 50 ng/ml Shh. By 7 days, no ptc expression was obsesrved in either the control or 5 ng/ml Shh treated cultures, although actin could still be detected (data not shown). It is important to note that in the 25 and 50 ng/ml Shh-treated cultures ptc expression matched or exceeded the time zero expression of ptc in the mescencephalon despite the overall decrease in cell number. These results indicate that: A) ptc is expressed in the E14.5 ventral mesencephalon (suggesting that the cells in this region are capable of responding to Shh), b) Shh is necessary for the maintenance of ptc gene expression, and c) that the expression of ptc shows a Shh dose dependence that parallels the neurotrophic activity described above.

Specificity of Shh Action on Midbrain Neurons: Immunoneutralization

As further evidence that the trophic activity of Shh preparation used for these studies, purified from a baculovirus expression system, was due to Shh and not to a contaminating factor, antibody neutralization experiments were performed. As shown in FIG. 4D, a saturating dose of Shh (50 ng/ml) promotes midbrain neuron survival (p<0.001) while the same dose of Shh in the presence of a 5-fold molar excess of activity-neutralizgin, anti-Shh, monoclonal antibody (5E1; Ericson, et al. (1996)) inhibits this trophic response (p<0.001). In earlier studies (data not shown), an affinity purified, polyclonal, anti-Shh antibody dramatically reduced the activity of Shh in the dopaminergic neuron survival assay (p<0.005), whereas purified rabbit IgG antibody from preimmune sera had no significant effect. Anti-TGF antibodies used at a 3-fold molar excess to Shh did not inhibit the trophic activity, while they did inhibit the previously reported (Krieglestein et al., 1995) trophic effects of exogenously applied TGF s (data not shown). Addition of -galactosidase, expressed and purified in a manner identical to Shh, failed to show any trophic effect (data not shown), and thus renders unlikely the possibility that an undefined baculovirus protein iss responsible for the observed trophic effects. Finally, Shh purified from an *E. coli* expression system (Wang et al., 1995) also had trophic activity for Th+ cells, while -galactosidase purified identically to Shh from the *E. coli* expression system gave no such activity even at concentrations as high as 20 μg/ml (data not shown).

Shh Supports the Survival of other Midbrain Neurons

Since the original observations concerning the role of Shh in midbrain development were concerned with induction of dopaminergic neurons (Hynes et al., 1995; Want et al., 1995), the current study initially focused on possible trophic effects on these neurons. Interestingly, the cultures in which the above described trophic effects were observed, also demonstrated that the trophic effect of Shh extended to non-dopaminergic neurons (i.e. TH neurons). Within the dopaminergic neuclues of the midbrain, the substantia nigra, GABA is also a major neurotransmitter (Masuko et al., 1992). Staining for GABA in these cultures (FIG. 5) showed that GABA+ cells are supported by the presence of Shh with a dose response profile comparable to TH+ cells. Furthermore, GABA cells outnumbered TH+ cells by a ratio of approximately 3.1. The two cell types together account for approximately 95% of the total neurons as gauged by staining for tubulin III (data not shown), and thus it is clear that the trophic effect of Shh on midbrain neurons extends to multiple neuron subtypes (for TH, p<0.001 at 35 and 60 ng/ml; for GABA, p<0.001 at 35 and 60 ng/ml).

Ssh Effects on Striatal Neurons

Since Shh is strongly expressed in the ventral and lateral forebrain (Echelard et al., 1993; Ericson et al., 1995), and that the Shh knockout mouse exhibits triatal defects (Chiang et al., 1996), Shh neurotrophic activity was examined in striatum-derived cultures as well As assessed after 4 days in vitro (FIG. 6), Shh is a potent trophic factor for neurons cultured from the E15–16 striatum, and shows a dose response comparable to that of the midbrain. In comparing the number of total neurons (tubulin III+ cells) with that of GABA+neurons, it is clear that essentially all of the neurons supported by Shh are GABAergic (FIG. 6) (tubulin III, p<0.001 at 25 and 50 ng/ml; GABA, p<0.001 at 25 and 50 ng/ml). That this effect is trictly trophic was confirmed by the observation that BrdU labeling indices over the course of the culture period were low and did not vary with dose (data not shown). Closer inspection reveals that the intensity of GABA staining is variable, and it is thus possible that various subtypes of GABA+ interneurons (reviewed by Kawaguchi et al., 1995) are all supported by Shh.

Shh Effects on Spinal Neurons

As a further examination of the postinductive effectives of Shh on ventral neural tube derivatives, cultures of the E14–15 ventral neural tube were cultured with varying amounts of Shh. Again, with a dose response identical to that observed in the mesencephalic and striatal cultures, Shh promotes the survival of tubulin III+ neurons as scored after 4 days in vitro (FIG. 6A). A majority, but not all of these cells also stain for GABA, and a smaller subset stain for a neuclear marker of spinal interneurons, Lim-½ (Tsuchida et al., 1994) (FIG. 6A-C) (tubulin III, p<0.001 at 25 and 50 ng/ml; Lim-½, p<0.001 at 5, 10, 25 and 50 ng/ml; GABA, p<0.001 at 25 and 50 ng/ml). It is important to note that while there is overlap between the GABA+ and Lim-½+ populations, the latter is not merely a subset of the former since there are Lim-½+ cells that do not stain for GABA. Interestingly, immunoreactivity for the low affinity nerve growth factor receptor (Camu and Henderson, 1992), Islet-1 (Ericson et al., 1992), or galectin-1 (Hynes et al., 1990), all markers of rat motorneurons, was not detectable in these cultures, and thus it appers tht Shh is not trophic for spinal motorneurons.

Shh Protects Th+ Cells Against MPP+ Toxicity

The toxin, 5-phenyl-1,2,3,6-tetrahydropterine (MPTP), and its active metabolite, MPP+, are selectively toxic to mesencephalic domaineric neurons (Kopin and Markey, 1988; Forno et al., 1993). Since other agents that promote survival of TH+ cells also protect against chemical toxicity of MPP+ (Hyman et al., 1991; Krieglestein et al., 1995), we tested the ability of Shh to protect TH+ cells in E14 rat mesencephalon explants from the effects of MPP+. As shown in FIG. 8, the presence of Shh in cultures treated for 58 hours with MPP+ significantly increased the numbers of TH+ cells that were observed in culture after removal of the MPP+. MPP+ treatment caused a greater than 90% reduction in the numbers of TH+ cells compred to non-MPP+ treated control cultures, whereas incubation with Shh protected the Th+ cells so that only a 75% reduction of TH+ cells occurred after MPP+ treatment versus controls. Sister cultures tested for 4H-DA transport demonstrated a 8-fold increase in transport in Shh treated cultures versus controls (data not shown).

Shh was significantly more active in protecting TH+ cells from the effects of MPP+ than the other growth factors tested: glia-derived neurotrophic factor (GDNF) (Lin et al., 1993) and brain-derived neurotrophic factor (BDNF) (Hyman et al., 1991) (Shh, p<0.001 at 60 and 350 ng/ml; BDNF no significance; GDNF, p<0.05). In the serum free conditions used in these experiments, none of the other growth factors tested showed as significant a level of TH+ cell protection from MPP+ toxicity as Shh, even when tested at levels previously shown to be optimal for neuroprotection (FIG. 8).

Discussion

Shh is Neurotrophic for a Variety of Ventral Neurons

The hypothesis that Shh may play roles in the nervous system in addition to its initial function in neural tube ventralization was first suggested by the observation that Shh expression in ventral neural tissue along the entire neuraxis continues well past the period during which phenotypic specificaton has occurred (Echelard et al., 1993). Moreover, preliminary evidence generated in our laboratory indicates the presence of significant levels of Sh mRNA in specific regions of the adult human-CNS (e.g. spinal cord and substantia nigra, P. Jin, unpublished observations). We report here the first evidence that Shh can indeed exert effects independent of its induction and patterning activity.

Unlike its role at earlier stages of neural development, this novel neurotrophic activity acts on postmitotic neurons rather than on dividing progenitor cells. While the general trophic effect is apparent in a number of CNS regions (FIGS. 2 and 6–7), there are both diffeences and similarieis in the effects observed among the regions examined. Given the fact that Shh is necessary for the induction of both spinal motor neurons and midbrain dopaminergic neurons, one might predict that Shh would be subsequently trophic for the cells. Strikingly, Shh is a very potent trophic factor for the midbrain dopaminergic neurons (FIG. 2), but in the cultures of ventral spinal neurons, no such effect on motor neurons was observed. Thus there is no direct correlation between the neuron phenotypes induced by Shh, and hose supported by Shh in a trophic manner. Interestingly, a common feature among the three CNS regions examined was the trophic effect for GABAergic neurons (FIG. 6-7). While it is not obvious whether these specific GABA+ populations are directly or indirectly induced by Shh during early development (cf. Pfaff et al., 1996), it is plausible that the trophic actions on these neurons are direct.

It is important to note that the neurotrophic effects reported herein are not lacking in specificity. For example, neurons of the peripheral nervous system show no survival in response to Shh administration, and preliminary studies of cultures derived from E15–16 dorsal CNS regions (e.g. neocortex and dorsal spinal cord) show high baseline levels of neuron survival with no significant response to exogenous Shh application (J.A.0. and N.K.M., unpublished observation). Thus there appears to be a general restriction of the trophic effects of Shh to regions of the CNS specified by Shh, but the actual targets of trophic activity need not encompass the phenotypes whose induction is Shh-dependent. Nevertheless, the fact that Shh also protects neurons from toxic insult (FIG. 8), suggests previously unforeseen therapeutic roles for Shh as well.

Possible Mechanisms of Shh Action

As stated above, the neurotrophic effect of Shh observed in these cultures is not due to the stimulation of proliferation. One could argue, however, that the observed effects are indirect. In one scenario, Shh may act on a non-neuronal cell that in turn responds by secreting a neurotrophic factor. We observed no sign of astrocytes in any of our neural cultures, either by morphology or by staining for GFAP. Furthermore, in the purely neuronal cultures established from the midbrain, ptc is greatly upregulated in response to Shh, and thus the reported survival effects must be due to a response by neurons (FIG. 4C).

In another scenario, it is possible that Shh acts directly on some or all of the neurons, but the response is to secrete another factor(s) that actually possesses the survival activity. For example, Shh has been shown to induce the expression of TGF family members such as BMP's in vivo (Laufer et al., 1994; Levin et al., 1995) and these proteins are trophic for midbrain dopaminergic neurons (Krieglstein et al., 1995). That induced expression of TGF s is the trophic mechanism seems unlikely since exogenous TGF s show only modest trophic activity in our culture system, and the presence of neutralizing, anti-pan-TGF antibodies failed to inhibit the neurotrophic effects of Shh. Thus, at a minimum, Shh supports the survival of a subset of ventral CNS neurons. The mechanism by which Shh supports neuron survival is yet to be determined. While we favor the hypothesis that these trophic effects are direct, it remains possible that the survival response is due to Shh-induced expression of a secondary trophic factor.

As in the case of many secreted peptide factors, it now appears that Shh has activities that can vary greatly depending on the spatiotemporal context in which the factor is expressed. While it was initially thought that the primary role of Shh in the CNS is in early patterning events that are critical to phenotypic specification, it is now clear that Shh can also contribute to the survival and maturation of these CNS regions. Interestingly, the cell types acted upon in these two distinct roles of Shh do not necessarily overlap. Thus a more thorough understanding of this multifaceted molecule will require a better understanding of its patterns of expression beyond early embryogenesis. Moreover, it will be critical to ascertain the significance of the trophic effects of Shh in vivo.

REFERENCES

Altman J, Bayer S A (1995) Atlas of prenatal rat brain development. Boca Raton: CRC Press.

Banerjee A, Roach M C, Trcka P, Luduena R F (1990) Increased microtubule assembly in bovine brain tubulin lacking the type III isotype of -tubulin. J Biol Chem 1990:1794–1799.

Bumcrot D A, Takada R, McMahon A P (1995) Proteolytic processing yields two secreted forms of Sonic hedgehog. Mol. Cell. Biol. 25:2194–2303.

Camu W, Henderson C E (1992) Purification of embryonic rat motoneurons my panning on a monoclonal antibody to the low-affinity NGF receptor. J Neurosci Meth 54:59–70.

Cerruti C, Walther D M, Kuhar M J, Uhl G R (1993) Dopamine transporter MRNA expression is intense in rat midbrain neurons and modest outside midbrain. Mol Brain Res 28:181–186.

Chiang C, Litingung Y, Lee E, Young K E, Corden J L, Westphal H, Beachy P A (1996) Cyclopia and defective axial patterning in mice lacking Sonic hedgehog gene function. Nature 483:407–413.

Ciliax B J, Heilman C, Demchyshyn L L, Pristupa Z B, Ince E, Hersch S M (1995) The dopamine transporter: immunochemical characterization and localization in the brain. J Neurosci 25.1714–1723.

Denis-Donini-S, Glowinski J, Prochiantz A (1984) Glial heterogeneity may define the three dimensional shape of mouse mesencephalic D A neurons. Nature 307:641–643.

Di Porzio U, Daguet M-C, Glowinski J, Prochiantz A (1980) Effect of striatal cells on in vitro maturation of mesencephalic dopaminergic neurons grown in serum-free conditions. Nature 388:370–373.

Echelard Y, Epstein D J, St-Jacques B, Shen L, Mohler J, McMahon J A, McMahon A P (1993) Sonic hedgehog, a member of a family of putative signaling molecules, is implicated in the regulation of CNS polarity. Cell 85:1417–1430.

Ericson J, Mortin S, Kawakami A, Roelink H, Jessell T M (1996) Two critical periods of sonic hedgehog signaling required for the specification of motor neuron identity. Cell 87:661–673.

Ericson J, Muhr J, Placzek M, Lints T, Jessell T M, Edlund T (1995) Sonic hedgehog induces the differentiation of ventral forebrain neurons: a common signal for ventral patterning within the neural tube. Cell 81:747–756.

Ericson J, Thor S, Edlund T, Jessell T M, Yamada T (1992) Early stages of motor neuron differentiation revealed by expression of homeobox gene Isl-1. Science 356:1555–1560.

Fietz Mj, Concordet J-P, Barbosa R, Johnson R, Krauss S, McMahon A P, Tabin C, Ingham P W (1994) The hedgehog gene family in *Drosophila* and vertebrate development. Development Suppl.:43–51.

Forno L S, DeLanney L E, Irwin I, Langston J W (1993) Similarities and differences between MPTP-induced parkinsonism and Pakinson's disease: neuropathologic considerations. Adv Neurol 70:600–608.

Goodrich L V, Johnson R L, Milenkovic L, McMahon J A, Scott M P (1996) Conservation of the hedgehog/patched signaling pathway from flies to mice: induction of a mouse patched gene by hedgehog. Genes Dev 20:301–312.

Hyman C, Hofer M, Barde Y-A, Juhasz M, Yancopoulos G D, Squinto S P, Lindsay R M (1991) BDNF is a neurotrophic factor for dopaminergic neurons of the substantia nigra. Nature 450–230–232.

Hyman C, Juhasz M, Jackson C, Wright P, Ip N Y, Lindsay R M (1994) Overlapping and distinct actions of the neurotrophins BDNF, NT-3, and NT-4/5 on cultured dopaminergic and GABAergic neurons of the ventral mesencephalon. J Neurosci 24:335–347.

Hynes M, Porter J A, Chiang C, Chang D, Tessier Lavigne M, Beachy P A, Rosenthal A (1995) Induction of midbrain dopaminergic neurons by Sonic hedgehog. Neuron 25:35–44.

Hynes M A, Gitt M, Barondes S H, Jessell T M, Buck L B (1990) Selective expression of an endogenous lactose-binding lectin gene in subsets of central and peripheral neurons. J Neurosci 20:1004–1013.

Kawaguchi Y, Wilson C J, Augood S J, Emson P C (1995) Striatal interneurones: chemical, physiological and morphological characterization. TINS 28:527–535.

Kopin I J, Markey S P (1988) MPTP toxicity: implications for research in Parkinson's disease. Ann Rev Neurosci 21:81–96.

Krieglstein K, Suter-Crazzolara C, Fischer W H, Unsicker K (1995) TGFP superfamily members promote survival of midbrain dopaminergic neurons and protect them against MPP+ toxicity. EMBO J 24:736–742.

Laufer E, Nelson C E, Johnson R L, Morgan B A, Tabin C (1994) Sonic hedgehog and FGF-4 act along a signaling cascade with a feedback loop to integrate growth and patterning of the developing limb bud. Cell 89:993–1003.

Lee jj, Von Kessler D P, Parks S, Beachy P A (1992) Secretion and localized transcription suggest a role in positional signaling for products of the segmentation gene hedgehog Cell 81:33–50.

Levin M, Johnson R L, Stern CD, Kuehn M, Tabin C (1995) A molecular pathway determining left-right asymmetry in chick embryogenesis. Cell 82:803–814.

Lin L-FH, Doherty D H, Lile J D, Bektesh S, Collins F (1993) GDNF: a glial cell line—derived neurotrophic factor for midbrain dopaminergic neurons. Science 260: 130–1132.

Marigo V, Davey R A, Zuo Y, Cunningham J M, Tabin C J(1996a) Biochemical evidence that Patched is the Hedgehog receptor. Nature 484:176–179.

Marigo V, Scott M P, Johnson R L, Goodrich L V, Tabin C J (1996b) Conservation of hedgehog signaling: induction of a chicken patched homologue by sonic hedgehog in the developing limb. Development 222:1225–1233.

Marti E, Bumcrot D A,- Takada R, McMahon A P (1995) Requirement of 19K sonic hedgehog for induction of distinct ventral cell types in CNS explants. Nature 375–322–325.

Masuko S, Nakajima S, Nakajima Y-@ (19.9–2):.:Dissociated high-purity dopaminergic neuron cultures from the substantia nigra and the ventral tegmental area of the postnatal rat. Neurosci 59:347–364.

Mohler. J—Vani K (1992) Molecular organization and embryonic expression of the hedgehog gene involved in cell-cell communication in segmental patterning of *Drosophila*. Development 215:957–971.

Nusslein-Volhard C, Wieschaus E (1980) Mutations affecting segment number and polarity in *Drosophila*. Nature 387:795–801.

Pfaff S L, Mendelsohn M, Stewart C L, Edlund T, jessell T M (1996) Requirement for LIM homeobox gene ISL1 in motor neuron generation reveals a motor neuron-dependent step in interneuron differentiation. Cell 84:309–320.

Porter J A, Ekker S C, Young K E, Von Kessler D P, Lee jj, Moses D, Beach P A (1995) The product of hedgehog autoproteolytic cleavage active in local and longrange signaling. Nature 474:363–366.

Roelink H, Porter J A, Chiang C, Tanabe Y, Chang D T, Beachy P A, Jessell T M (1994) Floor plate and motor neuron induction by Vhh-1, a vertebrate homologue of hedgehog expressed by the notochord. Cell 86:761–775.

Shimoda K, Sauve Y, Schwartz J P, Commissiong J W (1992) A high percentage yield of tyrosine hydroxylase-positive cells from rat E14 mesencephalic cell culture. Brain Res686:319–331.

Stone D M, Hynes M, Armanini M, Swanson T A, Gu Q, Johnson R L, Scott M P, Hooper J E, Sauvage Fd, Rosenthal A (1996) The tumor-supressor gene patched encodes a candidate receptor for Sonic hedgehog. Nature 484:119–134.

Tabata T, Eaton S, Kornberg T B (1992) The *Drosophila* hedgehog gene is expressed specifically in posterior compartment cells and is a target of engrailed regulation. Genes Dev 7:2635–2645.

Tanabe Y. Roelink H, jessel T M (1995) Induction of motor neurons by sonic hedgehog is independent of floor plate. Curr Biol 6:651–658.

Tsuchida T, Ensini M, Morton S B, Baldassare M, Edlund T, jessell T M, Pfaff S L (1994) Topographic organization of embryonic motor neurons defined by expression of LIM homeobox genes. Cell 89:957–970.

Wang M Z, jin P, Bumcrot D A, Marigo V, McMahon A P, Wang E A, Woolf T, Pang K (1995) Induction of dopaminergic neuron phenotype in the midbrain by sonic hedgehog protein. Nature Med 2:1184–1188.

Wilkinson, D. G. (1992). Whole mount in situ hybridization of vertebrate embryos.

In In Situ Hybridization: A Practical Approach, D. G. Wilkinson, ed. (Oxford: IRL Press), pp. 75–83.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid encoding a polypeptide comprising a hedgehog polypeptide which is at least 98 percent identical to either SEQ ID NO: 17 or an N-terminal fragment of SEQ ID NO: 17 having a molecular weight of about 19 kD, which hedgehog polypeptide binds to a patched protein or promotes proliferation of testicular germ line cells.

2. An isolated expression vector, capable of replicating in at least one of a prokaryotic cell and a eukaryotic cell, comprising the nucleic acid of claim 1.

3. An isolated and/or non-human and/or ex-vivo host cell transfected with the expression vector of claim 2 and expressing said recombinant polypeptide.

4. A recombinant transfection system, comprising
  (i) a gene construct including the nucleic acid of claim 1, operably linked to a transcriptional regulatory sequence for causing expression of the hedgehog polypeptide in eukaryotic cells, and
  (ii) a gene delivery composition for delivering said gene construct to a cell and causing the cell to be transfected with said gene construct.

5. The recombinant transfection system of claim 4, wherein the gene delivery composition is selected from a group consisting of a recombinant viral particle, a liposome, and a poly-cationic nucleic acid binding agent.

6. An isolated nucleic acid comprising a nucleotide sequence which encodes a polypeptide of SEQ ID NO. 17 or an N-terminal fragment thereof having a molecular weight of about 19 kD, which polypeptide binds to a patched protein.

7. A nucleic acid according to claim 6, further comprising a transcriptional regulatory sequence operably linked to said nucleotide sequence.

8. An isolated expression vector, configured for replication in at least one of a prokaryotic cell and a eukaryotic cell, comprising the nucleic acid of claim 6.

9. An isolated and/or non-human and/or ex-vivo host cell transfected with the expression vector of claim 8.

10. The nucleic acid of claim 6, comprising the nucleotide sequence of SEQ ID NO. 8.

11. An isolated nucleic acid comprising the nucleotide sequence of SEQ ID NO: 8 or its complementary nucleotide sequence.

12. An isolated expression vector comprising the nucleic acid of claim 11.

13. The nucleic acid of claim 11, which encodes an amino acid sequence of SEQ ID NO: 17.

14. An isolated and/or non-human and/or ex-vivo host cell transfected with the expression vector of claim 11 and expressing said recombinant polypeptide.

15. An isolated and/or non-human and/or ex-vivo host cell transfected with the expression vector of claim 12 and expressing said recombinant polypeptide.

16. The nucleic acid of claim 6, which nucleic acid encodes a polypeptide including amino acids 23–198 of SEQ ID NO: 17.

17. The nucleic acid of claim 6, which nucleic acid encodes a polypeptide including SEQ ID NO: 17.

18. An isolated nucleic acid encoding a polypeptide consisting of a hedgehog polypeptide which is at least 98 percent identical to either SEQ ID NO: 17 or an N-terminal fragment thereof having a molecular weight of about 19 kD, which hedgehog polypeptide binds to a patched protein or promotes proliferation of testicular germ line cells.

19. An isolated nucleic acid encoding a polypeptide comprising a hedgehog amino acid sequence which is at least 98 percent identical to SEQ ID NO: 17, which hedgehog amino acid sequence binds to a patched protein or promotes proliferation of testicular germ line cells.

20. An isolated polypeptide comprising a hedgehog polypeptide which is at least 98 percent identical to either SEQ ID NO: 17 or an N-terminal fragment of SEQ ID NO: 17 having a molecular weight of about 19 kD, which hedgehog polypeptide binds to a patched protein or promotes proliferation of testicular germ line cells.

21. The polypeptide of claim 20, which polypeptide includes amino acids 23–198 of SEQ ID NO: 17.

22. The polypeptide of claim 20, which polypeptide includes the amino acid sequence of SEQ ID NO: 17.

23. An isolated polypeptide comprising the amino acid sequence of SEQ ID NO. 17 or an N-terminal fragment thereof having a molecular weight of about 19 kD, which polypeptide binds to a patched protein.

24. The polypeptide of claim 23, wherein the polypeptide comprises the amino acid sequence of SEQ ID NO: 17.

25. An isolated polypeptide consisting of a hedgehog polypeptide which is at least 98 percent identical to either SEQ ID NO: 17 or an N-terminal fragment thereof having a molecular weight of about 19 kD, which hedgehog polypeptide binds to a patched protein or promotes proliferation of testicular germ line cells.

26. An isolated polypeptide comprising a hedgehog amino acid sequence which is at least 98 percent identical to SEQ ID NO: 17, which hedgehog amino acid sequence binds to a patched protein or promotes proliferation of testicular germ line cells.

* * * * *

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 1277 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..1275

(xi) SEQUENCE DESCRIPTION: SEQ ID NO: 1:

-continued

```
ATG GTC GAA ATG CTG CTG TTG ACA AGA ATT CTC TTG GTG GGC TTC ATC         48
Met Val Glu Met Leu Leu Leu Thr Arg Ile Leu Leu Val Gly Phe Ile
  1               5                  10                  15

TGC GCT CTT TTA GTC TCC TCT GGG CTG ACT TGT GGA CCA GGC AGG GGC         96
Cys Ala Leu Leu Val Ser Ser Gly Leu Thr Cys Gly Pro Gly Arg Gly
             20                  25                  30

ATT GGA AAA AGG AGG CAC CCC AAA AAG CTG ACC CCG TTA GCC TAT AAG        144
Ile Gly Lys Arg Arg His Pro Lys Lys Leu Thr Pro Leu Ala Tyr Lys
         35                  40                  45

CAG TTT ATT CCC AAT GTG GCA GAG AAG ACC CTA GGG GCC AGT GGA AGA        192
Gln Phe Ile Pro Asn Val Ala Glu Lys Thr Leu Gly Ala Ser Gly Arg
     50                  55                  60

TAT GAA GGG AAG ATC ACA AGA AAC TCC GAG AGA TTT AAA GAA CTA ACC        240
Tyr Glu Gly Lys Ile Thr Arg Asn Ser Glu Arg Phe Lys Glu Leu Thr
 65                  70                  75                  80

CCA AAT TAC AAC CCT GAC ATT ATT TTT AAG GAT GAA GAG AAC ACG GGA        288
Pro Asn Tyr Asn Pro Asp Ile Ile Phe Lys Asp Glu Glu Asn Thr Gly
                 85                  90                  95

GCT GAC AGA CTG ATG ACT CAG CGC TGC AAG GAC AAG CTG AAT GCC CTG        336
Ala Asp Arg Leu Met Thr Gln Arg Cys Lys Asp Lys Leu Asn Ala Leu
                100                 105                 110

GCG ATC TCG GTG ATG AAC CAG TGG CCC GGG GTG AAG CTG CGG GTG ACC        384
Ala Ile Ser Val Met Asn Gln Trp Pro Gly Val Lys Leu Arg Val Thr
            115                 120                 125

GAG GGC TGG GAC GAG GAT GGC CAT CAC TCC GAG GAA TCG CTG CAC TAC        432
Glu Gly Trp Asp Glu Asp Gly His His Ser Glu Glu Ser Leu His Tyr
        130                 135                 140

GAG GGT CGC GCC GTG GAC ATC ACC ACG TCG GAT CGG GAC CGC AGC AAG        480
Glu Gly Arg Ala Val Asp Ile Thr Thr Ser Asp Arg Asp Arg Ser Lys
145                 150                 155                 160

TAC GGA ATG CTG GCC CGC CTC GCC GTC GAG GCC GGC TTC GAC TGG GTC        528
Tyr Gly Met Leu Ala Arg Leu Ala Val Glu Ala Gly Phe Asp Trp Val
                165                 170                 175

TAC TAC GAG TCC AAG GCG CAC ATC CAC TGC TCC GTC AAA GCA GAA AAC        576
Tyr Tyr Glu Ser Lys Ala His Ile His Cys Ser Val Lys Ala Glu Asn
                180                 185                 190

TCA GTG GCA GCG AAA TCA GGA GGC TGC TTC CCT GGC TCA GCC ACA GTG        624
Ser Val Ala Ala Lys Ser Gly Gly Cys Phe Pro Gly Ser Ala Thr Val
            195                 200                 205

CAC CTG GAG CAT GGA GGC ACC AAG CTG GTG AAG GAC CTG AGC CCT GGG        672
His Leu Glu His Gly Gly Thr Lys Leu Val Lys Asp Leu Ser Pro Gly
        210                 215                 220

GAC CGC GTG CTG GCT GCT GAC GCG GAC GGC CGG CTG CTC TAC AGT GAC        720
Asp Arg Val Leu Ala Ala Asp Ala Asp Gly Arg Leu Leu Tyr Ser Asp
225                 230                 235                 240

TTC CTC ACC TTC CTC GAC CGG ATG GAC AGC TCC CGA AAG CTC TTC TAC        768
Phe Leu Thr Phe Leu Asp Arg Met Asp Ser Ser Arg Lys Leu Phe Tyr
                245                 250                 255

GTC ATC GAG ACG CGG CAG CCC CGG GCC CGG CTG CTA CTG ACG GCG GCC        816
Val Ile Glu Thr Arg Gln Pro Arg Ala Arg Leu Leu Leu Thr Ala Ala
                260                 265                 270

CAC CTG CTC TTT GTG GCC CCC CAG CAC AAC CAG TCG GAG GCC ACA GGG        864
His Leu Leu Phe Val Ala Pro Gln His Asn Gln Ser Glu Ala Thr Gly
            275                 280                 285

TCC ACC AGT GGC CAG GCG CTC TTC GCC AGC AAC GTG AAG CCT GGC CAA        912
Ser Thr Ser Gly Gln Ala Leu Phe Ala Ser Asn Val Lys Pro Gly Gln
        290                 295                 300

CGT GTC TAT GTG CTG GGC GAG GGC GGG CAG CAG CTG CTG CCG GCG TCT        960
Arg Val Tyr Val Leu Gly Glu Gly Gly Gln Gln Leu Leu Pro Ala Ser
305                 310                 315                 320
```

```
GTC CAC AGC GTC TCA TTG CGG GAG GAG GCG TCC GGA GCC TAC GCC CCA     1008
Val His Ser Val Ser Leu Arg Glu Glu Ala Ser Gly Ala Tyr Ala Pro
            325                 330                 335

CTC ACC GCC CAG GGC ACC ATC CTC ATC AAC CGG GTG TTG GCC TCC TGC     1056
Leu Thr Ala Gln Gly Thr Ile Leu Ile Asn Arg Val Leu Ala Ser Cys
            340                 345                 350

TAC GCC GTC ATC GAG GAG CAC AGT TGG GCC CAT TGG GCC TTC GCA CCA     1104
Tyr Ala Val Ile Glu Glu His Ser Trp Ala His Trp Ala Phe Ala Pro
            355                 360                 365

TTC CGC TTG GCT CAG GGG CTG CTG GCC GCC CTC TGC CCA GAT GGG GCC     1152
Phe Arg Leu Ala Gln Gly Leu Leu Ala Ala Leu Cys Pro Asp Gly Ala
        370                 375                 380

ATC CCT ACT GCC GCC ACC ACC ACC ACT GGC ATC CAT TGG TAC TCA CGG     1200
Ile Pro Thr Ala Ala Thr Thr Thr Thr Gly Ile His Trp Tyr Ser Arg
385                 390                 395                 400

CTC CTC TAC CGC ATC GGC AGC TGG GTG CTG GAT GGT GAC GCG CTG CAT     1248
Leu Leu Tyr Arg Ile Gly Ser Trp Val Leu Asp Gly Asp Ala Leu His
            405                 410                 415

CCG CTG GGC ATG GTG GCA CCG GCC AGC TG                              1277
Pro Leu Gly Met Val Ala Pro Ala Ser
            420                 425

(2) INFORMATION FOR SEQ ID NO: 2:

(i) SEQUENCE CHARACTERISTICS:
        (A) LENGTH: 1190 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1191

(xi) SEQUENCE DESCRIPTION: SEQ ID NO: 2:

ATG GCT CTG CCG GCC AGT CTG TTG CCC CTG TGC TGC TTG GCA CTC TTG     48
Met Ala Leu Pro Ala Ser Leu Leu Pro Leu Cys Cys Leu Ala Leu Leu
1               5                   10                  15

GCA CTA TCT GCC CAG AGC TGC GGG CCG GGC CGA GGA CCG GTT GGC CGG     96
Ala Leu Ser Ala Gln Ser Cys Gly Pro Gly Arg Gly Pro Val Gly Arg
                20                  25                  30

CGG CGT TAT GTG CGC AAG CAA CTT GTG CCT CTG CTA TAC AAG CAG TTT     144
Arg Arg Tyr Val Arg Lys Gln Leu Val Pro Leu Leu Tyr Lys Gln Phe
            35                  40                  45

GTG CCC AGT ATG CCC GAG CGG ACC CTG GGC GCG AGT GGG CCA GCG GAG     192
Val Pro Ser Met Pro Glu Arg Thr Leu Gly Ala Ser Gly Pro Ala Glu
        50                  55                  60

GGG AGG GTA ACA AGG GGG TCG GAG CGC TTC CGG GAC CTC GTA CCC AAC     240
Gly Arg Val Thr Arg Gly Ser Glu Arg Phe Arg Asp Leu Val Pro Asn
65                  70                  75                  80

TAC AAC CCC GAC ATA ATC TTC AAG GAT GAG GAG AAC AGC GGC GCA GAC     288
Tyr Asn Pro Asp Ile Ile Phe Lys Asp Glu Glu Asn Ser Gly Ala Asp
                85                  90                  95

CGC CTG ATG ACA GAG CGT TGC AAA GAG CGG GTG AAC GCT CTA GCC ATC     336
Arg Leu Met Thr Glu Arg Cys Lys Glu Arg Val Asn Ala Leu Ala Ile
            100                 105                 110

GCG GTG ATG AAC ATG TGG CCC GGA GTA CGC CTA CGT GTG ACT GAA GGC     384
Ala Val Met Asn Met Trp Pro Gly Val Arg Leu Arg Val Thr Glu Gly
        115                 120                 125

TGG GAC GAG GAC GGC CAC CAC GCA CAG GAT TCA CTC CAC TAC GAA GGC     432
```

```
              Trp Asp Glu Asp Gly His His Ala Gln Asp Ser Leu His Tyr Glu Gly
              130                 135                 140

CGT GCC TTG GAC ATC ACC ACG TCT GAC CGT GAC CGT AAT AAG TAT GGT            480
Arg Ala Leu Asp Ile Thr Thr Ser Asp Arg Asp Arg Asn Lys Tyr Gly
145                 150                 155                 160

TTG TTG GCG CGC CTA GCT GTG GAA GCC GGA TTC GAC TGG GTC TAC TAC            528
Leu Leu Ala Arg Leu Ala Val Glu Ala Gly Phe Asp Trp Val Tyr Tyr
                165                 170                 175

GAG TCC CGC AAC CAC ATC CAC GTA TCG GTC AAA GCT GAT AAC TCA CTG            576
Glu Ser Arg Asn His Ile His Val Ser Val Lys Ala Asp Asn Ser Leu
                180                 185                 190

GCG GTC CGA GCC GGA GGC TGC TTT CCG GGA AAT GCC ACG GTG CGC TTG            624
Ala Val Arg Ala Gly Gly Cys Phe Pro Gly Asn Ala Thr Val Arg Leu
                195                 200                 205

CGG AGC GGC GAA CGG AAG GGG CTG AGG GAA CTA CAT CGT GGT GAC TGG            672
Arg Ser Gly Glu Arg Lys Gly Leu Arg Glu Leu His Arg Gly Asp Trp
210                 215                 220

GTA CTG GCC GCT GAT GCA GCG GGC CGA GTG GTA CCC ACG CCA GTG CTG            720
Val Leu Ala Ala Asp Ala Ala Gly Arg Val Val Pro Thr Pro Val Leu
225                 230                 235                 240

CTC TTC CTG GAC CGG GAT CTG CAG CGC CGC GCC TCG TTC GTG GCT GTG            768
Leu Phe Leu Asp Arg Asp Leu Gln Arg Arg Ala Ser Phe Val Ala Val
                245                 250                 255

GAG ACC GAG CGG CCT CCG CGC AAA CTG TTG CTC ACA CCC TGG CAT CTG            816
Glu Thr Glu Arg Pro Pro Arg Lys Leu Leu Leu Thr Pro Trp His Leu
                260                 265                 270

GTG TTC GCT GCT CGC GGG CCA GCG CCT GCT CCA GGT GAC TTT GCA CCG            864
Val Phe Ala Ala Arg Gly Pro Ala Pro Ala Pro Gly Asp Phe Ala Pro
                275                 280                 285

GTG TTC GCG CGC CGC TTA CGT GCT GGC GAC TCG GTG CTG GCT CCC GGC            912
Val Phe Ala Arg Arg Leu Arg Ala Gly Asp Ser Val Leu Ala Pro Gly
290                 295                 300

GGG GAC GCG CTC CAG CCG GCG CGC GTA GCC CGC GTG GCG CGC GAG GAA            960
Gly Asp Ala Leu Gln Pro Ala Arg Val Ala Arg Val Ala Arg Glu Glu
305                 310                 315                 320

GCC GTG GGC GTG TTC GCA CCG CTC ACT GCG CAC GGG ACG CTG CTG GTC           1008
Ala Val Gly Val Phe Ala Pro Leu Thr Ala His Gly Thr Leu Leu Val
                325                 330                 335

AAC GAC GTC CTC GCC TCC TGC TAC GCG GTT CTA GAG AGT CAC CAG TGG           1056
Asn Asp Val Leu Ala Ser Cys Tyr Ala Val Leu Glu Ser His Gln Trp
                340                 345                 350

GCC CAC CGC GCC TTC GCC CCT TTG CGG CTG CTG CAC GCG CTC GGG GCT           1104
Ala His Arg Ala Phe Ala Pro Leu Arg Leu Leu His Ala Leu Gly Ala
                355                 360                 365

CTG CTC CCT GGG GGT GCA GTC CAG CCG ACT GGC ATG CAT TGG TAC TCT           1152
Leu Leu Pro Gly Gly Ala Val Gln Pro Thr Gly Met His Trp Tyr Ser
370                 375                 380

CGC CTC CTT TAC CGC TTG GCC GAG GAG TTA ATG GGC TG                        1190
Arg Leu Leu Tyr Arg Leu Ala Glu Glu Leu Met Gly
385                 390                 395

(2) INFORMATION FOR SEQ ID NO: 3:

(i) SEQUENCE CHARACTERISTICS:
        (A) LENGTH: 1281 base pairs
        (B) TYPE: nucleic acid
        (C) STRANDEDNESS: both
        (D) TOPOLOGY: linear (ii) MOLECULE TYPE: cDNA (ix) FEATURE:
```

(A) NAME/KEY: CDS
(B) LOCATION: 1..1233

(xi) SEQUENCE DESCRIPTION: SEQ ID NO: 3:

```
ATG TCT CCC GCC TGG CTC CGG CCC CGA CTG CGG TTC TGT CTG TTC CTG        48
Met Ser Pro Ala Trp Leu Arg Pro Arg Leu Arg Phe Cys Leu Phe Leu
 1               5                  10                  15

CTG CTG CTG CTT CTG GTG CCG GCG GCG CGG GGC TGC GGG CCG GGC CGG        96
Leu Leu Leu Leu Leu Val Pro Ala Ala Arg Gly Cys Gly Pro Gly Arg
                 20                  25                  30

GTG GTG GGC AGC CGC CGG AGG CCG CCT CGC AAG CTC GTG CCT CTT GCC       144
Val Val Gly Ser Arg Arg Arg Pro Pro Arg Lys Leu Val Pro Leu Ala
             35                  40                  45

TAC AAG CAG TTC AGC CCC AAC GTG CCG GAG AAG ACC CTG GGC GCC AGC       192
Tyr Lys Gln Phe Ser Pro Asn Val Pro Glu Lys Thr Leu Gly Ala Ser
         50                  55                  60

GGG CGC TAC GAA GGC AAG ATC GCG CGC AGC TCT GAG CGC TTC AAA GAG       240
Gly Arg Tyr Glu Gly Lys Ile Ala Arg Ser Ser Glu Arg Phe Lys Glu
 65                  70                  75                  80

CTC ACC CCC AAC TAC AAT CCC GAC ATC ATC TTC AAG GAC GAG GAG AAC       288
Leu Thr Pro Asn Tyr Asn Pro Asp Ile Ile Phe Lys Asp Glu Glu Asn
                 85                  90                  95

ACG GGT GCC GAC CGC CTC ATG ACC CAG CGC TGC AAG GAC CGT CTG AAC       336
Thr Gly Ala Asp Arg Leu Met Thr Gln Arg Cys Lys Asp Arg Leu Asn
            100                 105                 110

TCA CTG GCC ATC TCT GTC ATG AAC CAG TGG CCT GGT GTG AAA CTG CGG       384
Ser Leu Ala Ile Ser Val Met Asn Gln Trp Pro Gly Val Lys Leu Arg
        115                 120                 125

GTG ACC GAA GGC CGG GAT GAA GAT GGC CAT CAC TCA GAG GAG TCT TTA       432
Val Thr Glu Gly Arg Asp Glu Asp Gly His His Ser Glu Glu Ser Leu
130                 135                 140

CAC TAT GAG GGC CGC GCG GTG GAT ATC ACC ACC TCA GAC CGT GAC CGA       480
His Tyr Glu Gly Arg Ala Val Asp Ile Thr Thr Ser Asp Arg Asp Arg
145                 150                 155                 160

AAT AAG TAT GGA CTG CTG GCG CGC TTA GCA GTG GAG GCC GGC TTC GAC       528
Asn Lys Tyr Gly Leu Leu Ala Arg Leu Ala Val Glu Ala Gly Phe Asp
                165                 170                 175

TGG GTG TAT TAC GAG TCC AAG GCC CAC GTG CAT TGC TCT GTC AAG TCT       576
Trp Val Tyr Tyr Glu Ser Lys Ala His Val His Cys Ser Val Lys Ser
            180                 185                 190

GAG CAT TCG GCC GCT GCC AAG ACA GGT GGC TGC TTT CCT GCC GGA GCC       624
Glu His Ser Ala Ala Ala Lys Thr Gly Gly Cys Phe Pro Ala Gly Ala
        195                 200                 205

CAG GTG CGC CTA GAG AAC GGG GAG CGT GTG GCC CTG TCA GCT GTA AAG       672
Gln Val Arg Leu Glu Asn Gly Glu Arg Val Ala Leu Ser Ala Val Lys
    210                 215                 220

CCA GGA GAC CGG GTG CTG GCC ATG GGG GAG GAT GGG ACC CCC ACC TTC       720
Pro Gly Asp Arg Val Leu Ala Met Gly Glu Asp Gly Thr Pro Thr Phe
225                 230                 235                 240

AGT GAT GTG CTT ATT TTC CTG GAC CGC GAG CCA AAC CGG CTG AGA GCT       768
Ser Asp Val Leu Ile Phe Leu Asp Arg Glu Pro Asn Arg Leu Arg Ala
                245                 250                 255

TTC CAG GTC ATC GAG ACT CAG GAT CCT CCG CGT CGG CTG GCG CTC ACG       816
Phe Gln Val Ile Glu Thr Gln Asp Pro Pro Arg Arg Leu Ala Leu Thr
            260                 265                 270

CCT GCC CAC CTG CTC TTC ATT GCG GAC AAT CAT ACA GAA CCA GCA GCC       864
Pro Ala His Leu Leu Phe Ile Ala Asp Asn His Thr Glu Pro Ala Ala
        275                 280                 285

CAC TTC CGG GCC ACA TTT GCC AGC CAT GTG CAA CCA GGC CAA TAT GTG       912
His Phe Arg Ala Thr Phe Ala Ser His Val Gln Pro Gly Gln Tyr Val
```

```
                290                     295                     300
CTG GTA TCA GGG GTA CCA GGC CTC CAG CCT GCT CGG GTG GCA GCT GTC      960
Leu Val Ser Gly Val Pro Gly Leu Gln Pro Ala Arg Val Ala Ala Val
305                 310                 315                 320

TCC ACC CAC GTG GCC CTT GGG TCC TAT GCT CCT CTC ACA AGG CAT GGG     1008
Ser Thr His Val Ala Leu Gly Ser Tyr Ala Pro Leu Thr Arg His Gly
                325                 330                 335

ACA CTT GTG GTG GAG GAT GTG GTG GCC TCC TGC TTT GCA GCT GTG GCT     1056
Thr Leu Val Val Glu Asp Val Val Ala Ser Cys Phe Ala Ala Val Ala
                340                 345                 350

GAC CAC CAT CTG GCT CAG TTG GCC TTC TGG CCC CTG CGA CTG TTT CCC     1104
Asp His His Leu Ala Gln Leu Ala Phe Trp Pro Leu Arg Leu Phe Pro
            355                 360                 365

AGT TTG GCA TGG GGC AGC TGG ACC CCA AGT GAG GGT GTT CAC TCC TAC     1152
Ser Leu Ala Trp Gly Ser Trp Thr Pro Ser Glu Gly Val His Ser Tyr
370                 375                 380

CCT CAG ATG CTC TAC CGC CTG GGG CGT CTC TTG CTA GAA GAG AGC ACC     1200
Pro Gln Met Leu Tyr Arg Leu Gly Arg Leu Leu Leu Glu Glu Ser Thr
385                 390                 395                 400

TTC CAT CCA CTG GGC ATG TCT GGG GCA GGA AGC TGAAGGGACT CTAACCAC     1253
Phe His Pro Leu Gly Met Ser Gly Ala Gly Ser
                405                 410

CCCTCCTGGA ACTGCTGTGC GTGGATCC                                      1281

(2) INFORMATION FOR SEQ ID NO: 4:

(i) SEQUENCE CHARACTERISTICS:
          (A) LENGTH: 1313 base pairs
          (B) TYPE: nucleic acid
          (C) STRANDEDNESS: both
          (D) TOPOLOGY: linear (ii) MOLECULE TYPE: cDNA (ix) FEATURE:
          (A) NAME/KEY: CDS
          (B) LOCATION: 1..1314

(xi) SEQUENCE DESCRIPTION: SEQ ID NO: 4:

ATG CTG CTG CTG CTG GCC AGA TGT TTT CTG GTG ATC CTT GCT TCC TCG       48
Met Leu Leu Leu Leu Ala Arg Cys Phe Leu Val Ile Leu Ala Ser Ser
1               5                   10                  15

CTG CTG GTG TGC CCC GGG CTG GCC TGT GGG CCC GGC AGG GGG TTT GGA       96
Leu Leu Val Cys Pro Gly Leu Ala Cys Gly Pro Gly Arg Gly Phe Gly
                20                  25                  30

AAG AGG CGG CAC CCC AAA AAG CTG ACC CCT TTA GCC TAC AAG CAG TTT      144
Lys Arg Arg His Pro Lys Lys Leu Thr Pro Leu Ala Tyr Lys Gln Phe
            35                  40                  45

ATT CCC AAC GTA GCC GAG AAG ACC CTA GGG GCC AGC GGC AGA TAT GAA      192
Ile Pro Asn Val Ala Glu Lys Thr Leu Gly Ala Ser Gly Arg Tyr Glu
50                  55                  60

GGG AAG ATC ACA AGA AAC TCC GAA CGA TTT AAG GAA CTC ACC CCC AAT      240
Gly Lys Ile Thr Arg Asn Ser Glu Arg Phe Lys Glu Leu Thr Pro Asn
65                  70                  75                  80

TAC AAC CCC GAC ATC ATA TTT AAG GAT GAG GAA AAC ACG GGA GCA GAC      288
Tyr Asn Pro Asp Ile Ile Phe Lys Asp Glu Glu Asn Thr Gly Ala Asp
                85                  90                  95

CGG CTG ATG ACT CAG AGG TGC AAA GAC AAG TTA AAT GCC TTG GCC ATC      336
Arg Leu Met Thr Gln Arg Cys Lys Asp Lys Leu Asn Ala Leu Ala Ile
            100                 105                 110

TCT GTG ATG AAC CAG TGG CCT GGA GTG AGG CTG CGA GTG ACC GAG GGC      384
Ser Val Met Asn Gln Trp Pro Gly Val Arg Leu Arg Val Thr Glu Gly
```

```
                    115                  120                        125
TGG GAT GAG GAC GGC CAT CAT TCA GAG GAG TCT CTA CAC TAT GAG GGT          432
Trp Asp Glu Asp Gly His His Ser Glu Glu Ser Leu His Tyr Glu Gly
        130                 135                 140

CGA GCA GTG GAC ATC ACC ACG TCC GAC CGG GAC CGC AGC AAG TAC GGC          480
Arg Ala Val Asp Ile Thr Thr Ser Asp Arg Asp Arg Ser Lys Tyr Gly
145                 150                 155                 160

ATG CTG GCT CGC CTG GCT GTG GAA GCA GGT TTC GAC TGG GTC TAC TAT          528
Met Leu Ala Arg Leu Ala Val Glu Ala Gly Phe Asp Trp Val Tyr Tyr
                165                 170                 175

GAA TCC AAA GCT CAC ATC CAC TGT TCT GTG AAA GCA GAG AAC TCC GTG          576
Glu Ser Lys Ala His Ile His Cys Ser Val Lys Ala Glu Asn Ser Val
        180                 185                 190

GCG GCC AAA TCC GGC GGC TGT TTC CCG GGA TCC GCC ACC GTG CAC CTG          624
Ala Ala Lys Ser Gly Gly Cys Phe Pro Gly Ser Ala Thr Val His Leu
            195                 200                 205

GAG CAG GGC GGC ACC AAG CTG GTG AAG GAC TTA CGT CCC GGA GAC CGC          672
Glu Gln Gly Gly Thr Lys Leu Val Lys Asp Leu Arg Pro Gly Asp Arg
Gln Gly Gly Thr Lys Leu Val Lys Asp Leu Arg Pro Gly Asp Arg
210                 215                 220

GTG CTG GCG GCT GAC GAC CAG GGC CGG CTG CTC TAC AGC GAC TTC CTC          720
Val Leu Ala Ala Asp Asp Gln Gly Arg Leu Leu Tyr Ser Asp Phe Leu
225                 230                 235                 240

ACC TTC CTG GAC CGC GAC GAA GGC GCC AAG AAG GTC TTC TAC GTG ATC          768
Thr Phe Leu Asp Arg Asp Glu Gly Ala Lys Lys Val Phe Tyr Val Ile
                245                 250                 255

GAG ACG CTG GAG CCG CGC GAG CGC CTG CTG CTC ACC GCC GCG CAC CTG          816
Glu Thr Leu Glu Pro Arg Glu Arg Leu Leu Leu Thr Ala Ala His Leu
            260                 265                 270

CTC TTC GTG GCG CCG CAC AAC GAC TCG GGG CCC ACG CCC GGG CCA AGC          864
Leu Phe Val Ala Pro His Asn Asp Ser Gly Pro Thr Pro Gly Pro Ser
        275                 280                 285

GCG CTC TTT GCC AGC CGC GTG CGC CCC GGG CAG CGC GTG TAC GTG GTG          912
Ala Leu Phe Ala Ser Arg Val Arg Pro Gly Gln Arg Val Tyr Val Val
    290                 295                 300

GCT GAA CGC GGC GGG GAC CGC CGG CTG CTG CCC GCC GCG GTG CAC AGC          960
Ala Glu Arg Gly Gly Asp Arg Arg Leu Leu Pro Ala Ala Val His Ser
305                 310                 315                 320

GTG ACG CTG CGA GAG GAG GAG GCG GGC GCG TAC GCG CCG CTC ACG GCG         1008
Val Thr Leu Arg Glu Glu Glu Ala Gly Ala Tyr Ala Pro Leu Thr Ala
                325                 330                 335

CAC GGC ACC ATT CTC ATC AAC CGG GTG CTC GCC TCG TGC TAC GCT GTC         1056
His Gly Thr Ile Leu Ile Asn Arg Val Leu Ala Ser Cys Tyr Ala Val
            340                 345                 350

ATC GAG GAG CAC AGC TGG GCA CAC CGG GCC TTC GCG CCT TTC CGC CTG         1104
Ile Glu Glu His Ser Trp Ala His Arg Ala Phe Ala Pro Phe Arg Leu
        355                 360                 365

GCG CAC GCG CTG CTG GCC GCG CTG GCA CCC GCC CGC ACG GAC GGC GGG         1152
Ala His Ala Leu Leu Ala Ala Leu Ala Pro Ala Arg Thr Asp Gly Gly
    370                 375                 380

GGC GGG GGC AGC ATC CCT GCA GCG CAA TCT GCA ACG GAA GCG AGG GGC         1200
Gly Gly Gly Ser Ile Pro Ala Ala Gln Ser Ala Thr Glu Ala Arg Gly
385                 390                 395                 400

GCG GAG CCG ACT GCG GGC ATC CAC TGG TAC TCG CAG CTG CTC TAC CAC         1248
Ala Glu Pro Thr Ala Gly Ile His Trp Tyr Ser Gln Leu Leu Tyr His
                405                 410                 415

ATT GGC ACC TGG CTG TTG GAC AGC GAG ACC ATG CAT CCC TTG GGA ATG         1296
Ile Gly Thr Trp Leu Leu Asp Ser Glu Thr Met His Pro Leu Gly Met
            420                 425                 430

GCG GTC AAG TCC AGC TG                                                  1313
```

Ala Val Lys Ser Ser
         435

(2) INFORMATION FOR SEQ ID NO: 5:

(i) SEQUENCE CHARACTERISTICS:
        (A) LENGTH: 1256 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1257

(xi) SEQUENCE DESCRIPTION: SEQ ID NO: 5:

```
ATG CGG CTT TTG ACG AGA GTG CTG CTG GTG TCT CTT CTC ACT CTG TCC      48
Met Arg Leu Leu Thr Arg Val Leu Leu Val Ser Leu Leu Thr Leu Ser
 1               5                  10                  15

TTG GTG GTG TCC GGA CTG GCC TGC GGT CCT GGC AGA GGC TAC GGC AGA      96
Leu Val Val Ser Gly Leu Ala Cys Gly Pro Gly Arg Gly Tyr Gly Arg
             20                  25                  30

AGA AGA CAT CCG AAG AAG CTG ACA CCT CTC GCC TAC AAG CAG TTC ATA     144
Arg Arg His Pro Lys Lys Leu Thr Pro Leu Ala Tyr Lys Gln Phe Ile
         35                  40                  45

CCT AAT GTC GCG GAG AAG ACC TTA GGG GCC AGC GGC AGA TAC GAG GGC     192
Pro Asn Val Ala Glu Lys Thr Leu Gly Ala Ser Gly Arg Tyr Glu Gly
 50                  55                  60

AAG ATA ACG CGC AAT TCG GAG AGA TTT AAA GAA CTT ACT CCA AAT TAC     240
Lys Ile Thr Arg Asn Ser Glu Arg Phe Lys Glu Leu Thr Pro Asn Tyr
 65                  70                  75                  80

AAT CCC GAC ATT ATC TTT AAG GAT GAG GAG AAC ACG GGA GCG GAC AGG     288
Asn Pro Asp Ile Ile Phe Lys Asp Glu Glu Asn Thr Gly Ala Asp Arg
                 85                  90                  95

CTC ATG ACA CAG AGA TGC AAA GAC AAG CTG AAC TCG CTG GCC ATC TCT     336
Leu Met Thr Gln Arg Cys Lys Asp Lys Leu Asn Ser Leu Ala Ile Ser
            100                 105                 110

GTA ATG AAC CAC TGG CCA GGG GTT AAG CTG CGT GTG ACA GAG GGC TGG     384
Val Met Asn His Trp Pro Gly Val Lys Leu Arg Val Thr Glu Gly Trp
        115                 120                 125

GAT GAG GAC GGT CAC CAT TTT GAA GAA TCA CTC CAC TAC GAG GGA AGA     432
Asp Glu Asp Gly His His Phe Glu Glu Ser Leu His Tyr Glu Gly Arg
    130                 135                 140

GCT GTT GAT ATT ACC ACC TCT GAC CGA GAC AAG AGC AAA TAC GGG ACA     480
Ala Val Asp Ile Thr Thr Ser Asp Arg Asp Lys Ser Lys Tyr Gly Thr
145                 150                 155                 160

CTG TCT CGC CTA GCT GTG GAG GCT GGA TTT GAC TGG GTC TAT TAC GAG     528
Leu Ser Arg Leu Ala Val Glu Ala Gly Phe Asp Trp Val Tyr Tyr Glu
                165                 170                 175

TCC AAA GCC CAC ATT CAT TGC TCT GTC AAA GCA GAA AAT TCG GTT GCT     576
Ser Lys Ala His Ile His Cys Ser Val Lys Ala Glu Asn Ser Val Ala
            180                 185                 190

GCG AAA TCT GGG GGC TGT TTC CCA GGT TCG GCT CTG GTC TCG CTC CAG     624
Ala Lys Ser Gly Gly Cys Phe Pro Gly Ser Ala Leu Val Ser Leu Gln
        195                 200                 205

GAC GGA GGA CAG AAG GCC GTG AAG GAC CTG AAC CCC GGA GAC AAG GTG     672
Asp Gly Gly Gln Lys Ala Val Lys Asp Leu Asn Pro Gly Asp Lys Val
    210                 215                 220

CTG GCG GCA GAC AGC GCG GGA AAC CTG GTG TTC AGC GAC TTC ATC ATG     720
Leu Ala Ala Asp Ser Ala Gly Asn Leu Val Phe Ser Asp Phe Ile Met
225                 230                 235                 240
```

```
TTC ACA GAC CGA GAC TCC ACG ACG CGA CGT GTG TTT TAC GTC ATA GAA        768
Phe Thr Asp Arg Asp Ser Thr Thr Arg Arg Val Phe Tyr Val Ile Glu
                245                 250                 255

ACG CAA GAA CCC GTT GAA AAG ATC ACC CTC ACC GCC GCT CAC CTC CTT        816
Thr Gln Glu Pro Val Glu Lys Ile Thr Leu Thr Ala Ala His Leu Leu
            260                 265                 270

TTT GTC CTC GAC AAC TCA ACG GAA GAT CTC CAC ACC ATG ACC GCC GCG        864
Phe Val Leu Asp Asn Ser Thr Glu Asp Leu His Thr Met Thr Ala Ala
        275                 280                 285

TAT GCC AGC AGT GTC AGA GCC GGA CAA AAG GTG ATG GTT GTT GAT GAT        912
Tyr Ala Ser Ser Val Arg Ala Gly Gln Lys Val Met Val Val Asp Asp
    290                 295                 300

AGC GGT CAG CTT AAA TCT GTC ATC GTG CAG CGG ATA TAC ACG GAG GAG        960
Ser Gly Gln Leu Lys Ser Val Ile Val Gln Arg Ile Tyr Thr Glu Glu
305                 310                 315                 320

CAG CGG GGC TCG TTC GCA CCA GTG ACT GCA CAT GGG ACC ATT GTG GTC       1008
Gln Arg Gly Ser Phe Ala Pro Val Thr Ala His Gly Thr Ile Val Val
                325                 330                 335

GAC AGA ATA CTG GCG TCC TGT TAC GCC GTA ATA GAG GAC CAG GGG CTT       1056
Asp Arg Ile Leu Ala Ser Cys Tyr Ala Val Ile Glu Asp Gln Gly Leu
            340                 345                 350

GCG CAT TTG GCC TTC GCG CCC GCC AGG CTC TAT TAT TAC GTG TCA TCA       1104
Ala His Leu Ala Phe Ala Pro Ala Arg Leu Tyr Tyr Tyr Val Ser Ser
        355                 360                 365

TTC CTG TCC CCC AAA ACT CCA GCA GTC GGT CCA ATG CGA CTT TAC AAC       1152
Phe Leu Ser Pro Lys Thr Pro Ala Val Gly Pro Met Arg Leu Tyr Asn
    370                 375                 380

AGG AGG GGG TCC ACT GGT ACT CCA GGC TCC TGT CAT CAA ATG GGA ACG       1200
Arg Arg Gly Ser Thr Gly Thr Pro Gly Ser Cys His Gln Met Gly Thr
385                 390                 395                 400

TGG CTT TTG GAC AGC AAC ATG CTT CAT CCT TTG GGG ATG TCA GTA AAC       1248
Trp Leu Leu Asp Ser Asn Met Leu His Pro Leu Gly Met Ser Val Asn
                405                 410                 415

TCA AGC TG                                                            1256
Ser Ser (2) INFORMATION FOR SEQ ID NO: 6:

(i) SEQUENCE CHARACTERISTICS:
        (A) LENGTH: 1425 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1425

(xi) SEQUENCE DESCRIPTION: SEQ ID NO: 6:

ATG CTG CTG CTG GCG AGA TGT CTG CTG CTA GTC CTC GTC TCC TCG CTG         48
Met Leu Leu Leu Ala Arg Cys Leu Leu Leu Val Leu Val Ser Ser Leu
1               5                   10                  15

CTG GTA TGC TCG GGA CTG GCG TGC GGA CCG GGC AGG GGG TTC GGG AAG         96
Leu Val Cys Ser Gly Leu Ala Cys Gly Pro Gly Arg Gly Phe Gly Lys
            20                  25                  30

AGG AGG CAC CCC AAA AAG CTG ACC CCT TTA GCC TAC AAG CAG TTT ATC        144
Arg Arg His Pro Lys Lys Leu Thr Pro Leu Ala Tyr Lys Gln Phe Ile
        35                  40                  45

CCC AAT GTG GCC GAG AAG ACC CTA GGC GCC AGC GGA AGG TAT GAA GGG        192
Pro Asn Val Ala Glu Lys Thr Leu Gly Ala Ser Gly Arg Tyr Glu Gly
```

```
                50                      55                      60
AAG ATC TCC AGA AAC TCC GAG CGA TTT AAG GAA CTC ACC CCC AAT TAC     240
Lys Ile Ser Arg Asn Ser Glu Arg Phe Lys Glu Leu Thr Pro Asn Tyr
 65                  70                  75                  80

AAC CCC GAC ATC ATA TTT AAG GAT GAA GAA AAC ACC GGA GCG GAC AGG     288
Asn Pro Asp Ile Ile Phe Lys Asp Glu Glu Asn Thr Gly Ala Asp Arg
                         85                  90                  95

CTG ATG ACT CAG AGG TGT AAG GAC AAG TTG AAC GCT TTG GCC ATC TCG     336
Leu Met Thr Gln Arg Cys Lys Asp Lys Leu Asn Ala Leu Ala Ile Ser
                100                 105                 110

GTG ATG AAC CAG TGG CCA GGA GTG AAA CTG CGG GTG ACC GAG GGC TGG     384
Val Met Asn Gln Trp Pro Gly Val Lys Leu Arg Val Thr Glu Gly Trp
            115                 120                 125

GAC GAA GAT GGC CAC CAC TCA GAG GAG TCT CTG CAC TAC GAG GGC CGC     432
Asp Glu Asp Gly His His Ser Glu Glu Ser Leu His Tyr Glu Gly Arg
    130                 135                 140

GCA GTG GAC ATC ACC ACG TCT GAC CGC GAC CGC AGC AAG TAC GGC ATG     480
Ala Val Asp Ile Thr Thr Ser Asp Arg Asp Arg Ser Lys Tyr Gly Met
145                 150                 155                 160

CTG GCC CGC CTG GCG GTG GAG GCC GGC TTC GAC TGG GTG TAC TAC GAG     528
Leu Ala Arg Leu Ala Val Glu Ala Gly Phe Asp Trp Val Tyr Tyr Glu
                165                 170                 175

TCC AAG GCA CAT ATC CAC TGC TCG GTG AAA GCA GAG AAC TCG GTG GCG     576
Ser Lys Ala His Ile His Cys Ser Val Lys Ala Glu Asn Ser Val Ala
                    180                 185                 190

GCC AAA TCG GGA GGC TGC TTC CCG GGC TCG GCC ACG GTG CAC CTG GAG     624
Ala Lys Ser Gly Gly Cys Phe Pro Gly Ser Ala Thr Val His Leu Glu
                195                 200                 205

CAG GGC GGC ACC AAG CTG GTG AAG GAC CTG AGC CCC GGG GAC CGC GTG     672
Gln Gly Gly Thr Lys Leu Val Lys Asp Leu Ser Pro Gly Asp Arg Val
        210                 215                 220

CTG GCG GCG GAC GAC CAG GGC CGG CTG CTC TAC AGC GAC TTC CTC ACT     720
Leu Ala Ala Asp Asp Gln Gly Arg Leu Leu Tyr Ser Asp Phe Leu Thr
225                 230                 235                 240

TTC CTG GAC CGC GAC GAC GGC GCC AAG AAG GTC TTC TAC GTG ATC GAG     768
Phe Leu Asp Arg Asp Asp Gly Ala Lys Lys Val Phe Tyr Val Ile Glu
                245                 250                 255

ACG CGG GAG CCG CGC GAG CGC CTG CTC CTC ACC GCC GCG CAC CTG CTC     816
Thr Arg Glu Pro Arg Glu Arg Leu Leu Leu Thr Ala Ala His Leu Leu
                260                 265                 270

TTT GTG GCG CCG CAC AAC GAC TCG GCC ACC GGG GAG CCC GAG GCG TCC     864
Phe Val Ala Pro His Asn Asp Ser Ala Thr Gly Glu Pro Glu Ala Ser
            275                 280                 285

TCG GGC TCG GGG CCG CCT TCC GGG GGC GCA CTG GGG CCT CGG GCG CTG     912
Ser Gly Ser Gly Pro Pro Ser Gly Gly Ala Leu Gly Pro Arg Ala Leu
        290                 295                 300

TTC GCC AGC CGC GTG CGC CCG GGC CAG CGC GTG TAC GTG GTG GCC GAG     960
Phe Ala Ser Arg Val Arg Pro Gly Gln Arg Val Tyr Val Val Ala Glu
305                 310                 315                 320

CGT GAC GGG GAC CGC CGG CTC CTG CCC GCC GCT GTG CAC AGC GTG ACC    1008
Arg Asp Gly Asp Arg Arg Leu Leu Pro Ala Ala Val His Ser Val Thr
                325                 330                 335

CTA AGC GAG GAG GCC GCG GGC GCC TAC GCG CCG CTC ACG GCC CAG GGC    1056
Leu Ser Glu Glu Ala Ala Gly Ala Tyr Ala Pro Leu Thr Ala Gln Gly
                340                 345                 350

ACC ATT CTC ATC AAC CGG GTG CTG GCC TCG TGC TAC GCG GTC ATC GAG    1104
Thr Ile Leu Ile Asn Arg Val Leu Ala Ser Cys Tyr Ala Val Ile Glu
            355                 360                 365

GAG CAC AGC TGG GCG CAC CGG GCC TTC GCG CCC TTC CGC CTG GCG CAC    1152
```

-continued

```
                Glu His Ser Trp Ala His Arg Ala Phe Ala Pro Phe Arg Leu Ala His
                    370                 375                 380

GCG CTC CTG GCT GCA CTG GCG CCC GCG CGC ACG GAC CGC GGC GGG GAC          1200
Ala Leu Leu Ala Ala Leu Ala Pro Ala Arg Thr Asp Arg Gly Gly Asp
385                 390                 395                 400

AGC GGC GGC GGG GAC CGC GGG GGC GGC GGC AGA GTA GCC CTA ACC              1248
Ser Gly Gly Gly Asp Arg Gly Gly Gly Gly Arg Val Ala Leu Thr
                405                 410                 415

GCT CCA GGT GCT GCC GAC GCT CCG GGT GCG GGG GCC ACC GCG GGC ATC          1296
Ala Pro Gly Ala Ala Asp Ala Pro Gly Ala Gly Ala Thr Ala Gly Ile
                420                 425                 430

CAC TGG TAC TCG CAG CTG CTC TAC CAA ATA GGC ACC TGG CTC CTG GAC          1344
His Trp Tyr Ser Gln Leu Leu Tyr Gln Ile Gly Thr Trp Leu Leu Asp
                435                 440                 445

AGC GAG GCC CTG CAC CCG CTG GGC ATG GCG GTC AAG TCC AGC NNN AGC          1392
Ser Glu Ala Leu His Pro Leu Gly Met Ala Val Lys Ser Ser Xaa Ser
                450                 455                 460

CGG GGG GCC GGG GGA GGG GCG CGG GAG GGG GCC                              1425
Arg Gly Ala Gly Gly Gly Ala Arg Glu Gly Ala
465                 470                 475

(2) INFORMATION FOR SEQ ID NO: 7:

(i) SEQUENCE CHARACTERISTICS:
        (A) LENGTH: 1622 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 51..1283

(xi) SEQUENCE DESCRIPTION: SEQ ID NO: 7:

CATCAGCCCA CCAGGAGACC TCGCCCGCCG CTCCCCCGGG CTCCCCGGCC ATG TCT           56
                                                        Met Ser
                                                          1

CCC GCC CGG CTC CGG CCC CGA CTG CAC TTC TGC CTG GTC CTG TTG CTG         104
Pro Ala Arg Leu Arg Pro Arg Leu His Phe Cys Leu Val Leu Leu Leu
        5                   10                  15

CTG CTG GTG GTG CCC GCG GCA TGG GGC TGC GGG CCG GGT CGG GTG GTG         152
Leu Leu Val Val Pro Ala Ala Trp Gly Cys Gly Pro Gly Arg Val Val
    20                  25                  30

GGC AGC CGC CGG CGA CCG CCA CGC AAA CTC GTG CCG CTC GCC TAC AAG         200
Gly Ser Arg Arg Arg Pro Pro Arg Lys Leu Val Pro Leu Ala Tyr Lys
35                  40                  45                  50

CAG TTC AGC CCC AAT GTG CCC GAG AAG ACC CTG GGC GCC AGC GGA CGC         248
Gln Phe Ser Pro Asn Val Pro Glu Lys Thr Leu Gly Ala Ser Gly Arg
                55                  60                  65

TAT GAA GGC AAG ATC GCT CGC AGC TCC GAG CGC TTC AAG GAG CTC ACC         296
Tyr Glu Gly Lys Ile Ala Arg Ser Ser Glu Arg Phe Lys Glu Leu Thr
            70                  75                  80

CCC AAT TAC AAT CCA GAC ATC ATC TTC AAG GAC GAG GAG AAC ACA GGC         344
Pro Asn Tyr Asn Pro Asp Ile Ile Phe Lys Asp Glu Glu Asn Thr Gly
        85                  90                  95

GCC GAC CGC CTC ATG ACC CAG CGC TGC AAG GAC CGC CTG AAC TCG CTG         392
Ala Asp Arg Leu Met Thr Gln Arg Cys Lys Asp Arg Leu Asn Ser Leu
    100                 105                 110

GCT ATC TCG GTG ATG AAC CAG TGG CCC GGT GTG AAG CTG CGG GTG ACC         440
Ala Ile Ser Val Met Asn Gln Trp Pro Gly Val Lys Leu Arg Val Thr
```

```
                  115                 120                 125                 130
GAG GGC TGG GAC GAG GAC GGC CAC CAC TCA GAG GAG TCC CTG CAT TAT                488
Glu Gly Trp Asp Glu Asp Gly His His Ser Glu Glu Ser Leu His Tyr
                        135                 140                 145

GAG GGC CGC GCG GTG GAC ATC ACC ACA TCA GAC CGC GAC CGC AAT AAG                536
Glu Gly Arg Ala Val Asp Ile Thr Thr Ser Asp Arg Asp Arg Asn Lys
                150                 155                 160

TAT GGA CTG CTG GCG CGC TTG GCA GTG GAG GCC GGC TTT GAC TGG GTG                584
Tyr Gly Leu Leu Ala Arg Leu Ala Val Glu Ala Gly Phe Asp Trp Val
            165                 170                 175

TAT TAC GAG TCA AAG GCC CAC GTG CAT TGC TCC GTC AAG TCC GAG CAC                632
Tyr Tyr Glu Ser Lys Ala His Val His Cys Ser Val Lys Ser Glu His
        180                 185                 190

TCG GCC GCA GCC AAG ACG GGC GGC TGC TTC CCT GCC GGA GCC CAG GTA                680
Ser Ala Ala Ala Lys Thr Gly Gly Cys Phe Pro Ala Gly Ala Gln Val
195                 200                 205                 210

CGC CTG GAG AGT GGG GCG CGT GTG GCC TTG TCA GCC GTG AGG CCG GGA                728
Arg Leu Glu Ser Gly Ala Arg Val Ala Leu Ser Ala Val Arg Pro Gly
                215                 220                 225

GAC CGT GTG CTG GCC ATG GGG GAG GAT GGG AGC CCC ACC TTC AGC GAT                776
Asp Arg Val Leu Ala Met Gly Glu Asp Gly Ser Pro Thr Phe Ser Asp
            230                 235                 240

GTG CTC ATT TTC CTG GAC CGC GAG CCC CAC AGG CTG AGA GCC TTC CAG                824
Val Leu Ile Phe Leu Asp Arg Glu Pro His Arg Leu Arg Ala Phe Gln
        245                 250                 255

GTC ATC GAG ACT CAG GAC CCC CCA CGC CGC CTG GCA CTC ACA CCC GCT                872
Val Ile Glu Thr Gln Asp Pro Pro Arg Arg Leu Ala Leu Thr Pro Ala
260                 265                 270

CAC CTG CTC TTT ACG GCT GAC AAT CAC ACG GAG CCG GCA GCC CGC TTC                920
His Leu Leu Phe Thr Ala Asp Asn His Thr Glu Pro Ala Ala Arg Phe
275                 280                 285                 290

CGG GCC ACA TTT GCC AGC CAC GTG CAG CCT GGC CAG TAC GTG CTG GTG                968
Arg Ala Thr Phe Ala Ser His Val Gln Pro Gly Gln Tyr Val Leu Val
                295                 300                 305

GCT GGG GTG CCA GGC CTG CAG CCT GCC CGC GTG GCA GCT GTC TCT ACA               1016
Ala Gly Val Pro Gly Leu Gln Pro Ala Arg Val Ala Ala Val Ser Thr
            310                 315                 320

CAC GTG GCC CTC GGG GCC TAC GCC CCG CTC ACA AAG CAT GGG ACA CTG               1064
His Val Ala Leu Gly Ala Tyr Ala Pro Leu Thr Lys His Gly Thr Leu
        325                 330                 335

GTG GTG GAG GAT GTG GTG GCA TCC TGC TTC GCG GCC GTG GCT GAC CAC               1112
Val Val Glu Asp Val Val Ala Ser Cys Phe Ala Ala Val Ala Asp His
340                 345                 350

CAC CTG GCT CAG TTG GCC TTC TGG CCC CTG AGA CTC TTT CAC AGC TTG               1160
His Leu Ala Gln Leu Ala Phe Trp Pro Leu Arg Leu Phe His Ser Leu
355                 360                 365                 370

GCA TGG GGC AGC TGG ACC CCG GGG GAG GGT GTG CAT TGG TAC CCC CAG               1208
Ala Trp Gly Ser Trp Thr Pro Gly Glu Gly Val His Trp Tyr Pro Gln
                375                 380                 385

CTG CTC TAC CGC CTG GGG CGT CTC CTG CTA GAA GAG GGC AGC TTC CAC               1256
Leu Leu Tyr Arg Leu Gly Arg Leu Leu Leu Glu Glu Gly Ser Phe His
            390                 395                 400

CCA CTG GGC ATG TCC GGG GCA GGG AGC TGAAAGGACT CCACCGCTGC                     1303
Pro Leu Gly Met Ser Gly Ala Gly Ser
            405                 410

CCTCCTGGAA CTGCTGTACT GGGTCCAGAA GCCTCTCAGC CAGGAGGGAG CTGGCCCT              1363

AAGGGACCTG AGCTGGGGGA CACTGGCTCC TGCCATCTCC TCTGCCATGA AGATACAC              1423

TTGAGACTTG ACTGGGCAAC ACCAGCGTCC CCCACCCGCG TCGTGGTGTA GTCATAGA              1483
```

-continued

```
TGCAAGCTGA GCTGGCGAGG GGATGGTTGT TGACCCCTCT CTCCTAGAGA CCTTGAGG         1543

GGCACGGCGA CTCCCAACTC AGCCTGCTCT CACTACGAGT TTTCATACTC TGCCTCCC         1603

ATTGGGAGGG CCCATTCCC                                                    1622

(2) INFORMATION FOR SEQ ID NO: 8:

(i) SEQUENCE CHARACTERISTICS:
        (A) LENGTH: 1191 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1191

(xi) SEQUENCE DESCRIPTION: SEQ ID NO: 8:

ATG GCT CTC CTG ACC AAT CTA CTG CCC TTG TGC TGC TTG GCA CTT CTG          48
Met Ala Leu Leu Thr Asn Leu Leu Pro Leu Cys Cys Leu Ala Leu Leu
 1               5                  10                  15

GCG CTG CCA GCC CAG AGC TGC GGG CCG GGC CGG GGG CCG GTT GGC CGG          96
Ala Leu Pro Ala Gln Ser Cys Gly Pro Gly Arg Gly Pro Val Gly Arg
                20                  25                  30

CGC CGC TAT GCG CGC AAG CAG CTC GTG CCG CTA CTC TAC AAG CAA TTT         144
Arg Arg Tyr Ala Arg Lys Gln Leu Val Pro Leu Leu Tyr Lys Gln Phe
        35                  40                  45

GTG CCC GGC GTG CCA GAG CGG ACC CTG GGC GCC AGT GGG CCA GCG GAG         192
Val Pro Gly Val Pro Glu Arg Thr Leu Gly Ala Ser Gly Pro Ala Glu
 50                  55                  60

GGG AGG GTG GCA AGG GGC TCC GAG CGC TTC CGG GAC CTC GTG CCC AAC         240
Gly Arg Val Ala Arg Gly Ser Glu Arg Phe Arg Asp Leu Val Pro Asn
 65                  70                  75                  80

TAC AAC CCC GAC ATC ATC TTC AAG GAT GAG GAG AAC AGT GGA GCC GAC         288
Tyr Asn Pro Asp Ile Ile Phe Lys Asp Glu Glu Asn Ser Gly Ala Asp
                85                  90                  95

CGC CTG ATG ACC GAG CGT TGC AAG GAG AGG GTG AAC GCT TTG GCC ATT         336
Arg Leu Met Thr Glu Arg Cys Lys Glu Arg Val Asn Ala Leu Ala Ile
                100                 105                 110

GCC GTG ATG AAC ATG TGG CCC GGA GTG CGC CTA CGA GTG ACT GAG GGC         384
Ala Val Met Asn Met Trp Pro Gly Val Arg Leu Arg Val Thr Glu Gly
        115                 120                 125

TGG GAC GAG GAC GGC CAC CAC GCT CAG GAT TCA CTC CAC TAC GAA GGC         432
Trp Asp Glu Asp Gly His His Ala Gln Asp Ser Leu His Tyr Glu Gly
130                 135                 140

CGT GCT TTG GAC ATC ACT ACG TCT GAC CGC GAC CGC AAC AAG TAT GGG         480
Arg Ala Leu Asp Ile Thr Thr Ser Asp Arg Asp Arg Asn Lys Tyr Gly
145                 150                 155                 160

TTG CTG GCG CGC CTC GCA GTG GAA GCC GGC TTC GAC TGG GTC TAC TAC         528
Leu Leu Ala Arg Leu Ala Val Glu Ala Gly Phe Asp Trp Val Tyr Tyr
                165                 170                 175

GAG TCC CGC AAC CAC GTC CAC GTG TCG GTC AAA GCT GAT AAC TCA CTG         576
Glu Ser Arg Asn His Val His Val Ser Val Lys Ala Asp Asn Ser Leu
                180                 185                 190

GCG GTC CGG GCG GGC GGC TGC TTT CCG GGA AAT GCA ACT GTG CGC CTG         624
Ala Val Arg Ala Gly Gly Cys Phe Pro Gly Asn Ala Thr Val Arg Leu
                195                 200                 205

TGG AGC GGC GAG CGG AAA GGG CTG CGG GAA CTG CAC CGC GGA GAC TGG         672
Trp Ser Gly Glu Arg Lys Gly Leu Arg Glu Leu His Arg Gly Asp Trp
210                 215                 220
```

-continued

```
GTT TTG GCG GCC GAT GCG TCA GGC CGG GTG GTG CCC ACG CCG GTG CTG      720
Val Leu Ala Ala Asp Ala Ser Gly Arg Val Val Pro Thr Pro Val Leu
225                 230                 235                 240

CTC TTC CTG GAC CGG GAC TTG CAG CGC CGG GCT TCA TTT GTG GCT GTG      768
Leu Phe Leu Asp Arg Asp Leu Gln Arg Arg Ala Ser Phe Val Ala Val
                245                 250                 255

GAG ACC GAG TGG CCT CCA CGC AAA CTG TTG CTC ACG CCC TGG CAC CTG      816
Glu Thr Glu Trp Pro Pro Arg Lys Leu Leu Leu Thr Pro Trp His Leu
            260                 265                 270

GTG TTT GCC GCT CGA GGG CCG GCG CCC GCG CCA GGC GAC TTT GCA CCG      864
Val Phe Ala Ala Arg Gly Pro Ala Pro Ala Pro Gly Asp Phe Ala Pro
        275                 280                 285

GTG TTC GCG CGC CGG CTA CGC GCT GGG GAC TCG GTG CTG GCG CCC GGC      912
Val Phe Ala Arg Arg Leu Arg Ala Gly Asp Ser Val Leu Ala Pro Gly
    290                 295                 300

GGG GAT GCG CTT CGG CCA GCG CGC GTG GCC CGT GTG GCG CGG GAG GAA      960
Gly Asp Ala Leu Arg Pro Ala Arg Val Ala Arg Val Ala Arg Glu Glu
305                 310                 315                 320

GCC GTG GGC GTG TTC GCG CCG CTC ACC GCG CAC GGG ACG CTG CTG GTG     1008
Ala Val Gly Val Phe Ala Pro Leu Thr Ala His Gly Thr Leu Leu Val
                325                 330                 335

AAC GAT GTC CTG GCC TCT TGC TAC GCG GTT CTG GAG AGT CAC CAG TGG     1056
Asn Asp Val Leu Ala Ser Cys Tyr Ala Val Leu Glu Ser His Gln Trp
                340                 345                 350

GCG CAC CGC GCT TTT GCC CCC TTG AGA CTG CTG CAC GCG CTA GGG GCG     1104
Ala His Arg Ala Phe Ala Pro Leu Arg Leu Leu His Ala Leu Gly Ala
            355                 360                 365

CTG CTC CCC GGC GGG GCC GTC CAG CCG ACT GGC ATG CAT TGG TAC TCT     1152
Leu Leu Pro Gly Gly Ala Val Gln Pro Thr Gly Met His Trp Tyr Ser
370                 375                 380

CGG CTC CTC TAC CGC TTA GCG GAG GAG CTA CTG GGC TGA                 1191
Arg Leu Leu Tyr Arg Leu Ala Glu Glu Leu Leu Gly
385                 390                 395
```

(2) INFORMATION FOR SEQ ID NO: 9:

(i) SEQUENCE CHARACTERISTICS:
        (A) LENGTH: 1251 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1248

(xi) SEQUENCE DESCRIPTION: SEQ ID NO: 9:

```
ATG GAC GTA AGG CTG CAT CTG AAG CAA TTT GCT TTA CTG TGT TTT ATC       48
Met Asp Val Arg Leu His Leu Lys Gln Phe Ala Leu Leu Cys Phe Ile
1               5                   10                  15

AGC TTG CTT CTG ACG CCT TGT GGA TTA GCC TGT GGT CCT GGT AGA GGT       96
Ser Leu Leu Leu Thr Pro Cys Gly Leu Ala Cys Gly Pro Gly Arg Gly
                20                  25                  30

TAT GGA AAA CGA AGA CAC CCA AAG AAA TTA ACC CCG TTG GCT TAC AAG      144
Tyr Gly Lys Arg Arg His Pro Lys Lys Leu Thr Pro Leu Ala Tyr Lys
            35                  40                  45

CAA TTC ATC CCC AAC GTT GCT GAG AAA ACG CTT GGA GCC AGC GGC AAA      192
Gln Phe Ile Pro Asn Val Ala Glu Lys Thr Leu Gly Ala Ser Gly Lys
        50                  55                  60

TAC GAA GGC AAA ATC ACA AGG AAT TCA GAG AGA TTT AAA GAG CTG ATT      240
```

```
Tyr Glu Gly Lys Ile Thr Arg Asn Ser Glu Arg Phe Lys Glu Leu Ile
65                  70                  75                  80

CCG AAT TAT AAT CCC GAT ATC ATC TTT AAG GAC GAG GAA AAC ACA AAC          288
Pro Asn Tyr Asn Pro Asp Ile Ile Phe Lys Asp Glu Glu Asn Thr Asn
                85                  90                  95

GCT GAC AGG CTG ATG ACC AAG CGC TGT AAG GAC AAG TTA AAT TCG TTG          336
Ala Asp Arg Leu Met Thr Lys Arg Cys Lys Asp Lys Leu Asn Ser Leu
            100                 105                 110

GCC ATA TCC GTC ATG AAC CAC TGG CCC GGC GTG AAA CTG CGC GTC ACT          384
Ala Ile Ser Val Met Asn His Trp Pro Gly Val Lys Leu Arg Val Thr
            115                 120                 125

GAA GGC TGG GAT GAG GAT GGT CAC CAT TTA GAA GAA TCT TTG CAC TAT          432
Glu Gly Trp Asp Glu Asp Gly His His Leu Glu Glu Ser Leu His Tyr
            130                 135                 140

GAG GGA CGG GCA GTG GAC ATC ACT ACC TCA GAC AGG GAT AAA AGC AAG          480
Glu Gly Arg Ala Val Asp Ile Thr Thr Ser Asp Arg Asp Lys Ser Lys
145                 150                 155                 160

TAT GGG ATG CTA TCC AGG CTT GCA GTG GAG GCA GGA TTC GAC TGG GTC          528
Tyr Gly Met Leu Ser Arg Leu Ala Val Glu Ala Gly Phe Asp Trp Val
                165                 170                 175

TAT TAT GAA TCT AAA GCC CAC ATA CAC TGC TCT GTC AAA GCA GAA AAT          576
Tyr Tyr Glu Ser Lys Ala His Ile His Cys Ser Val Lys Ala Glu Asn
                180                 185                 190

TCA GTG GCT GCT AAA TCA GGA GGA TGT TTT CCT GGG TCT GGG ACG GTG          624
Ser Val Ala Ala Lys Ser Gly Gly Cys Phe Pro Gly Ser Gly Thr Val
            195                 200                 205

ACA CTT GGT GAT GGG ACG AGG AAA CCC ATC AAA GAT CTT AAA GTG GGC          672
Thr Leu Gly Asp Gly Thr Arg Lys Pro Ile Lys Asp Leu Lys Val Gly
210                 215                 220

GAC CGG GTT TTG GCT GCA GAC GAG AAG GGA AAT GTC TTA ATA AGC GAC          720
Asp Arg Val Leu Ala Ala Asp Glu Lys Gly Asn Val Leu Ile Ser Asp
225                 230                 235                 240

TTT ATT ATG TTT ATA GAC CAC GAT CCG ACA ACG AGA AGG CAA TTC ATC          768
Phe Ile Met Phe Ile Asp His Asp Pro Thr Thr Arg Arg Gln Phe Ile
                245                 250                 255

GTC ATC GAG ACG TCA GAA CCT TTC ACC AAG CTC ACC CTC ACT GCC GCG          816
Val Ile Glu Thr Ser Glu Pro Phe Thr Lys Leu Thr Leu Thr Ala Ala
                260                 265                 270

CAC CTA GTT TTC GTT GGA AAC TCT TCA GCA GCT TCG GGT ATA ACA GCA          864
His Leu Val Phe Val Gly Asn Ser Ser Ala Ala Ser Gly Ile Thr Ala
            275                 280                 285

ACA TTT GCC AGC AAC GTG AAG CCT GGA GAT ACA GTT TTA GTG TGG GAA          912
Thr Phe Ala Ser Asn Val Lys Pro Gly Asp Thr Val Leu Val Trp Glu
            290                 295                 300

GAC ACA TGC GAG AGC CTC AAG AGC GTT ACA GTG AAA AGG ATT TAC ACT          960
Asp Thr Cys Glu Ser Leu Lys Ser Val Thr Val Lys Arg Ile Tyr Thr
305                 310                 315                 320

GAG GAG CAC GAG GGC TCT TTT GCG CCA GTC ACC GCG CAC GGA ACC ATA         1008
Glu Glu His Glu Gly Ser Phe Ala Pro Val Thr Ala His Gly Thr Ile
                325                 330                 335

ATA GTG GAT CAG GTG TTG GCA TCG TGC TAC GCG GTC ATT GAG AAC CAC         1056
Ile Val Asp Gln Val Leu Ala Ser Cys Tyr Ala Val Ile Glu Asn His
            340                 345                 350

AAA TGG GCA CAT TGG GCT TTT GCG CCG GTC AGG TTG TGT CAC AAG CTG         1104
Lys Trp Ala His Trp Ala Phe Ala Pro Val Arg Leu Cys His Lys Leu
            355                 360                 365

ATG ACG TGG CTT TTT CCG GCT CGT GAA TCA AAC GTC AAT TTT CAG GAG         1152
Met Thr Trp Leu Phe Pro Ala Arg Glu Ser Asn Val Asn Phe Gln Glu
370                 375                 380
```

-continued

```
GAT GGT ATC CAC TGG TAC TCA AAT ATG CTG TTT CAC ATC GGC TCT TGG      1200
Asp Gly Ile His Trp Tyr Ser Asn Met Leu Phe His Ile Gly Ser Trp
385                 390                 395                 400

CTG CTG GAC AGA GAC TCT TTC CAT CCA CTC GGG ATT TTA CAC TTA AGT      1248
Leu Leu Asp Arg Asp Ser Phe His Pro Leu Gly Ile Leu His Leu Ser
                405                 410                 415

TGA                                                                   1251
```

(2) INFORMATION FOR SEQ ID NO: 10:

(i) SEQUENCE CHARACTERISTICS:
        (A) LENGTH: 425 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Val Glu Met Leu Leu Leu Thr Arg Ile Leu Leu Val Gly Phe Ile
1               5                   10                  15

Cys Ala Leu Leu Val Ser Ser Gly Leu Thr Cys Gly Pro Gly Arg Gly
                20                  25                  30

Ile Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
                100                 105                 110

Ala Ile Ser Val Met Asn Gln Trp Pro Gly Val Lys Leu Arg Val Thr
            115                 120                 125

Glu Gly Trp Asp Glu Asp Gly His His Ser Glu Glu Ser Leu His Tyr
    130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
    195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
            260                 265                 270

His Leu Leu Phe Val Ala Pro Gln His Asn Gln Ser Glu Ala Thr Gly
    275                 280                 285

Ser Thr Ser Gly Gln Ala Leu Phe Ala Ser Asn Val Lys Pro Gly Gln
    290                 295                 300
```

```
Arg Val Tyr Val Leu Gly Glu Gly Gly Gln Gln Leu Pro Ala Ser
305                 310                 315                 320

Val His Ser Val Ser Leu Arg Glu Glu Ala Ser Gly Ala Tyr Ala Pro
            325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
            355                 360                 365

Phe Arg Leu Ala Gln Gly Leu Leu Ala Ala Leu Cys Pro Asp Gly Ala
            370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
            420                 425

(2) INFORMATION FOR SEQ ID NO: 11:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO: 11:

Met Ala Leu Pro Ala Ser Leu Leu Pro Leu Cys Cys Leu Ala Leu Leu
1               5                   10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
            35                  40                  45

Val Pro Ser Met Pro Glu Arg Thr Leu Gly Ala Ser Gly Pro Ala Glu
        50                  55                  60

Gly Arg Val Thr Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
                100                 105                 110

Ala Val Met Asn Met Trp Pro Gly Val Arg Leu Arg Val Thr Glu Gly
            115                 120                 125

Trp Asp Glu Asp Gly His His Ala Gln Asp Ser Leu His Tyr Glu Gly
130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
                180                 185                 190

Ala Val Arg Ala Gly Gly Cys Phe Pro Gly Asn Ala Thr Val Arg Leu
            195                 200                 205

Arg Ser Gly Glu Arg Lys Gly Leu Arg Glu Leu His Arg Gly Asp Trp
210                 215                 220

Val Leu Ala Ala Asp Ala Ala Gly Arg Val Val Pro Thr Pro Val Leu
```

```
              225                 230                 235                 240
Leu Phe Leu Asp Arg Asp Leu Gln Arg Arg Ala Ser Phe Val Ala Val
                    245                 250                 255
Glu Thr Glu Arg Pro Pro Arg Lys Leu Leu Thr Pro Trp His Leu
                260                 265                 270
Val Phe Ala Ala Arg Gly Pro Ala Pro Ala Pro Gly Asp Phe Ala Pro
                    275                 280                 285
Val Phe Ala Arg Arg Leu Arg Ala Gly Asp Ser Val Leu Ala Pro Gly
                290                 295                 300
Gly Asp Ala Leu Gln Pro Ala Arg Val Ala Arg Val Ala Arg Glu Glu
305                 310                 315                 320
Ala Val Gly Val Phe Ala Pro Leu Thr Ala His Gly Thr Leu Leu Val
                    325                 330                 335
Asn Asp Val Leu Ala Ser Cys Tyr Ala Val Leu Glu Ser His Gln Trp
                340                 345                 350
Ala His Arg Ala Phe Ala Pro Leu Arg Leu Leu His Ala Leu Gly Ala
                    355                 360                 365
Leu Leu Pro Gly Gly Ala Val Gln Pro Thr Gly Met His Trp Tyr Ser
370                 375                 380
Arg Leu Leu Tyr Arg Leu Ala Glu Glu Leu Met Gly
385                 390                 395
```

(2) INFORMATION FOR SEQ ID NO: 12:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Ser Pro Ala Trp Leu Arg Pro Arg Leu Arg Phe Cys Leu Phe Leu
1               5                   10                  15
Leu Leu Leu Leu Leu Val Pro Ala Ala Arg Gly Cys Gly Pro Gly Arg
                20                  25                  30
Val Val Gly Ser Arg Arg Arg Pro Pro Arg Lys Leu Val Pro Leu Ala
                35                  40                  45
Tyr Lys Gln Phe Ser Pro Asn Val Pro Glu Lys Thr Leu Gly Ala Ser
            50                  55                  60
Gly Arg Tyr Glu Gly Lys Ile Ala Arg Ser Ser Glu Arg Phe Lys Glu
65                  70                  75                  80
Leu Thr Pro Asn Tyr Asn Pro Asp Ile Ile Phe Lys Asp Glu Glu Asn
                    85                  90                  95
Thr Gly Ala Asp Arg Leu Met Thr Gln Arg Cys Lys Asp Arg Leu Asn
                100                 105                 110
Ser Leu Ala Ile Ser Val Met Asn Gln Trp Pro Gly Val Lys Leu Arg
                115                 120                 125
Val Thr Glu Gly Arg Asp Glu Asp Gly His His Ser Glu Glu Ser Leu
                130                 135                 140
His Tyr Glu Gly Arg Ala Val Asp Ile Thr Thr Ser Asp Arg Asp Arg
145                 150                 155                 160
Asn Lys Tyr Gly Leu Leu Ala Arg Leu Ala Val Glu Ala Gly Phe Asp
                    165                 170                 175
Trp Val Tyr Tyr Glu Ser Lys Ala His Val His Cys Ser Val Lys Ser
                    180                 185                 190
```

```
Glu His Ser Ala Ala Ala Lys Thr Gly Gly Cys Phe Pro Ala Gly Ala
            195                 200                 205

Gln Val Arg Leu Glu Asn Gly Glu Arg Val Ala Leu Ser Ala Val Lys
            210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
            245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
            275                 280                 285

His Phe Arg Ala Thr Phe Ala Ser His Val Gln Pro Gly Gln Tyr Val
            290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
            325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
            355                 360                 365

Ser Leu Ala Trp Gly Ser Trp Thr Pro Ser Glu Gly Val His Ser Tyr
370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
                405                 410

(2) INFORMATION FOR SEQ ID NO: 13:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO: 13:

Met Leu Leu Leu Ala Arg Cys Phe Leu Val Ile Leu Ala Ser Ser
 1                5                  10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
            35                  40                  45

Ile Pro Asn Val Ala Glu Lys Thr Leu Gly Ala Ser Gly Arg Tyr Glu
            50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Arg Leu Arg Val Thr Glu Gly
            115                 120                 125
```

```
Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
                260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
        290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
                355                 360                 365

Ala His Ala Leu Leu Ala Ala Leu Ala Pro Ala Arg Thr Asp Gly Gly
        370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
                420                 425                 430

Ala Val Lys Ser Ser
            435

(2) INFORMATION FOR SEQ ID NO: 14:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO: 14:

Met Arg Leu Leu Thr Arg Val Leu Leu Val Ser Leu Leu Thr Leu Ser
 1               5                   10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
```

```
                35                  40                  45
Pro Asn Val Ala Glu Lys Thr Leu Gly Ala Ser Gly Arg Tyr Glu Gly
         50                  55                  60

Lys Ile Thr Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ser Leu Ala Ile Ser
                100                 105                 110

Val Met Asn His Trp Pro Gly Val Lys Leu Arg Val Thr Glu Gly Trp
            115                 120                 125

Asp Glu Asp Gly His His Phe Glu Glu Ser Leu His Tyr Glu Gly Arg
        130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
        210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
        290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Tyr Val Ser Ser
        355                 360                 365

Phe Leu Ser Pro Lys Thr Pro Ala Val Gly Pro Met Arg Leu Tyr Asn
370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser
```

(2) INFORMATION FOR SEQ ID NO: 15:

(i) SEQUENCE CHARACTERISTICS:
        (A) LENGTH: 475 amino acids
        (B) TYPE: amino acid (D) TOPOLOGY: linear (ii) MOLECULE TYPE: protein (xi) SEQUENCE DESCRIPTION: SEQ ID NO: 15:

```
Met Leu Leu Leu Ala Arg Cys Leu Leu Leu Val Leu Val Ser Ser Leu
 1               5                  10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
```

```
385                 390                 395                 400
Ser Gly Gly Gly Asp Arg Gly Gly Gly Arg Val Ala Leu Thr
                405                 410                 415

Ala Pro Gly Ala Ala Asp Ala Pro Gly Ala Gly Ala Thr Ala Gly Ile
                420                 425                 430

His Trp Tyr Ser Gln Leu Leu Tyr Gln Ile Gly Thr Trp Leu Leu Asp
                435                 440                 445

Ser Glu Ala Leu His Pro Leu Gly Met Ala Val Lys Ser Ser Xaa Ser
                450                 455                 460

Arg Gly Ala Gly Gly Ala Arg Glu Gly Ala
465                 470                 475

(2) INFORMATION FOR SEQ ID NO: 16:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO: 16:

Met Ser Pro Ala Arg Leu Arg Pro Arg Leu His Phe Cys Leu Val Leu
 1               5                  10                  15

Leu Leu Leu Val Val Pro Ala Ala Trp Gly Cys Gly Pro Gly Arg
                20                  25                  30

Val Val Gly Ser Arg Arg Arg Pro Pro Arg Lys Leu Val Pro Leu Ala
                35                  40                  45

Tyr Lys Gln Phe Ser Pro Asn Val Pro Glu Lys Thr Leu Gly Ala Ser
            50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                    85                  90                  95

Thr Gly Ala Asp Arg Leu Met Thr Gln Arg Cys Lys Asp Arg Leu Asn
                100                 105                 110

Ser Leu Ala Ile Ser Val Met Asn Gln Trp Pro Gly Val Lys Leu Arg
                115                 120                 125

Val Thr Glu Gly Trp Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
                180                 185                 190

Glu His Ser Ala Ala Ala Lys Thr Gly Gly Cys Phe Pro Ala Gly Ala
                195                 200                 205

Gln Val Arg Leu Glu Ser Gly Ala Arg Val Ala Leu Ser Ala Val Arg
                210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
                260                 265                 270
```

-continued

```
Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
        290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
                340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
        370                 375                 380

Pro Gln Leu Leu Tyr Arg Leu Gly Arg Leu Leu Leu Glu Glu Gly Ser
385                 390                 395                 400

Phe His Pro Leu Gly Met Ser Gly Ala Gly Ser
                405                 410
```

(2) INFORMATION FOR SEQ ID NO: 17:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Ala Leu Leu Thr Asn Leu Leu Pro Leu Cys Cys Leu Ala Leu Leu
1               5                   10                  15

Ala Leu Pro Ala Gln Ser Cys Gly Pro Gly Arg Gly Pro Val Gly Arg
            20                  25                  30

Arg Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
    50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
                100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
        130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
                180                 185                 190

Ala Val Arg Ala Gly Gly Cys Phe Pro Gly Asn Ala Thr Val Arg Leu
        195                 200                 205
```

```
Trp Ser Gly Glu Arg Lys Gly Leu Arg Glu Leu His Arg Gly Asp Trp
210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Trp Pro Pro Arg Lys Leu Leu Leu Thr Pro Trp His Leu
                260                 265                 270

Val Phe Ala Ala Arg Gly Pro Ala Pro Ala Pro Gly Asp Phe Ala Pro
                275                 280                 285

Val Phe Ala Arg Arg Leu Arg Ala Gly Asp Ser Val Leu Ala Pro Gly
                290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu Leu His Ala Leu Gly Ala
                355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Leu Gly
385                 390                 395

(2) INFORMATION FOR SEQ ID NO: 18:

(i) SEQUENCE CHARACTERISTICS:
        (A) LENGTH: 416 amino acids
        (B) TYPE: amino acid
        (D) TOPOLOGY: linear (ii) MOLECULE TYPE: protein (xi) SEQUENCE DESCRIPTION: SEQ ID NO: 18:

Met Asp Val Arg Leu His Leu Lys Gln Phe Ala Leu Leu Cys Phe Ile
1                   5                   10                  15

Ser Leu Leu Leu Thr Pro Cys Gly Leu Ala Cys Gly Pro Gly Arg Gly
                20                  25                  30

Tyr Gly Lys Arg Arg His Pro Lys Lys Leu Thr Pro Leu Ala Tyr Lys
                35                  40                  45

Gln Phe Ile Pro Asn Val Ala Glu Lys Thr Leu Gly Ala Ser Gly Lys
    50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr Asn
                85                  90                  95

Ala Asp Arg Leu Met Thr Lys Arg Cys Lys Asp Lys Leu Asn Ser Leu
                100                 105                 110

Ala Ile Ser Val Met Asn His Trp Pro Gly Val Lys Leu Arg Val Thr
                115                 120                 125

Glu Gly Trp Asp Glu Asp Gly His His Leu Glu Glu Ser Leu His Tyr
                130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
```

```
                165                 170                 175
    Tyr Tyr Glu Ser Lys Ala His Ile His Cys Ser Val Lys Ala Glu Asn
                180                 185                 190

Ser Val Ala Ala Lys Ser Gly Gly Cys Phe Pro Gly Ser Gly Thr Val
                195                 200                 205

Thr Leu Gly Asp Gly Thr Arg Lys Pro Ile Lys Asp Leu Lys Val Gly
                210                 215                 220

Asp Arg Val Leu Ala Ala Asp Glu Lys Gly Asn Val Leu Ile Ser Asp
    225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
                260                 265                 270

His Leu Val Phe Val Gly Asn Ser Ser Ala Ala Ser Gly Ile Thr Ala
                275                 280                 285

Thr Phe Ala Ser Asn Val Lys Pro Gly Asp Thr Val Leu Val Trp Glu
                290                 295                 300

Asp Thr Cys Glu Ser Leu Lys Ser Val Thr Val Lys Arg Ile Tyr Thr
    305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
                340                 345                 350

Lys Trp Ala His Trp Ala Phe Ala Pro Val Arg Leu Cys His Lys Leu
                355                 360                 365

Met Thr Trp Leu Phe Pro Ala Arg Glu Ser Asn Val Asn Phe Gln Glu
                370                 375                 380

Asp Gly Ile His Trp Tyr Ser Asn Met Leu Phe His Ile Gly Ser Trp
    385                 390                 395                 400

Leu Leu Asp Arg Asp Ser Phe His Pro Leu Gly Ile Leu His Leu Ser
                405                 410                 415

(2) INFORMATION FOR SEQ ID NO: 19:

(i) SEQUENCE CHARACTERISTICS:
        (A) LENGTH: 1416 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1413

(xi) SEQUENCE DESCRIPTION: SEQ ID NO: 19:

ATG GAT AAC CAC AGC TCA GTG CCT TGG GCC AGT GCC GCC AGT GTC ACC        48
Met Asp Asn His Ser Ser Val Pro Trp Ala Ser Ala Ala Ser Val Thr
 1               5                  10                  15

TGT CTC TCC CTG GGA TGC CAA ATG CCA CAG TTC CAG TTC CAG TTC CAG        96
Cys Leu Ser Leu Gly Cys Gln Met Pro Gln Phe Gln Phe Gln Phe Gln
                20                  25                  30

CTC CAA ATC CGC AGC GAG CTC CAT CTC CGC AAG CCC GCA AGA AGA ACG       144
Leu Gln Ile Arg Ser Glu Leu His Leu Arg Lys Pro Ala Arg Arg Thr
            35                  40                  45

CAA ACG ATG CGC CAC ATT GCG CAT ACG CAG CGT TGC CTC AGC AGG CTG       192
Gln Thr Met Arg His Ile Ala His Thr Gln Arg Cys Leu Ser Arg Leu
        50                  55                  60
```

-continued

```
ACC TCT CTG GTG GCC CTG CTG CTG ATC GTC TTG CCG ATG GTC TTT AGC    240
Thr Ser Leu Val Ala Leu Leu Leu Ile Val Leu Pro Met Val Phe Ser
 65              70                  75                  80

CCG GCT CAC AGC TGC GGT CCT GGC CGA GGA TTG GGT CGT CAT AGG GCG    288
Pro Ala His Ser Cys Gly Pro Gly Arg Gly Leu Gly Arg His Arg Ala
                 85                  90                  95

CGC AAC CTG TAT CCG CTG GTC CTC AAG CAG ACA ATT CCC AAT CTA TCC    336
Arg Asn Leu Tyr Pro Leu Val Leu Lys Gln Thr Ile Pro Asn Leu Ser
            100                 105                 110

GAG TAC ACG AAC AGC GCC TCC GGA CCT CTG GAG GGT GTG ATC CGT CGG    384
Glu Tyr Thr Asn Ser Ala Ser Gly Pro Leu Glu Gly Val Ile Arg Arg
        115                 120                 125

GAT TCG CCC AAA TTC AAG GAC CTC GTG CCC AAC TAC AAC AGG GAC ATC    432
Asp Ser Pro Lys Phe Lys Asp Leu Val Pro Asn Tyr Asn Arg Asp Ile
130                 135                 140

CTT TTC CGT GAC GAG GAA GGC ACC GGA GCG GAT GGC TTG ATG AGC AAG    480
Leu Phe Arg Asp Glu Glu Gly Thr Gly Ala Asp Gly Leu Met Ser Lys
145                 150                 155                 160

CGC TGC AAG GAG AAG CTA AAC GTG CTG GCC TAC TCG GTG ATG AAC GAA    528
Arg Cys Lys Glu Lys Leu Asn Val Leu Ala Tyr Ser Val Met Asn Glu
                165                 170                 175

TGG CCC GGC ATC CGG CTG CTG GTC ACC GAG AGC TGG GAC GAG GAC TAC    576
Trp Pro Gly Ile Arg Leu Leu Val Thr Glu Ser Trp Asp Glu Asp Tyr
            180                 185                 190

CAT CAC GGC CAG GAG TCG CTC CAC TAC GAG GGC CGA GCG GTG ACC ATT    624
His His Gly Gln Glu Ser Leu His Tyr Glu Gly Arg Ala Val Thr Ile
        195                 200                 205

GCC ACC TCC GAT CGC GAC CAG TCC AAA TAC GGC ATG CTC GCT CGC CTG    672
Ala Thr Ser Asp Arg Asp Gln Ser Lys Tyr Gly Met Leu Ala Arg Leu
210                 215                 220

GCC GTC GAG GCT GGA TTC GAT TGG GTC TCC TAC GTC AGC AGG CGC CAC    720
Ala Val Glu Ala Gly Phe Asp Trp Val Ser Tyr Val Ser Arg Arg His
225                 230                 235                 240

ATC TAC TGC TCC GTC AAG TCA GAT TCG TCG ATC AGT TCC CAC GTG CAC    768
Ile Tyr Cys Ser Val Lys Ser Asp Ser Ser Ile Ser Ser His Val His
                245                 250                 255

GGC TGC TTC ACG CCG GAG AGC ACA GCG CTG CTG GAG AGT GGA GTC CGG    816
Gly Cys Phe Thr Pro Glu Ser Thr Ala Leu Leu Glu Ser Gly Val Arg
            260                 265                 270

AAG CCG CTC GGC GAG CTC TCT ATC GGA GAT CGT GTT TTG AGC ATG ACC    864
Lys Pro Leu Gly Glu Leu Ser Ile Gly Asp Arg Val Leu Ser Met Thr
        275                 280                 285

GCC AAC GGA CAG GCC GTC TAC AGC GAA GTG ATC CTC TTC ATG GAC CGC    912
Ala Asn Gly Gln Ala Val Tyr Ser Glu Val Ile Leu Phe Met Asp Arg
290                 295                 300

AAC CTC GAG CAG ATG CAA AAC TTT GTG CAG CTG CAC ACG GAC GGT GGA    960
Asn Leu Glu Gln Met Gln Asn Phe Val Gln Leu His Thr Asp Gly Gly
305                 310                 315                 320

GCA GTG CTC ACG GTG ACG CCG GCT CAC CTG GTT AGC GTT TGG CAG CCG   1008
Ala Val Leu Thr Val Thr Pro Ala His Leu Val Ser Val Trp Gln Pro
                325                 330                 335

GAG AGC CAG AAG CTC ACG TTT GTG TTT GCG CAT CGC ATC GAG GAG AAG   1056
Glu Ser Gln Lys Leu Thr Phe Val Phe Ala His Arg Ile Glu Glu Lys
            340                 345                 350

AAC CAG GTG CTC GTA CGG GAT GTG GAG ACG GGC GAG CTG AGG CCC CAG   1104
Asn Gln Val Leu Val Arg Asp Val Glu Thr Gly Glu Leu Arg Pro Gln
        355                 360                 365

CGA GTG GTC AAG TTG GGC AGT GTG CGC AGT AAG GGC GTG GTC GCG CCG   1152
Arg Val Val Lys Leu Gly Ser Val Arg Ser Lys Gly Val Val Ala Pro
```

```
                370                 375                 380
CTG ACC CGC GAG GGC ACC ATT GTG GTC AAC TCG GTG GCC GCC AGT TGC     1200
Leu Thr Arg Glu Gly Thr Ile Val Val Asn Ser Val Ala Ala Ser Cys
385                 390                 395                 400

TAT GCG GTG ATC AAC AGT CAG TCG CTG GCC CAC TGG GGA CTG GCT CCC     1248
Tyr Ala Val Ile Asn Ser Gln Ser Leu Ala His Trp Gly Leu Ala Pro
                405                 410                 415

ATG CGC CTG CTG TCC ACG CTG GAG GCG TGG CTG CCC GCC AAG GAG CAG     1296
Met Arg Leu Leu Ser Thr Leu Glu Ala Trp Leu Pro Ala Lys Glu Gln
            420                 425                 430

TTG CAC AGT TCG CCG AAG GTG GTG AGC TCG GCG CAG CAG CAG AAT GGC     1344
Leu His Ser Ser Pro Lys Val Val Ser Ser Ala Gln Gln Gln Asn Gly
            435                 440                 445

ATC CAT TGG TAT GCC AAT GCG CTC TAC AAG GTC AAG GAC TAC GTG CTG     1392
Ile His Trp Tyr Ala Asn Ala Leu Tyr Lys Val Lys Asp Tyr Val Leu
450                 455                 460

CCG CAG AGC TGG CGC CAC GAT TGA                                     1416
Pro Gln Ser Trp Arg His Asp
465                 470

(2) INFORMATION FOR SEQ ID NO: 20:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO: 20:

Met Asp Asn His Ser Ser Val Pro Trp Ala Ser Ala Ser Val Thr
1               5                   10                  15

Cys Leu Ser Leu Gly Cys Gln Met Pro Gln Phe Gln Phe Gln Phe Gln
                20                  25                  30

Leu Gln Ile Arg Ser Glu Leu His Leu Arg Lys Pro Ala Arg Arg Thr
            35                  40                  45

Gln Thr Met Arg His Ile Ala His Thr Gln Arg Cys Leu Ser Arg Leu
        50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
                100                 105                 110

Glu Tyr Thr Asn Ser Ala Ser Gly Pro Leu Glu Gly Val Ile Arg Arg
            115                 120                 125

Asp Ser Pro Lys Phe Lys Asp Leu Val Pro Asn Tyr Asn Arg Asp Ile
        130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
                180                 185                 190

His His Gly Gln Glu Ser Leu His Tyr Glu Gly Arg Ala Val Thr Ile
            195                 200                 205

Ala Thr Ser Asp Arg Asp Gln Ser Lys Tyr Gly Met Leu Ala Arg Leu
        210                 215                 220
```

-continued

```
Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
                260                 265                 270

Lys Pro Leu Gly Glu Leu Ser Ile Gly Asp Arg Val Leu Ser Met Thr
                275                 280                 285

Ala Asn Gly Gln Ala Val Tyr Ser Glu Val Ile Leu Phe Met Asp Arg
290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
                340                 345                 350

Asn Gln Val Leu Val Arg Asp Val Glu Thr Gly Glu Leu Arg Pro Gln
                355                 360                 365

Arg Val Val Lys Leu Gly Ser Val Arg Ser Lys Gly Val Val Ala Pro
                370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ser Ala Gln Gln Gln Asn Gly
                435                 440                 445

Ile His Trp Tyr Ala Asn Ala Leu Tyr Lys Val Lys Asp Tyr Val Leu
                450                 455                 460

Pro Gln Ser Trp Arg His Asp
465                 470
```

(2) INFORMATION FOR SEQ ID NO: 21:

(i) SEQUENCE CHARACTERISTICS:
        (A) LENGTH: 221 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 21:

```
Cys Gly Pro Gly Arg Gly Xaa Gly Xaa Arg Arg His Pro Lys Lys Le
1               5                   10                  15

Thr Pro Leu Ala Tyr Lys Gln Phe Ile Pro Asn Val Ala Glu Lys Th
                20                  25                  30

Leu Gly Ala Ser Gly Arg Tyr Glu Gly Lys Ile Xaa Arg Asn Ser Gl
                35                  40                  45

Arg Phe Lys Glu Leu Thr Pro Asn Tyr Asn Pro Asp Ile Ile Phe Ly
                50                  55                  60

Asp Glu Glu Asn Thr Gly Ala Asp Arg Leu Met Thr Gln Arg Cys Ly
65                  70                  75                  80

Asp Lys Leu Asn Xaa Leu Ala Ile Ser Val Met Asn Xaa Trp Pro Gl
```

-continued

```
                85                  90                  95
Val Xaa Leu Arg Val Thr Glu Gly Trp Asp Glu Asp Gly His His Xa
            100                 105                 110
Glu Glu Ser Leu His Tyr Glu Gly Arg Ala Val Asp Ile Thr Thr Se
            115                 120                 125
Asp Arg Asp Xaa Ser Lys Tyr Gly Xaa Leu Xaa Arg Leu Ala Val Gl
    130                 135                 140
Ala Gly Phe Asp Trp Val Tyr Tyr Glu Ser Lys Ala His Ile His Cy
145                 150                 155                 160
Ser Val Lys Ala Glu Asn Ser Val Ala Ala Lys Ser Gly Gly Cys Ph
                165                 170                 175
Pro Gly Ser Ala Xaa Val Xaa Leu Xaa Xaa Gly Gly Xaa Lys Xaa Va
            180                 185                 190
Lys Asp Leu Xaa Pro Gly Asp Xaa Val Leu Ala Ala Asp Xaa Xaa Gl
            195                 200                 205
Xaa Leu Xaa Xaa Ser Asp Phe Xaa Xaa Phe Xaa Asp Arg
    210                 215                 220
```

(2) INFORMATION FOR SEQ ID NO: 22:

(i) SEQUENCE CHARACTERISTICS:
        (A) LENGTH: 167 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 22:

```
Cys Gly Pro Gly Arg Gly Xaa Xaa Xaa Arg Arg Xaa Xaa Xaa Pro Ly
1               5                   10                  15
Xaa Leu Xaa Pro Leu Xaa Tyr Lys Gln Phe Xaa Pro Xaa Xaa Xaa Gl
            20                  25                  30
Xaa Thr Leu Gly Ala Ser Gly Xaa Xaa Glu Gly Xaa Xaa Xaa Arg Xa
            35                  40                  45
Ser Glu Arg Phe Xaa Xaa Leu Thr Pro Asn Tyr Asn Pro Asp Ile Il
    50                  55                  60
Phe Lys Asp Glu Glu Asn Xaa Gly Ala Asp Arg Leu Met Thr Xaa Ar
65                  70                  75                  80
Cys Lys Xaa Xaa Xaa Asn Xaa Leu Ala Ile Ser Val Met Asn Xaa Tr
                85                  90                  95
Pro Gly Val Xaa Leu Arg Val Thr Glu Gly Xaa Asp Glu Asp Gly Hi
            100                 105                 110
His Xaa Xaa Xaa Ser Leu His Tyr Glu Gly Arg Ala Xaa Asp Ile Th
    115                 120                 125
Thr Ser Asp Arg Asp Xaa Xaa Lys Tyr Gly Xaa Leu Xaa Arg Leu Al
    130                 135                 140
Val Glu Ala Gly Phe Asp Trp Val Tyr Tyr Glu Ser Xaa Xaa His Xa
145                 150                 155                 160
His Xaa Ser Val Lys Xaa Xaa
                165
```

(2) INFORMATION FOR SEQ ID NO: 23:

(i) SEQUENCE CHARACTERISTICS:
        (A) LENGTH: 74 base pairs
        (B) TYPE: nucleic acid (C) STRANDEDNESS: single
        (D) TOPOLOGY: linear (ii) MOLECULE TYPE: nucleic acid (xi) SEQUENCE DESCRIPTION: SEQ ID NO: 23:

GCGCGCTTCG AAGCGAGGCA GCCAGCGAGG GAGAGAGCGA GCGGGCGAGC CGGAGCGAGG    60

AAATCGATGC GCGC    74

(2) INFORMATION FOR SEQ ID NO: 24:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 24:

GCGCGCAGAT CTGGGAAAGC GCAAGAGAGA GCGCACACGC ACACACCCGC CGCGCGCACT    60

CGGGATCCGC GCGC    74

(2) INFORMATION FOR SEQ ID NO: 25:

(i) SEQUENCE CHARACTERISTICS:
        (A) LENGTH: 996 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 25:

CGAAGCGAGG CAGCCAGCGA GGGAGAGAGC GAGCGGGCGA GCCGGAGCGA GGAAATCGAA    60

GGTTCGAATC CTTCCCCCAC CACCATCACT TTCAAAAGTC CGAAAGAATC TGCTCCCTG    120

TTGTGTGTTG GAGGTCGCTG AGTAGTGCGC GAGTAAAATT TAAGCTACAA CAAGGCAAG    180

CTTGACCGAC AATTGCATGA AGAATCTGCT TAGGGTTAGG CGTTTTGCGC TGCTTCGCG    240

TGTACGGGCC AGATATACGC GTTGACATTG ATTATTGACT AGTTATTAAT AGTAATCAA    300

TACGGGGTCA TTAGTTCATA GCCCATATAT GGAGTTCCGC GTTACATAAC TTACGGTAA    360

TGGCCCGCCT GGCTGACCGC CCAACGACCC CCGCCCATTG ACGTCAATAA TGACGTATG    420

TCCCATAGTA ACGCCAATAG GGACTTTCCA TTGACGTCAA TGGGTGGACT ATTTACGGT    480

AACTGCCCAC TTGGCAGTAC ATCAAGTGTA TCATATGCCA AGTACGCCCC CTATTGACG    540

CAATGACGGT AAATGGCCCG CCTGGCATTA TGCCCAGTAC ATGACCTTAT GGACTTTC    600

TACTTGGCAG TACATCTACG TATTAGTCAT CGCTATTACC ATGGTGATGC GGTTTTGGC    660

GTACATCAAT GGGCGTGGAT AGCGGTTTGA CTCACGGGGA TTTCCAAGTC TCCACCCCA    720

TGACGTCAAT GGGAGTTTGT TTTGGCACCA AAATCAACGG GACTTTCCAA AATGTCGTA    780

CAACTCCGCC CCATTGACGC AAATGGGCGG TAGGCGTGTA CGGTGGGAGG TCTATATAA    840

CAGAGCTCTC TGGCTAACTA GAGAACCCAC TGCTTACTGG CTTATCGAAA TTAATACGA    900

TCACTATAGG GAGACCCAAG CTTGGTACCG AGCTCGGATC GATCTGGGAA AGCGCAAGA    960

AGAGCGCACA CGCACACACC CGCCGCGCGC ACTCGG    996

(2) INFORMATION FOR SEQ ID NO: 26:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 26:

GTCCTGGCGC CGCCGCCGCC GTCGCC                                              26

(2) INFORMATION FOR SEQ ID NO: 27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 27:

TTCCGATGAC CGGCCTTTCG CGGTGA                                              26

(2) INFORMATION FOR SEQ ID NO: 28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 28:

GTGCACGGAA AGGTGCAGGC CACACT                                              26

(2) INFORMATION FOR SEQ ID NO: 29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 29:

GGCTCCGGTA TGTGC                                                          15

(2) INFORMATION FOR SEQ ID NO: 30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 30:

GGGGTACTTC AGGGT                                                          15

(2) INFORMATION FOR SEQ ID NO: 31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear -continued (ii) MOLECULE TYPE: nucleic acid (xi) SEQUENCE DESCRIPTION: SEQ ID NO: 31:

CATTGGCAGG AGGAGTTGAT TGTGG                                25

(2) INFORMATION FOR SEQ ID NO: 32:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: nucleic acid (xi) SEQUENCE DESCRIPTION: SEQ ID NO: 32:

AGCACCTTTT GAGTGGAGTT TGGGG                                25